(12) United States Patent
Butler et al.

(10) Patent No.: US 8,799,012 B2
(45) Date of Patent: *Aug. 5, 2014

(54) SYSTEM AND METHOD FOR COMPARING AND UTILIZING ACTIVITY INFORMATION AND CONFIGURATION INFORMATION FROM MULTIPLE MEDICAL DEVICE MANAGEMENT SYSTEMS

(75) Inventors: Steven I. Butler, Gainsville, FL (US); Todd M. Dunsim, Shorewood, WI (US); Douglas E. Frede, Mequon, WI (US); Nancy G. Hedlund, Lindenhurst, IL (US); Thomas F. Polonus, Evanston, IL (US); Steven J. Pregulman, Glenview, IL (US); Torrance J. Ramaker, Libertyville, IL (US); James E. Tillery, Grayslake, IL (US); Mary Kaye Van Huis, Orland Park, IL (US)

(73) Assignee: Hospira, Inc., Lake Forest, IL (US)

( * ) Notice: Subject to any disclaimer, the term of this patent is extended or adjusted under 35 U.S.C. 154(b) by 355 days.

This patent is subject to a terminal disclaimer.

(21) Appl. No.: 12/886,122

(22) Filed: Sep. 20, 2010

(65) Prior Publication Data
US 2011/0022625 A1 Jan. 27, 2011

Related U.S. Application Data

(62) Division of application No. 11/873,269, filed on Oct. 16, 2007.

(60) Provisional application No. 60/851,971, filed on Oct. 16, 2006.

(51) Int. Cl.
| | |
|---|---|
| *G06Q 50/22* | (2012.01) |
| *G06Q 50/24* | (2012.01) |
| *G06Q 10/06* | (2012.01) |
| *G06Q 10/10* | (2012.01) |
| *G06F 19/00* | (2011.01) |

(52) U.S. Cl.
CPC ............... *G06Q 50/24* (2013.01); *G06Q 50/22* (2013.01); *G06Q 10/06* (2013.01); *G06Q 10/10* (2013.01); *G06F 19/327* (2013.01)

USPC .................................................. 705/2; 705/3

(58) Field of Classification Search
CPC ............................. G06Q 50/22; G06Q 50/24
See application file for complete search history.

(56) References Cited

U.S. PATENT DOCUMENTS 5,713,856 A 2/1998 Eggers et al.
(Continued)

FOREIGN PATENT DOCUMENTS

EP 1174817 A2 1/2002
(Continued)

OTHER PUBLICATIONS

Brownlee, Seth, "Product Spotlight: The Plum A+ with Hospira MedNet Infusion System" Dec. 2005, PP&P Magazene vol. 2 No. 7.*
(Continued)

*Primary Examiner* — Eliza Lam
(74) *Attorney, Agent, or Firm* — Michael R. Crabb

(57) ABSTRACT

A method of aggregating and using medical device data from a plurality of remote institutions. The system and method electronically receives at a central computer system a plurality of established medical device data, each of the plurality of established medical device data being received from a respective medication delivery system, each of the respective medication delivery systems having a respective plurality of medical devices within the respective remote institution, such as medication delivery pumps, associated therewith and utilized therein. The system and method electronically combines and stores the plurality of established medical device data from each of the plurality of remote institutions within a memory, and electronically provides a remote client computer access to at least one of a central reporting application adapted for providing summary information to the remote client computer about the medical device data, and/or other applications.

15 Claims, 30 Drawing Sheets

(56) References Cited

U.S. PATENT DOCUMENTS

| | | |
|---|---|---|
| 5,778,345 A | 7/1998 | McCartney |
| 5,781,442 A | 7/1998 | Engleson et al. |
| 5,867,821 A | 2/1999 | Ballantyne et al. |
| 6,631,353 B1 | 10/2003 | Davis et al. |
| 6,671,563 B1 | 12/2003 | Engelson et al. |
| 6,751,651 B2 | 6/2004 | Crockett |
| 6,871,211 B2 | 3/2005 | Labounty et al. |
| 6,915,170 B2 | 7/2005 | Engleson et al. |
| 7,096,072 B2 | 8/2006 | Engleson et al. |
| 7,103,419 B2 | 9/2006 | Engleson et al. |
| 7,103,578 B2 | 9/2006 | Beck et al. |
| 7,107,106 B2 | 9/2006 | Engleson et al. |
| 7,117,041 B2 | 10/2006 | Engleson et al. |
| 7,171,277 B2 | 1/2007 | Engleson et al. |
| 7,457,804 B2 | 11/2008 | Uber, III et al. |
| 7,471,994 B2 * | 12/2008 | Ford et al. ............... 700/282 |
| 7,835,927 B2 * | 11/2010 | Schlotterbeck et al. .......... 705/3 |
| 2002/0010595 A1 | 1/2002 | Kapp |
| 2002/0032583 A1 | 3/2002 | Joao |
| 2002/0036683 A1 | 3/2002 | Yokoyama et al. |
| 2002/0123905 A1 | 9/2002 | Goodroe et al. |
| 2002/0194329 A1 | 12/2002 | Alling |
| 2003/0036683 A1 | 2/2003 | Kehr et al. |
| 2003/0158749 A1 | 8/2003 | Olchanski et al. |
| 2004/0064341 A1 | 4/2004 | Langan et al. |
| 2004/0078236 A1 | 4/2004 | Stoodley et al. |
| 2004/0128162 A1 | 7/2004 | Schlotterbeck et al. |
| 2004/0128163 A1 * | 7/2004 | Goodman et al. ................. 705/2 |
| 2004/0172283 A1 | 9/2004 | Vanderveen et al. |
| 2004/0176980 A1 | 9/2004 | Bulitta et al. |
| 2004/0243438 A1 | 12/2004 | Mintz |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0049910 A1 | 3/2005 | Lancaster et al. |
| 2005/0055242 A1 * | 3/2005 | Bello et al. ................ 705/2 |
| 2005/0102162 A1 | 5/2005 | Blumenfeld |
| 2005/0144043 A1 | 6/2005 | Holland et al. |
| 2005/0154769 A1 | 7/2005 | Eckart et al. |
| 2005/0160057 A1 | 7/2005 | Wefers et al. |
| 2005/0171815 A1 | 8/2005 | Vanderveen |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0234746 A1 | 10/2005 | Funahashi |
| 2005/0278194 A1 | 12/2005 | Holland et al. |
| 2006/0026205 A1 | 2/2006 | Butterfield |
| 2006/0053036 A1 | 3/2006 | Coffman et al. |
| 2006/0074920 A1 | 4/2006 | Wefers et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122867 A1 | 6/2006 | Eggers et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173715 A1 | 8/2006 | Wang |
| 2006/0190302 A1 | 8/2006 | Eggers et al. |
| 2006/0200369 A1 | 9/2006 | Batch et al. |
| 2002/0229918 | 10/2006 | Fotsch et al. |
| 2006/0229918 A1 | 10/2006 | Fotsch et al. |
| 2006/0259327 A1 | 11/2006 | Hoag |
| 2007/0100667 A1 | 5/2007 | Bardy |

FOREIGN PATENT DOCUMENTS

| | | |
|---|---|---|
| JP | 2003-016183 A | 1/2003 |
| JP | 2005-527284 A | 11/2003 |
| JP | 2005-284846 A | 10/2005 |
| JP | 2006-047319 A | 2/2006 |
| WO | 9213322 A1 | 8/1992 |
| WO | 02/069099 A2 | 9/2002 |
| WO | 03/091836 A2 | 11/2003 |
| WO | 2004/072828 A2 | 8/2004 |
| WO | 2005/036447 A2 | 4/2005 |
| WO | 2005/050526 A2 | 6/2005 |
| WO | 2005/066872 A2 | 7/2005 |

OTHER PUBLICATIONS

International Search Report for PCT/US 07/81549, Aug. 18, 2008.
Written Opinion of the International Searching Authority for PCT/US 07/81549, Aug. 18, 2008.
Office Action, Japanese Patent Office, application No. JP20090533485T, issued Jan. 15, 2013.

\* cited by examiner

HOSPIRA MEDNET ® PORTAL
WELCOME JOHN!

THIS SITE GIVES YOU ACCESS TO THE HOSPIRA MEDNET PORTAL, WHICH INCLUDES THE RXRULES ONLINE REPOSITORY.

STEP 1. REVIEW DEFAULT ENTITY PREFERENCES
LISTED BELOW ARE THE ENTITIES THAT HAVE BEEN ASSIGNED TO YOU. THE PEER GROUPS YOU BELONG TO ARE BASED ON THE ENTITY INFORMATION AND POPULATE YOUR DEFAULT PREFERENCES. THESE PREFERENCES WILL REMAIN AS YOU CONTINUE USING RXRULES UNLESS YOU SELECT DIFFERENT OPTIONS IN STEP 2. IF YOUR PEER GROUP CONSIST OF LESS THAN 5 MEMBERS, YOU MAY WANT TO CHANGE YOUR PREFERENCES FOR THIS SESSION ONLY.

| ENTITY NAME | ADDRESS | CITY | STATE | ENTITY TYPE | BED SIZE | PEER GROUP # OF MEMBERS IN PEER GROUP |
|---|---|---|---|---|---|---|
| ENTITY 1 | LOGIN TESTING | LAKE FOREST | IL | RURAL | 12 | 7 |
| ENTITY 2 | 200 KENNEDY DR | LAKE FOREST | IL | RURAL | 21 | 7 |
| ENTITY 3 | ADDRESS | LAKE FOREST | IL | RURAL | 211 | 3 |

STEP 2. MODIFY AND SELECT PREFERENCES FOR THIS SESSION
PLEASE SELECT AN ENTITY IN THE ENTITY FIELD (THIS IS A REQUIRED FIELD MARKED BY AN ASTERISK). ALL OTHER FIELDS ARE BASED ON YOUR DEFAULT PREFERENCES. TO CHANGE YOUR PEER GROUP PREFERENCES FOR THIS SESSION ONLY, SELECT OPTIONS FROM THE REMAINING DROP-DOWN BOXES BELOW, THEN CLICK CONTINUE.

| | | |
|---|---|---|
| ENTITY NAME* | SELECT ▷ | ← 400 |
| ENTITY TYPE | RURAL ▷ | ← 404 |
| BED SIZE | 1-99 ▷ | ← 408 |
| DEFAULT INFUSER TYPE | PLUM A+ ▷ | ← 412 |
| DEFAULT GRAPH TIMEFRAME | BYMONTH ▷ | ← 416 |

MR. JOHN DOE
LAST LOGIN:
9/22/2006 8:35:28 AM

FIG. 4A

MR. JOHN DOE

LAST LOGIN:
9/22/2006 8:35:28 AM

HOSPIRA MEDNET ® PORTAL
WELCOME JOHN!

THIS SITE GIVES YOU ACCESS TO THE HOSPIRA MEDNET PORTAL, WHICH INCLUDES THE RXRULES ONLINE REPOSITORY.

STEP 1. REVIEW DEFAULT ENTITY PREFERENCES
LISTED BELOW ARE THE ENTITIES THAT HAVE BEEN ASSIGNED TO YOU. THE PEER GROUPS YOU BELONG TO ARE BASED ON THE ENTITY INFORMATION AND POPULATE YOUR DEFAULT PREFERENCES. THESE PREFERENCES WILL REMAIN AS YOU CONTINUE USING RXRULES UNLESS YOU SELECT DIFFERENT OPTIONS IN STEP 2. IF YOUR PEER GROUP CONSIST OF LESS THAN 5 MEMBERS, YOU MAY WANT TO CHANGE YOUR PREFERENCES FOR THIS SESSION ONLY.

| ENTITY NAME | ADDRESS | CITY | STATE | ENTITY TYPE | PEER GROUP BED SIZE | # OF MEMBERS IN PEER GROUP |
|---|---|---|---|---|---|---|
| ENTITY 1 | LOGIN TESTING | LAKE FOREST | IL | RURAL | 12 | 7 |
| ENTITY 2 | 200 KENNEDY DR | LAKE FOREST | IL | RURAL | 21 | 7 |
| ENTITY 3 | ADDRESS | LAKE FOREST | IL | RURAL | 211 | 3 |

STEP 2. MODIFY AND SELECT PREFERENCES FOR THIS SESSION
PLEASE SELECT AN ENTITY IN THE ENTITY FIELD (THIS IS A REQUIRED FIELD MARKED BY AN ASTERISK). ALL OTHER FIELDS ARE BASED ON YOUR DEFAULT PREFERENCES. TO CHANGE YOUR PEER GROUP PREFERENCES FOR THIS SESSION ONLY, SELECT OPTIONS FROM THE REMAINING DROP-DOWN BOXES BELOW, THEN CLICK CONTINUE.

| | |
|---|---|
| ENTITY NAME* | SELECT ▽ — 400 |
| ENTITY TYPE | COMMUNITY ▽ — 404 |
| BED SIZE | 1-99 ▽ — 408 |
| DEFAULT INFUSER TYPE | PLUM A+ ▽ — 412 |

[CONTINUE] [RESET]

FIG. 4B

| HOSPIRA.COM | MY PROFILE | CHANGE PASSWORD | CONTACT US |

HOSPIRA MEDNET® RX RULES ONLINE REPOSITORY

CLINICAL CARE AREA (CCA) DISTRIBUTION

ENTITY: ENTITY 2

PREFERENCES

TO CHANGE YOUR PREFERENCES AND RECEIVE AN UPDATED LIST OF
ENTITIES BELOW, SELECT OPTIONS FROM THE DROP-DOWN BOXES AND
CLICK SEARCH.

INFUSER TYPE [PLUM A+ ▽]  ENTITY TYPE [RURAL ▽]  BED SIZE [1-99 ▽]

| INFUSER TYPE | FACILITY TYPE | BED SIZE |
|---|---|---|
| PLUM A+ | MULTI-HOSPITAL HEALTH SYSTEM | 100-199 |
| PLUM A+ | RURAL | 1-99 |
| LIFECARE PCA | MULTI-HOSPITAL HEALTH SYSTEM | 100-199 |
| LIFECARE PCA | RURAL | 1-99 |

← 900

HIDE

[SEARCH] [RESET] [CANCEL]

- RX RULES
- PREFERENCES
- HELP
- LOGOFF

FIG. 9

| HOSPIRA.COM | MY PROFILE | CHANGE PASSWORD | CONTACT US |

HOSPIRA MEDNET® RX RULES ONLINE REPOSITORY

CLINICAL CARE AREA (CCA) DISTRIBUTION

ENTITY: ENTITY 1

PREFERENCES

TO CHANGE YOUR PREFERENCES AND RECEIVE AN UPDATED LIST OF ENTITIES BELOW, SELECT OPTIONS FROM THE DROP-DOWN BOXES AND CLICK SEARCH.

INFUSER TYPE [PLUM A+ ▽]  ENTITY TYPE [RURAL ▽]  BED SIZE [1-99 ▽]

[SEARCH] [RESET] [CANCEL]                     MATCH OPPORTUNITIES

RESULTS BASED ON ABOVE PREFERENCES

BELOW IS A LIST OF THE ENTITIES FOR WHICH YOU CAN COMPARE CCA DISTRIBUTIONS. PLEASE SELECT AN ENTITY OR ENTITIES TO VIEW THEIR RESULTS AND CLICK SHOW REPORT. YOU CAN ALSO CLICK ON THE NAME OF AN ENTITY TO VIEW THE SERVICE LINES INCLUDED FOR THAT ENTITY.

| SELECT | ENTITY NAME* |
|---|---|
| ☐ | SAMPLE ENTITY 1 |
| ☐ | SAMPLE ENTITY 2 |

↙ 1000

[SHOW REPORT]

— RX RULES
— PREFERENCES
— HELP
— LOGOFF

MR. JOHN DOE
LAST LOGIN:
9/22/2006 2:48:39 PM

FIG. 10

| HOSPIRA.COM | MY PROFILE | CHANGE PASSWORD | CONTACT US |

HOSPIRA MEDNET® RX RULES ONLINE REPOSITORY
CLINICAL CARE AREA (CCA) DISTRIBUTION
ENTITY: ENTITY 1
PREFERENCES
TO CHANGE YOUR PREFERENCES AND RECEIVE AN UPDATED LIST OF ENTITIES BELOW, SELECT OPTIONS FROM THE DROP-DOWN BOXES AND CLICK SEARCH.
INFUSER TYPE [PLUM A+ ▽]  ENTITY TYPE [RURAL ▽]  BED SIZE [1-99 ▽]

MATCH OPPORTUNITIES

[SEARCH] [RESET] [CANCEL]

RESULTS BASED ON ABOVE PREFERENCES
BELOW IS A LIST OF THE ENTITIES FOR WHICH YOU CAN COMPARE CCA DISTRIBUTIONS. PLEASE SELECT AN ENTITY OR ENTITIES TO VIEW THEIR RESULTS AND CLICK SHOW REPORT. YOU CAN ALSO CLICK ON THE NAME OF AN ENTITY TO VIEW THE SERVICE LINES INCLUDED FOR THAT ENTITY.

- RX RULES
- PREFERENCES
- HELP
- LOGOFF

MR. JOHN DOE

LAST LOGIN:
9/22/2006 2:48:39 PM

| SELECT | ENTITY NAME* |
|---|---|
| ☐ | SAMPLE ENTITY 1 |
| ☐ | SAMPLE ENTITY 2 |

1100

[SHOW REPORT]

TO REMOVE A SAMPLE ENTITY FROM THE LIST, SCROLL DOWN AND CLICK REMOVE BELOW THE RESULTS.

1108

SELECT LIST:

SAMPLE ENTITY 1

| SERVICE LINE | CCA NAME |
|---|---|
| ICU-GENERAL | ICU |
| MEDICINE-ADULT | MEDSURG |
| OTHER SPECIALTY | TRAINING-LD |
| OTHER SPECIALTY | TRAINING-HD |
| PAIN MANAGEMENT | LOW DOSE |
| PAIN MANAGEMENT | HIGH DOSE |

[REMOVE]

1004

SAMPLE ENTITY 2

| SERVICE LINE | CCA NAME |
|---|---|
| ICU-GENERAL | ICU |
| MEDICINE-ADULT | MEDSURG |
| OTHER SPECIALTY | TRAINING-HD |
| PAIN MANAGEMENT | LOW DOSE |
| PAIN MANAGEMENT | HIGH DOSE |

[REMOVE]

FIG. 11

*THE ENTITIES LISTED ABOVE ARE SELECTED FROM THE SEARCH CRITERIA IN A RANDOM ORDER (FOR EXAMPLE, SAMPLE ENTITY 1 IN THIS SEARCH MAY OR MAY NOT BE THE SAME AS SAMPLE ENTITY 1 IN THE NEXT SEARCH).

| HOSPIRA.COM | MY PROFILE　　CHANGE PASSWORD　　CONTACT US |
|---|---|
| | HOSPIRA MEDNET® RX RULES ONLINE REPOSITORY |
| | DOSAGE LIMITS |
| | ENTITY: ENTITY 1 |
| | PREFERENCES |
| | THE INFUSER TYPE, ENTITY TYPE AND BED SIZE FIELDS ARE PRE-POPULATED WITH YOUR DEFAULT PREFERENCES. YOU CAN CHANGE THESE DEFAULTS BY SELECTING DIFFERENT OPTIONS FROM THE DROP-DOWN BOXES. |
| —RX RULES | PLEASE SELECT THE SERVICE LINE FOR WHICH YOU WOULD LIKE TO VIEW MEDICATION DOSAGE LIMITS AND CLICK SEARCH. |
| —PREFERENCES | |
| —HELP | INFUSER TYPE [PLUM A+ ▽]　　ENTITY TYPE [RURAL ▽] |
| —LOGOFF | BED SIZE [1-99 ▽]　　SERVICE LINE [ICU-GENERAL ▽] |
| | MATCH OPPORTUNITIES |
| | [SEARCH]　[RESET]　[CANCEL] |
| | RESULTS BASED ON ABOVE PREFERENCES |
| MR. JOHN DOE | PLEASE SELECT UP TO 5 MEDICATIONS AT ONE TIME TO VIEW THEIR CONCENTRATION AND DOSAGE LIMITS, THEN CLICK SHOW REPORT. MEDICATIONS PREVIOUSLY VIEWED WITH THE SAME PREFERENCES WILL BE MARKED WITH A FLAG WHEN YOU RETURN TO THIS LIST. THE COUNT COLUMN CONTAINS THE NUMBER OF DOSAGES FOR EACH MEDICATION IN THIS PEER GROUP. |
| LAST LOGIN: | |
| 9/22/2006 2:48:39 PM | |

| SELECT | COUNT | GENERIC MEDICATION NAME |
|---|---|---|
| ☐ | 1 | DOBUTAMINE |
| ☐ | 2 | DOPAMINE |
| ☐ | 1 | HEPARIN |
| ☐ | 1 | INSULIN |
| ☐ | 1 | NITROGLYCERIN |
| ☐ | 1 | POTASSIUM CHLORIDE |
| ☐ | 1 | VANCOMYCIN |

1300

[SHOW REPORT]

FIG. 13

HOSPIRA.COM

MY PROFILE | CHANGE PASSWORD | CONTACT US

HEALTH SYSTEM MAINTENANCE — 1700

HEALTH SYSTEM NAME: 
CITY: 
STATE: 
PHONE:

[SEARCH] 1740  [RESET] 1730

HIDE SEARCH — 1720

PAGE 1 OF 1 — 1702

| EDIT | CUSTOMER ID | HEALTH SYSTEM NAME | ADDRESS | CITY | STATE | ZIP | PHONE | E-MAIL | NO. OF BEDS | ACTIVE | SERVER LIST | FACILITY LIST |
|---|---|---|---|---|---|---|---|---|---|---|---|---|
| EDIT | 10000001 | HEALTH SYSTEM 1 | ADDRESS 1 | CITY 1 | STATE 1 | 11111 | (111)111-1111 | TEST@EMAIL.COM | 851 | YES | ▲ | ▲ |
| EDIT | 10000002 | HEALTH SYSTEM 2 | ADDRESS 2 | CITY 2 | STATE 2 | 22222 | (222)222-2222 | TEST@EMAIL.COM | 708 | YES | ▲ | ▲ |
| EDIT | 10000003 | HEALTH SYSTEM 3 | ADDRESS 3 | CITY 3 | STATE 3 | 33333 | (333)333-3333 | TEST@EMAIL.COM | 571 | YES | ▲ | ▲ |
| EDIT | 10000004 | HEALTH SYSTEM 4 | ADDRESS 4 | CITY 4 | STATE 4 | 44444 | (444)444-4444 | TEST@EMAIL.COM | 622 | YES | ▲ | ▲ |
| EDIT | 10000005 | HEALTH SYSTEM 5 | ADDRESS 5 | CITY 5 | STATE 5 | 55555 | (555)555-5555 | TEST@EMAIL.COM | 961 | YES | ▲ | ▲ |
| EDIT | 10000006 | HEALTH SYSTEM 6 | ADDRESS 6 | CITY 6 | STATE 6 | 66666 | (666)666-6666 | TEST@EMAIL.COM | 565 | NO | ▲ | ▲ |
| EDIT | 10000007 | HEALTH SYSTEM 7 | ADDRESS 7 | CITY 7 | STATE 7 | 77777 | (777)777-7777 | TEST@EMAIL.COM | 204 | YES | ▲ | ▲ |
| EDIT | 10000008 | HEALTH SYSTEM 8 | ADDRESS 8 | CITY 8 | STATE 8 | 88888 | (888)888-8888 | TEST@EMAIL.COM | 240 | NO | ▲ | ▲ |
| EDIT | 10000009 | HEALTH SYSTEM 9 | ADDRESS 9 | CITY 9 | STATE 9 | 99999 | (999)999-9999 | TEST@EMAIL.COM | 397 | YES | ▲ | ▲ |
| EDIT | 10000010 | HEALTH SYSTEM 10 | ADDRESS 10 | CITY 10 | STATE 10 | 12345 | (123)111-1111 | TEST@EMAIL.COM | 391 | YES | ▲ | ▲ |
| EDIT | 10000011 | HEALTH SYSTEM 11 | ADDRESS 11 | CITY 11 | STATE 11 | 23456 | (123)222-2222 | TEST@EMAIL.COM | 23 | YES | ▲ | ▲ |
| EDIT | 10000012 | HEALTH SYSTEM 12 | ADDRESS 12 | CITY 12 | STATE 12 | 34567 | (123)333-3333 | TEST@EMAIL.COM | 168 | YES | ▲ | ▲ |
| | | | | | | | | | | | | ADD |

ADMINISTRATION
REPORTS
HELP
LOGOFF

ADMIN USER

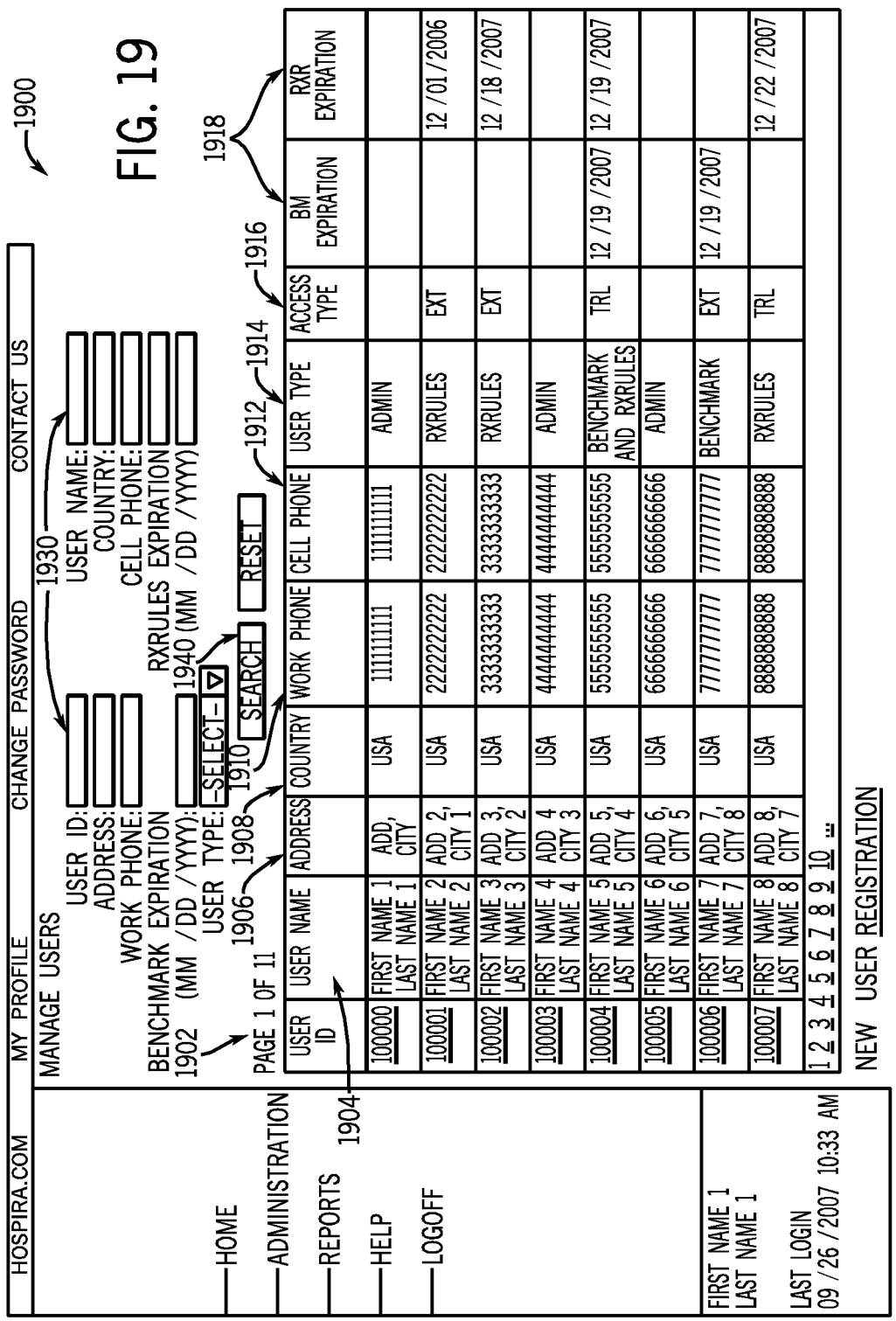

FIG. 20

PLEASE FILL THE BELOW DETAILS TO REGISTER A NEW USER

*FIRST NAME  MIDDLE NAME
*LAST NAME
PREFIX  SUFFIX

ADDRESS DETAILS
*ADDRESS
*CITY
*STATE —SELECT—
*ZIP
*COUNTRY —SELECT—

CONTACT DETAILS
*WORK PHONE ( ) -   CELL PHONE ( ) -
FAX  *EMAIL ADDRESS

CONTRACT DETAILS
*HOSPIRA IDENTIFICATION NUMBER
*USER TYPE  RXRULES
ADDITIONAL INFO.

PASSWORD VALIDATION
*SECRET QUESTION  WHAT IS THE NAME OF YOUR FIRST SCHOOL?
*ANSWER

[REGISTER]  [RESET]

ADMINISTRATION
REPORTS
HELP
LOGOFF

ADMIN USER
LAST LOGIN

FIG. 21

| ADDRESS | | | | | |
|---|---|---|---|---|---|
| HOSPIRA.COM | | | | | ▷ ▷ GO |
| MY PROFILE | CHANGE PASSWORD | | | CONTACT US | |

GENERAL SETTINGS
PLEASE CONSULT IT SUPPORT BEFORE CHANGING OR INACTIVATING ANY OF THE VALUES BELOW. ANY CHANGE CAN POTENTIALLY IMPACT THE NORMAL WORKING OF THIS APPLICATION
PAGE 1 OF 5 ◀━ 2330

/ ← 2300

| | PARAMETER NAME | PARAMETER TYPE | PARAMETER DESC | PARAMETER VALUE | ACTIVE |
|---|---|---|---|---|---|
| EDIT | DEAFULT_BENCHMARK_EXPIRY | EXPIRY_DET | DEAFULT BENCHMARK EXPIRY | 60 | YES |
| EDIT | DEFAULT_RXRULES_EXPIRY | EXPIRY_DET | DEFAULT RXRULES EXPIRY | 60 | YES |
| EDIT | DEFAULT_PASSWORD_EXPIRY | EXPIRY_DET | DEFAULT PASSWORD EXPIRY | 60 | YES |
| EDIT | SEC_QN_01 | SEC_QUESTION | SECRET QUESTION 1 | WHAT IS THE NAME OF YOUR FIRST SCHOOL | YES |
| EDIT | SEC_QN_02 | SEC_QUESTION | SECRET QUESTION 2 | WHAT IS YOUR MOTHER'S MAIDEN NAME | YES |
| EDIT | SEC_QN_03 | SEC_QUESTION | SECRET QUESTION 3 | WHAT IS THE NAME OF YOUR FAVORITE SPORTS TEAM | YES |
| EDIT | APPLICATION_NAME | APP_NAME | THIS IS THE APPLICATION TITLE THAT WILL BE DISPLAYED ON EVERY PAGE OF THE APPLICATION | HOSPIRA MEDNET ® PORTAL | YES |
| EDIT | ADMIN_MAIL_ID | MAILID | ADMIN MAIL ID WHERE THE MAILS ARE SENT WHEN THE LOAD JOB FAILS | (EMAIL ADDRESS) | YES |
| EDIT | BM_REPORT_TRESHHOLD_LIMIT | BM_REPORT_INFO | LIMIT WHICH IS USED TO COMPARE THE NUMBER OF PEERGROUPS IN BENCHMARK REPORT | 2 | YES |
| EDIT | RX_REPORT_CCA_MAX_SELECT | RX_REPORT_INFO | MAXIMUM NO. OF SAMPLE FACILITY SELECTION IN THE CCA DISTRIBUTION PAGE | 3 | YES |
| EDIT | RX_REPORT_DOSAGE_LIMIT_MAX_SELECT | RX_REPORT_INFO | MAXIMUM NO. OF GENERIC DRUG NAME SELECTION IN THE RXRULES DOSAGE LIMIT PAGE | 5 | YES |
| EDIT | BM_RAWDATA_RETENTION | DATA_RETENTION | RETENTION PERIOD FOR | 3 | YES |

ADMINISTRATION
REPORTS
HELP — 2308
LOGOFF 2302
2304
2306
2310
2314
2316
2318
2312

FIG. 23

SYSTEM AND METHOD FOR COMPARING AND UTILIZING ACTIVITY INFORMATION AND CONFIGURATION INFORMATION FROM MULTIPLE MEDICAL DEVICE MANAGEMENT SYSTEMS

CROSS-REFERENCE TO RELATED APPLICATIONS

This application is a divisional of U.S. patent application Ser. No. 11/873,269, filed Oct. 16, 2007, which claims the benefit of and priority to U.S. Provisional Patent Application Ser. No. 60/851,971, filed Oct. 16, 2006, both applications having the title "System and Method for Comparing and Utilizing Activity Information and Configuration Information from Multiple Device Management Systems," the entirety of all of which are hereby incorporated by reference.

FEDERALLY SPONSORED RESEARCH OR DEVELOPMENT

None.

TECHNICAL FIELD

The invention relates to systems and methods for utilizing information generated by remote medical device management systems from multiple medical institutions and/or facilities. More particularly, the present invention relates to providing aggregated data, including but not limited to configuration information and activity information regarding medical devices, such as medication delivery pumps, to remote medical institutions and/or facilities for device configuration library development and/or benchmarking purposes.

BACKGROUND OF THE INVENTION

Modern medical care often involves the use of electronic medical devices such as medication delivery pumps and/or patient condition monitors. Electronic medical pumps, for example, can be electronically loaded or configured with a customizable "drug library" containing certain drug delivery information or parameters, as disclosed in U.S. Pat. Nos. 5,681,285 and 6,269,340. Medication management systems for configuring, controlling, and monitoring medication delivery devices have been disclosed. For example, commonly owned U.S. patent application Ser. No. 10/930,358, which published as US20050144043A1 on Jun. 30, 2005 and U.S. patent application Ser. No. 10/783,573, which published as US20050278194A1 on Dec. 15, 2005, disclose a medication management system in which a user-customizable drug library or medical device configuration information is prepared using a drug library editor (DLE) program and module of a medication management unit (MMU). The MMU downloads the customizable drug library to the medication delivery pump and receives status or activity information from the pump. Commonly owned U.S. patent application Ser. No. 10/783,877, which also published as WO2005050526A2 on Jun. 2, 2005, discloses how the drug library or medical device configuration information is created, edited, stored and communicated to a medication delivery device in the context of a medication management system to deliver substances, such as fluids and/or fluid medication to patients. According to the above-mentioned commonly owned published patent applications, a typical medication management system includes a MMU in communication with one or more medication delivery devices. The MMU is a computer, typically a server, with an associated memory that stores the customized drug library or information for configuring the medication delivery devices and the activity information received from the medication delivery devices.

In the past, the activity and configuration information collected by an individual medication management system was stored in one or more computers at each individual institution and/or facility or in one or more computers set up by the vendor of the system. Other institutions or facilities did not have access to the activity and configuration information for comparison or other purposes.

One of the more difficult and time-consuming tasks for a medical institution to accomplish in order to implement a medication management system is the development of a customized drug library or set of medical device configuration information. Vendors of medication management systems or medical devices are typically not permitted to practice medicine and can only make recommendations that authorized medical personnel at the individual medical institution must review, modify if necessary and approve. Furthermore, medical institutions usually want to customize their drug library or medical device configuration information to best suit the particular needs, medical judgments and practices of their institution. However, the process of developing and approving a drug library or medical device configuration information for an institution can take months and often involves medical personnel from many areas of the institution. To facilitate and expedite the creation, development, and continued maintenance of a drug library or medical device configuration information, a need exists for institutions to understand and compare how other institutions have organized their customized medical device configuration information and what specific values they have used for various parameters or variables, both before and after an institution has installed and implemented a medication management system.

Another difficult task is evaluating the enormous amount of activity information that a medical device management system or medication management system generates. With existing medical device management systems or medication management systems, various reports can be generated by the system to allow the medical institution and/or facility to track various measures. However, it is often hard to draw meaningful conclusions about the data or the reports in the abstract. A need exists to allow an individual medical institution and/or facility to compare their activity information to the activity information of other institutions and/or facilities.

Knowledge in the area of medicine and delivery of medication is not static; it is dynamic and constantly evolving. There is a demand to make continuing improvements in the areas of patient safety, caregiver productivity, and standards of care. Thus, there is a need to have medical device configuration and activity information that is dynamic, up-to-date and based on actual recent experience in medical institutions. It is also desirable for medical institutions and/or facilities to be able to consider what their peers, based on one or more similarity or level of performance factors, are doing relative to medical device configuration and activity information.

One objective of the present invention is the provision of a method and system for aggregating medical device configuration information from multiple medical institutions and/or facilities for the purposes of benchmarking and drug library or medical device configuration information development.

A further objective of the present invention is the provision of a method and system for aggregating medical device activity information generated by one or more medical device management systems at multiple medical institutions and/or facilities for benchmarking or other purposes.

A further objective of the present invention is the provision of medical device configuration and activity information that is dynamic, up-to-date and based on actual recent experience in medical institutions.

A further objective of the present invention is the provision of a method and system that allows medical institutions and/or facilities to select a peer group whose recent medical device configuration and activity information is of interest to them.

A further object of the present invention is the provision of a system and method for being able to remotely develop and/or create configuration libraries, in particular when an institution/facility has purchased a medication delivery system, but the medication delivery system, or portions thereof, has not been installed yet or the installation has not yet been completed.

The present invention is provided to solve the problems discussed above and, to provide advantages and aspects not provided by prior medical pumps, as well as achieve other objects not explicitly stated above. A full discussion of the features, advantages and objects of the present invention is deferred to the following detailed description, which proceeds with reference to the accompanying drawings.

SUMMARY OF THE INVENTION

The invention relates to systems and methods for utilizing information generated by medical device management systems from multiple medical institutions and/or facilities. A medical device management system such as a medication delivery system can include a medication management unit (MMU). The MMU is in communication with one or more medical devices, such as medication delivery pumps or infusers for example. Other types of medical devices including but not limited to patient condition monitors, vital signs monitors, diagnostic devices, imaging devices, and laboratory devices can communicate with, be configured by, and be monitored by the MMU so as to provide information for use with this invention.

The MMU translates the delivery information and/or the medication order, such as the medication to be delivered and the infusion rate, into delivery programming code or information suitable for programming the designated pump or infuser. The MMU can also communicate to the pump a variety of drug library parameters including but not limited to device specific configuration parameters and hard and/or soft limits for medication delivery rates. These drug libraries and/or other configuration parameters can be considered as configuration information, which can include any other information used to configure the medication delivery pump. Thus, these libraries or configuration libraries can include drug libraries and other configuration information. Each medical institution and/or facility can use a configuration information and/or drug library editor (DLE) module of the MMU to customize or make configuration information institution specific and may update the configuration information from time to time. Different clinical care areas (CCA) exist within a medical institution and/or facility, and each area can have different configuration information, such as drug libraries, for downloading into each of the medication delivery pumps within each clinical care area. A configuration information editor deployed as a part of the MMU, its console, or on a separate computer, enables the institution and/or facility user to import, export and edit configuration information, such as whole drug libraries and individual drug library values, to control and customize the configuration information, such as a drug library, according to hospital preferences and clinical care area preferences. The medication delivery pump can replace an existing configuration library in the memory of the medication delivery pump with an updated configuration library that it receives from the MMU.

The MMU can be configured by an institution and/or facility user at the MMU console to monitor and store in memory the activity of each of the medication delivery pumps, such as alarms, events and pump user interface inputs. This and other information relating to the activity of the medication delivery pumps can be stored as activity information in memory within each medication delivery pump or within the MMU and/or within a central institution's and/or facility information system. The MMU console can also be used to generate reports and control the distribution of configuration libraries to one or more of the medical devices.

Thus, in one embodiment, the present invention is directed to a system and method of aggregating and using medication delivery pump information from a plurality of remote institutions and/or facilities. The system and method electronically receives at a central computer system a plurality of established medication delivery data, each of the plurality of established medication delivery data being received from a respective remote medication delivery system and each of the respective remote medication delivery systems having a respective plurality of medication delivery pumps associated therewith and utilized therein. Each of the respective remote medication delivery systems is associated with and implemented within a respective remote institution and/or facility of the plurality of remote institutions/facilities. The system and method further electronically combines and stores the plurality of established medication delivery data from each of the plurality of remote institutions and/or facilities within a central memory, and electronically provides a remote institution and/or facility remote access to a central reporting application. The central reporting application is adapted to electronically receive search parameters from the remote institution and/or facility for querying the combined established medication delivery data and electronically provides summary information to the remote institution and/or facility about the medication delivery data.

In one embodiment, the established medication delivery data includes medication delivery pump configuration information and medication delivery pump activity information. In one embodiment, the established medication delivery data includes medication delivery pump configuration information and medication delivery pump activity information. The configuration information can include drug library information and medication delivery device specific configuration settings. The drug library information can include, but is not limited to, medication name, generic medication name, medication concentration, medication dosing unit, lower hard limit, lower soft limit, upper soft limit, and upper hard limit.

The device or infuser specific configuration information can include, but is not limited to, medication lockout duration, default occlusion pressure, minimum patient weight, maximum patient weight, maximum dose rate, alarm sounds and nurse callback settings. The activity information can include data which is indicative of how the pump is operating, such as delivery or event data and usage information. The delivery or event data can include, but is not limited to, pump type, user keystrokes to operate the medical device, date and time recorded for each event or activity, alarms, alerts, medication name and clinical care area name. The usage information can include, but is not limited to, compliance information, pump utilization information, user response to alarms and alert information and detailed information related to the user activity or response to the operation of the medical device, such as keystrokes and date and time of such response, including responses to soft and hard limit alerts and pump configuration editing information. The search parameters which a user can select or enter to perform at least searching and reporting functions can include, but are not limited to, entity type, bed size (number of beds), pump type, time frame, service line, and/or generic drug name. The summary information can be used for at least one of assisting the remote institution and/or facility user in generating new and/or modified medication delivery parameters and/or assisting the remote institution and/or facility user in implementing new and/or modified institution and/or facility behaviors and/or practices.

In one embodiment, specific institution and/or facility names are withheld from being identified within the summary information. In another embodiment, each established medication delivery data for each remote institution can include a plurality of distinct clinical care specific medication databases established and utilized with a plurality of distinct clinical care areas within each remote institution. Each of the plurality of distinct clinical care areas can have a clinical care area specific set of medication delivery parameters within the respective established medication delivery data for downloading to a medication delivery pump within the specific clinical care area.

In one embodiment, the summary information relating to the medication delivery pump configuration information and/or the medication delivery pump activity information can be provided and made viewable for a specific medication delivery pump from various interface screen displays of the configuration/activity information application. The central computer system and the configuration/activity information can also be configured to provide statistical information through interface screen displays for various aspects of the configuration and/or activity information within the memory. In one embodiment, the central computer system can be configured to compare at least one of the limits within the configuration information for an institution with limits within at least one of configuration information for a peer group for the institution, for another peer group than the peer group of the institution, and/or for all peer groups. The central computer system can then generate statistical information based on the comparison, including a percent of time the limit is used within the configuration information for the peer group for the institution, for another peer group than the peer group of the institution, and/or for all peer groups. The above statistical and other configuration/activity information in summary form or other form for a medical device data can be displayed over predefined time frames and/or over configurable time frames, including at least one of monthly, quarterly, number of days, number of weeks, number of months, number of years, and/or an interval designated by a beginning date and an ending date.

In a further embodiment, the central computer system can compare activity information received from one institution with activity information received from one or more other institutions for providing a comparison result, and can determine if the comparison result satisfies a predetermined condition. If the condition is met, the central computer system can be configured to communicate an alert to the institution. For example, a specific percentage of times a medical device configuration library information is edited during programming of a medical device within the institution in relation to the average number of times medical device configuration library information is edited during programming of medical devices within other institutions, can be compared to determine if an alert should be communicated to an institution. The institution can then review if any action is warranted, such as making an adjustment to configuration information for the medical devices within their institution. The communication can be sent in various ways, such as by e-mail, text message, and/or a page.

In a further embodiment of the present invention, a method of assisting a medical institution in developing an institution-specific customized configuration library for configuring at least one medical device at the institution is provided. The method includes providing a configuration library database comprising medical device configuration information and granting a configuration library developing institution access to view a portion of the configuration library database if access criteria are satisfied. The access criteria can be selected from a group of criteria consisting of active customer status, contract status, subscriber status, data-sharing status, prospect status, user ID match and password match. The developing institution is provided access to copy part of the viewed portion of the configuration library database into an institution-specific customized configuration library database, through remote access to an Internet web site, which can be sponsored by a manufacturer of a medical device. The configuration library database can include drug dosing limits and infuser master settings. The configuration library database can be established by receiving at a central computer system a plurality of previously-established medical device configuration libraries from a corresponding plurality of geographically remote data-sharing institutions at given time. A peer group category designation can be assigned to each of the received previously-established medical device configuration libraries, which can be based on at least facility/entity type, number of beds, medical device type, and/or service line. A searchable relational database can be created including the peer group category designation, from the previously-established medical device configuration libraries. The previously-established configuration libraries can be received at the central computer system at regular time intervals, such as daily, weekly, monthly, quarterly and/or yearly intervals. The central reporting application allows institutions to query the relational database by at least peer group category designation, including being provided access to configuration library information of institutions within the same peer group, other peer groups and/or all peer groups.

In a further embodiment, a method of tracking and comparing activity information for a medical device within an institution is provided. The method includes comparing at a central computer system activity information received from one remote institution, for providing a comparison result, determining if the comparison result satisfies a predetermined condition, and communicating an alert to the institution if the predetermined condition is satisfied. The predetermined condition can include a specific percentage of a number of times a medical device configuration library information is edited during programming in relation to a number of times the medical device is programmed.

In another embodiment, the central computer system and/or the applications therein can be configured to transfer at least a portion of the configuration/activity information database query search results and/or the aggregation of the plurality of established medical device data associated with the search result, to a local storage medium at a remote institution/facility for use within the respective remote medication delivery system. As indicated above, the established medication data can include configuration information including a drug library having a plurality of rule sets for a respective plurality of drugs. Thus, the central computer system and/or applications therein can be configured to transfer at least rule sets for respective drugs to the local storage medium at the remote institution/facility, for at least assisting in the population of new drug entries in a master formulary list and/or CCA sub-list. The transfer can take place through directly importing of the portion of the search result and/or the aggregation of the plurality of established medical device data to a configuration information reporting application, through selecting transfer data using a .csv process, and/or through selecting the portion of the search result and/or the aggregation of the plurality of established medical device data, into a wish list or shopping cart.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 4A is an interface screen display of some exemplary selection functions of facility benchmarking of activity information preferences.

FIG. 4B is another interface screen display of some exemplary selection functions of facility configuration preferences.

FIG. 9 is an interface screen display of preliminary results of particular preferences selected using the selection functions of FIG. 8.

FIG. 10 is an interface screen display of additional selection functions for facility viewing of configuration information preferences, in relation to the selection functions of FIG. 8.

FIG. 11 is an interface screen display of results of particular preferences selected using the selection functions of FIGS. 8 and 10.

FIG. 13 is an interface screen display of preliminary results of particular preferences selected using the selection functions of FIG. 12.

FIG. 17 is a health system or institution maintenance interface screen for viewing, configuring and/or modifying system information.

FIG. 18 is a facility maintenance interface screen for viewing, configuring and/or modifying facility information.

FIG. 19 is a manage users interface screen for viewing, configuring and/or modifying user information.

FIG. 20 is a further manage users interface screen for use in viewing, configuring and/or modifying user information entering and/or updating a individual user profile information.

FIG. 21 is an infuser maintenance interface screen for viewing, configuring and/or modifying infuser information.

FIG. 23 is a general settings interface screen for viewing, configuring and/or modifying general setting information.

DETAILED DESCRIPTION

Figure 1A:
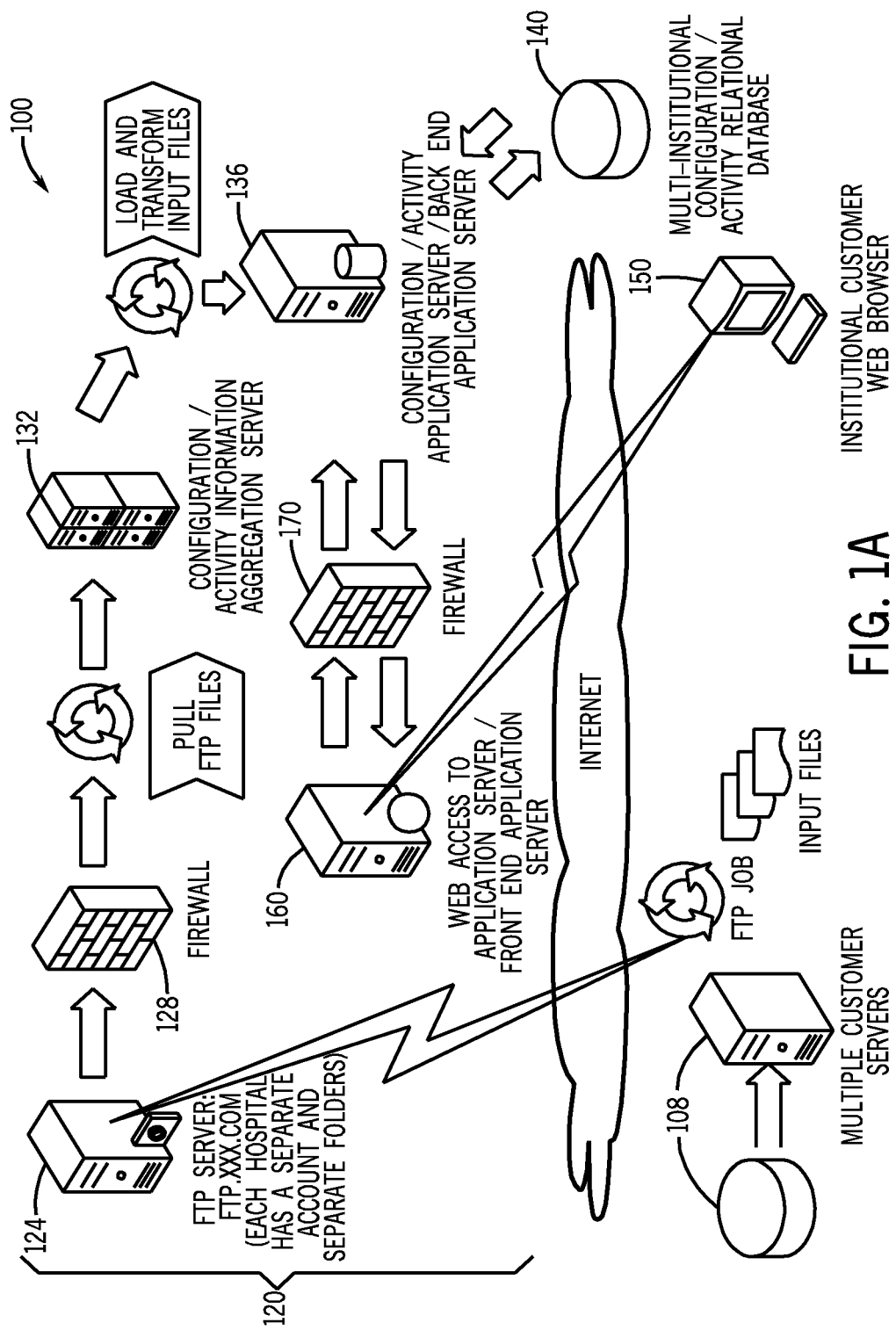
FIG. 1A is an illustration of one embodiment of the system environment of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

As indicated above, a medication delivery system within an institution and/or facility can include configuration information programming systems and/or activity information gathering systems, such as medication management units (MMU). As used herein, an institution can include a health system which has one or more buildings or separate facilities that are owned, leased or managed by a central organization. A facility can be an individual hospital or health care provider. For embodiments in which a facility is a stand alone hospital or health care provider, the facility is also considered a health system or institution. Thus, in one embodiment, multiple facilities will be assigned to one institution. In another embodiment, only one facility will be assigned to an institution. In addition, the term entity is used generically throughout this specification, and includes facilities and health system identification names such as institution, which can also be an institution name, as indicated above.

Figure 15:
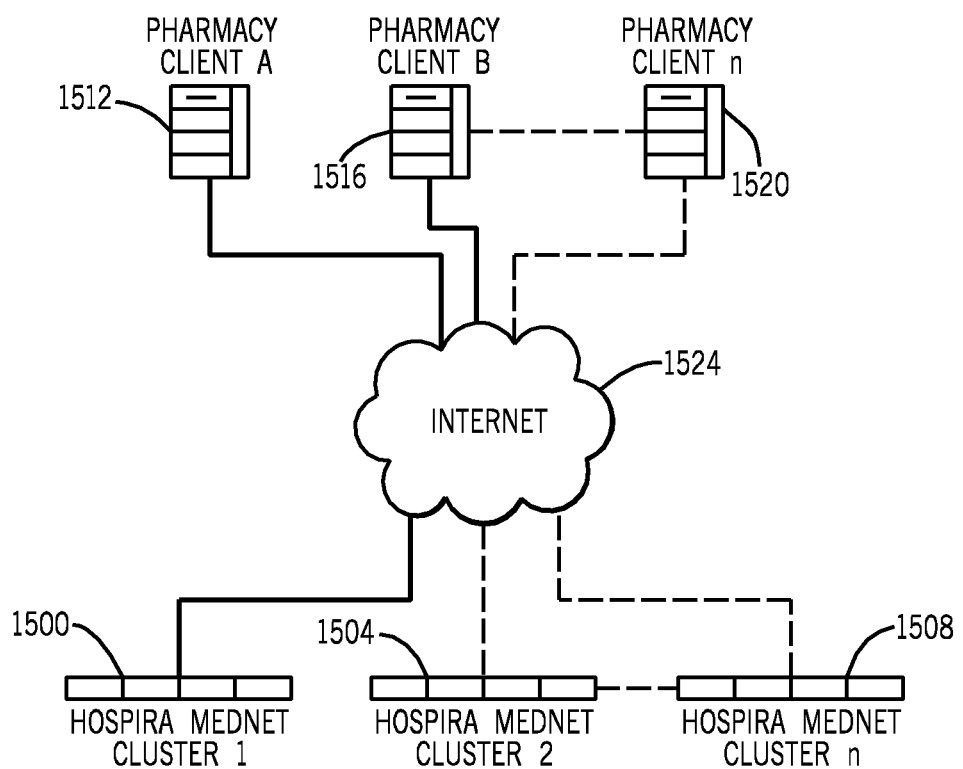
FIG. 15 is a one embodiment of a remote configuration library development system.
Figure 16:
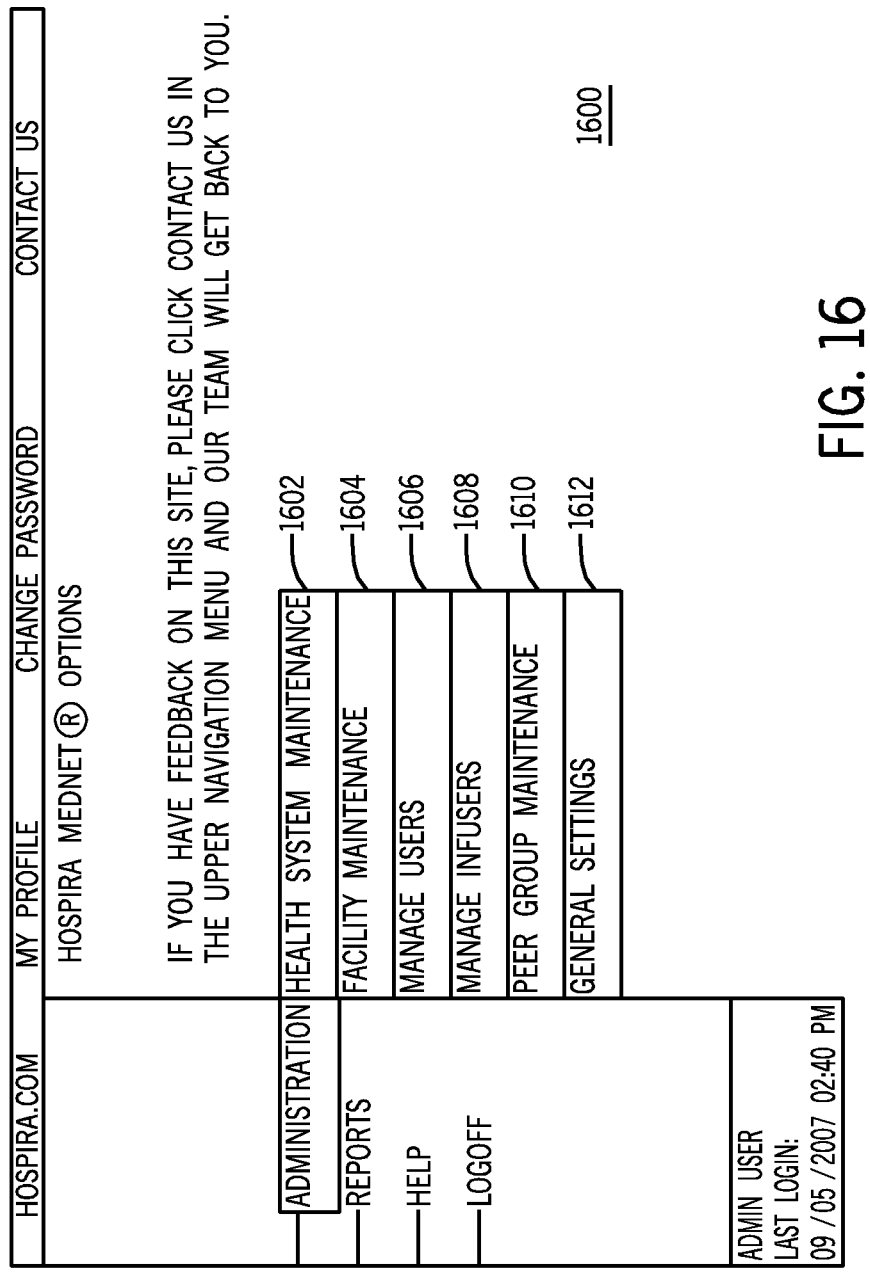
FIG. 16 is an administration options interface screen for selecting from a plurality of administration and maintenance interface screens of at least FIGS. 17-23.

In this context, an institution can implement one or more MMUs for each facility locally, or an institution can implement MMUs at a remote institution or vendor data center which houses one or more servers or virtual servers that act as MMUs for each facility within the institution. As will be described in the context of at least FIG. 1B, the MMUs 182 and respective database 184 can be implemented at a remote vendor data center 120', and can be linked to other systems, such as a configuration/activity application server 136' and related database 140', as described herein. Within an institution data center and/or within a vendor data center 120', the data center can be configured to communicate with institution computer systems 108' which allow for connection and communication with devices, such as infusion pumps (not shown), located at each facility, through a communications network, such as the Internet. In addition to and/or alternatively to this MMU remote data center hosting, a plurality of remote computers 182 (1500, 1504, 1508 in FIG. 15) can be provided for hosting remote configuration library development applications (RCLDAs) 182 therein for creating, editing, developing, and/or maintaining configuration libraries, such as drug libraries for use within medical devices, such as medication delivery pumps. These RCLDAs can be accessed by client computers 150' from each institution/facility, such as through a front end server 180, typically through a firewall 128'. The RCLDAs 182 can be also be accessed through pharmacy client computers 1512, 1516, 1520 shown in FIG. 15, which conceptually would be within customer server(s) 108' shown in FIG. 1B, over a network such as the Internet.

The RCLDA server(s) 182 can be configured according to various known techniques. For example, each institution can be provided its own remote server 182 and have a separate instance of an RCLDA 182 installed therein and running thereon for access and use by a customer through a client 150' or other computer system, through a firewall 128' and/or through a Front End RCLDA server 180. Alternatively, each institution would not be provided with its own server, and institutions would "share" each server 182. In this embodiment, each RCLDA server 182 can be configured to have multiple "virtual servers" running within each physical server, with separate instances of an RCLDA installed within each "virtual" configured segment of memory of the each server, and running therein, again for access and use by a customer through a client 150' or other computer systems, through a firewall 128' and/or through a Front End RCLDA server 180. As a further alternative, a single server 182 can be used in a true application service provider (ASP) arrangement, wherein a single instance of an RCLDA can be installed in the RCLDA server 182, and running therein, again for access and use by a customer through a client 150' or other computer systems, through a firewall 128' and/or through a Front End RCLDA server 180. Server and application installation, including such tasks as login procedure techniques and data separation techniques would need to be configured differently, depending on the particular server and application arrangement chosen from the above alternatives, as one of ordinary skill in the art would understand. For example, in an ASP environment, data and tables for data would need to have at least one additional header, such as a facility or institution header, to differentiate each piece of data as belonging to a particular institution. In the other configurations, this additional header or data identifier would not be needed, as once a customer logged into their separate "server", either physical and/or virtual server, all data related to the RCLDA installed and running therein would be for such particular facility and/or institution. Other configuration differences necessary for each type of installation of RCLDAs would understood by one of ordinary skill in the art, including the configuration of the RCLDA database(s) 184. Each remote configuration library development application (RCLDA) can have similar functionality as existing HOSPIRA MEDNET application functionality, provided by HOSPIRA, INC., the assignee of the present invention. In one embodiment, each "HOSPIRA MEDNET" server can run SQL SERVER software for database creation, having similar database tables as described herein, from client sites throughout the country or the world, via the Internet 1524, as provided above. In a virtual server configuration using VMware's ESX Server, each physical server mentioned above can be configured to run at least six virtual HOSPIRA MEDNET/SQL servers on each physical server.

As provided in one or more of the above and below-referenced patents and/or patent applications, MMUs be used to configure the medical devices, such as medication delivery pumps, as well as store activity information regarding the activity of each of the medical devices. The activity information can be stored in memory within each medication device and/or within the MMUs and/or within a central institution and/or facility information system. The MMU console can also be used to generate reports and control the distribution of the configuration information with the medical devices. Different facility clinical care areas exist within a hospital facility or institution, and each area can have different configuration information, such as drug libraries, for downloading into each of the medical devices within each clinical care area. A configuration information or drug library editor (DLE) deployed as a part of the MMU, its console, or on a separate computer, enables the institution and/or facility user to import, export and edit configuration information, such as whole drug libraries and individual configuration library values, to control and customize a set of configuration information, such as a drug library, according to hospital preferences and clinical care area preferences. Other features, functions and advantages of medication delivery systems and MMUs are shown and described in U.S. patent application Ser. Nos. 10/930,358; 10/783,573; and 10/783,877 which are hereby incorporated by reference herein in their entirety and are commonly owned along with the present invention.

Figure 1B:
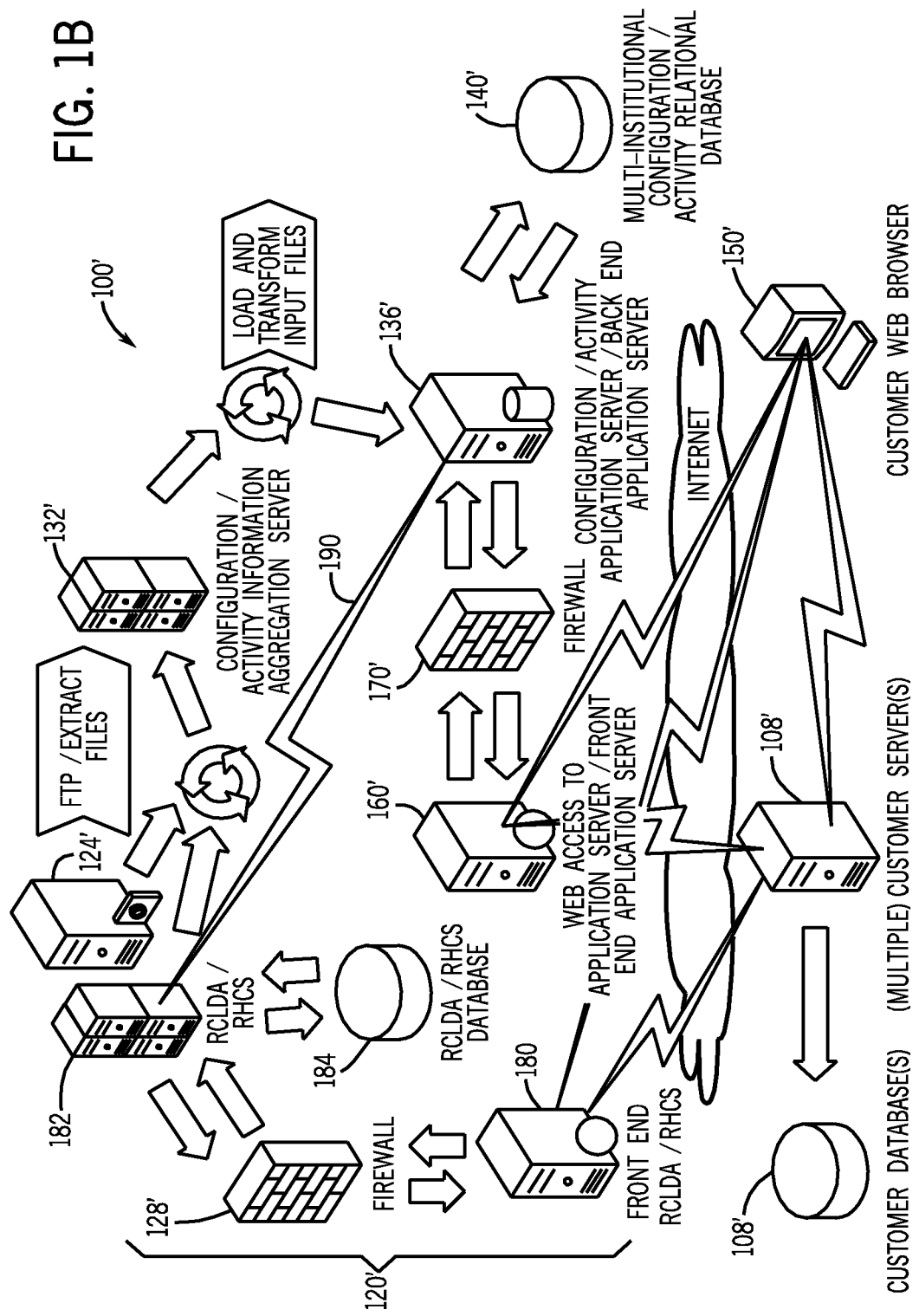
FIG. 1B is an illustration of another embodiment of the system environment of the present invention.

As provided above, DLEs and associated software necessary for creating, editing, developing, and/or maintaining configuration libraries, such as drug libraries, can be implemented in a remote environment as RCLDAs running on a remote server(s) 182, as shown in FIG. 1B. In addition to only the DLE/RCLDA functions of MMUs and HOSPIRA MEDNET being available in a remote environment, such as being provided within a remote institution data center or within a remote vendor data center, all other HOSPIRA MEDNET or MMU functionality otherwise provided within a server or other central computing environment at an institution, can alternatively be implemented within a remote environment, such as being provided within a remote institution data center or within a remote vendor data center. In particular, as shown in FIG. 1B, a remotely hosted customer server (RHCS) 182 and an associated RHCS database 184 can be used to implement MMU and HOSPIRA MEDNET functionality. A firewall 128', a Front End RHCS server, and/or other networking hardware and software necessary for implementing such a configuration is known to one of ordinary skill in the art, for security and other networking communication. An RHCS implementing MMU and HOSPIRA MEDNET functionality can be configured in one or more of the physical, virtual and/or ASP server configurations described above for RCLDAs. Thus, an RHCS and respective HOSPIRA MEDNET/MMU applications can be installed and running in a separate remote physical server 182 for each facility and/or institution. Likewise, an RHCS and respective HOSPIRA MEDNET/MMU applications can be installed and running in a separate remote "virtual" server 182, with multiple similar virtual RHCS server 182 installations being provided in each physical server 182, one for each facility and/or institution. Similarly one server could host a single HOSPIRA MEDNET/MMU application, which hosts multiple customers (facilities and/or institutions), in an ASP environment.

Figure 2:
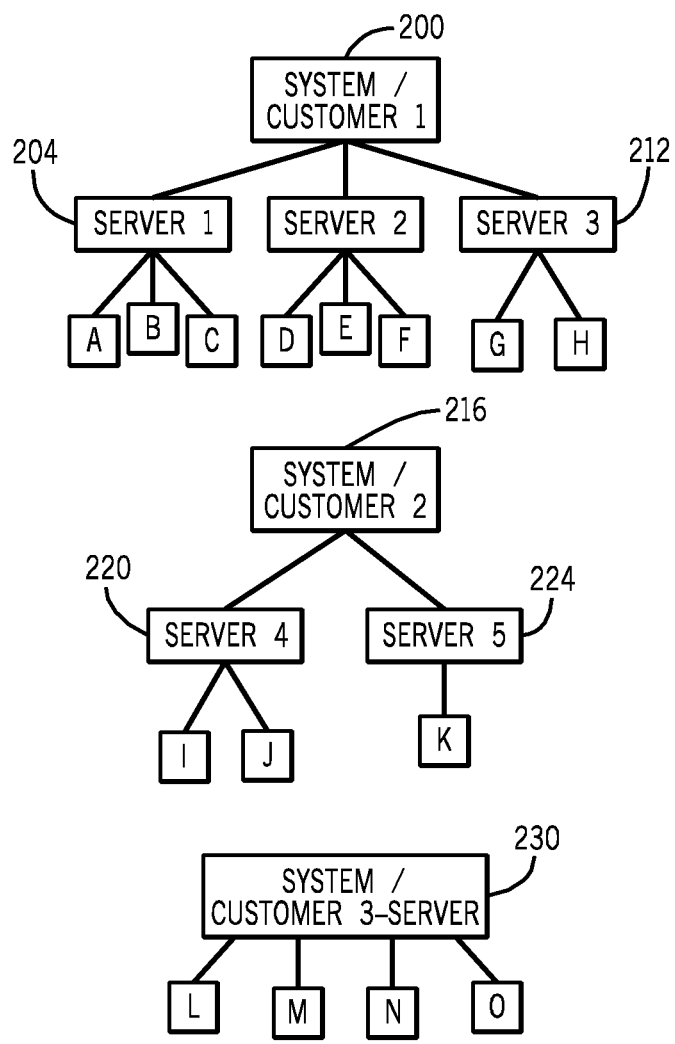
FIG. 2 is an illustration of a block diagram of customer institutions and customer facility systems therein for gathering configuration and/or activity information for use within the present invention.

As provided above herein, and as provided within referred to patents and applications identified herein, MMUs and HOSPIRA MEDNET applications can be implemented locally at institutions, within remote institution data centers, and/or within remote vendor data centers 120'. In all of these potential implementations, the MMUs and HOSPIRA MEDNET applications are configured to gather, track, and store various configuration information and/or activity information. Referring to FIG. 1A, a multi-institutional/facility medical device configuration information and/or activity information gathering, comparing and reporting system 100 is shown, which assumes MMUs and HOSPIRA MEDNET applications are installed and running at a customer server 108, 108'. Specifically, multiple customer institutions/faculties, and medication delivery systems 108 therein are provided. As shown in FIGS. 1A, 1B and 2, and as will be described below, each customer institution can have multiple facilities, or a customer can have only one facility. Each customer institution and/or facility therein can have one or more separate and distinct medication delivery system, each system having one or more MMUs and a plurality of medical devices, such as medication delivery pumps, of the same or different types therein, typically provided by a vendor to the customer institution and/or facility. Each customer institution and/or facility can have a main server 108, 108' as a part of each institution and/or facility medication delivery system that is adapted to send configuration information/activity information for such customer institution, and/or facility to a central vendor or provider computer system 120, 120', such as at a vendor data center. Institution/facility configuration/activity information is tracked and updated on a continual basis at each institution/facility, through the MMUs and networked computers or servers.

In one embodiment, the central vendor/provider computer system 120, 120' can include an FTP server 124, 124' for receiving the configuration information/activity information from each customer institution/facility server 108, 108' therein. In the embodiment of FIG. 1A, a first firewall computer and/or first firewall application 128 can be provided within the central vendor/provider computer system in communication with the FTP server 124 for filtering traffic and allowing only valid configuration information/activity information to be received by the configuration/activity information aggregation server 132. As will be described below, each customer institution has its own account and a separate set of file folders within the FTP server 124, 124'. The central vendor/provider computer system 120, 120' can also have a configuration/activity information aggregation server or group of aggregation servers 132, 132' for hosting a configuration information/activity information aggregation application for aggregating or combining configuration information/activity information received from each individual customer server through the FTP server 124, 124'. Thus, when sent by the FTP server 124, 124' to the configuration/activity information aggregation server 132, 132' configuration information/activity information is communicated from the FTP server 124, 124' through the first firewall server/application 128 in FIG. 1A, to the configuration/activity information aggregation server 132, 132' for aggregation of the configuration information/activity information by the configuration/activity information aggregation server 132, 132'.

The central vendor/provider computer system or vendor data center 120, 120' can also have a configuration/activity information access server and/or cluster 136, 136' in communication with the configuration/activity information aggregation server 132, 132', for receiving aggregated configuration information/activity information, and for storing the aggregated configuration information/activity information within a multi-institutional configuration/activity information memory or central configuration/activity data repository 140, 140'. The repository or memory 140, 140' can be configured as a relational database for use by customer institutions/facilities, as will be described in greater detail below. A configuration/activity information application or central reporting application can reside and execute on the configuration/activity application server 136, 136' or web access server 160, 160' for allowing a customer access to the aggregated configuration information/activity information stored in the multi-institutional configuration/activity information repository 140, 140'. It should be understood that the multi-institutional configuration/activity information repository 140. 140' can be a single storage device 140, 140', such as a hard drive, or multiple storage devices 140, 140'. When the multiple storage devices 140, 140' are utilized, the information contained therein can be separated out into the separate storage devices 140, 140', such as one storage device 140, 140' comprising configuration information and another storage device comprising activity information. As described herein below, a BENCHMARKING software application, which in one embodiment is a part of the configuration/activity information application, and associated activity information, including analysis, reporting and/or other activity information can be provided. Likewise, an RXRULES software application, which is also known as HOSPIRA MEDNETMEDS, which in one embodiment is a part of the configuration/activity information application, and associated configuration information, including analysis, reporting, and other configuration information can be provided. In one embodiment, the activity information, including analysis, reporting and/or other activity information can be stored in one storage device 140, 140' and the configuration information, including analysis, reporting, and other configuration information can be stored in another, separate, storage device 140, 140'. Preferably, the configuration/activity information application will reside on the web access server 160, 160'.

The configuration/activity information application can include a database engine, such as SQL SERVER, for storing the configuration information/activity information in a relational structure within the repository 140, 140', and for use in responding to data requests for the relationally stored configuration information activity information. The central vendor/provider computer system 120, 120' can also have a web access server 160, 160' and a second firewall computer and/or second firewall application 170, 170' to receive requests and respond to requests from the customer institution/facility client computer 150, 150' to obtain access to the multi-institutional configuration/activity information repository 140, 140' and aggregated configuration information/activity information stored therein. The configuration/activity information application can also include a web user interface portion for generating interface screen displays, such as shown in FIGS. 4A-14 and other interface screen displays described below, by using a web browser on a remote client computer, such as the customer client computer 150, 150' or other client computer. The web user interface portion of the configuration/ activity information application can reside and execute on the web access server 160, 160'. It should be understood that the web access server 160, 160', the configuration/activity information access server 136, 136', the aggregation servers 132, 132', and/or the FTP server 124, 124', (as well as firewall systems), the various applications running therein, and the functions provided thereby may be combined in various combinations or distributed differently, and the present example is only one embodiment of how the present invention may be implemented.

Specifically, with reference again to FIG. 1B, an alternative arrangement is contemplated in view of a remote vendor data center 120' implementation of RHCSs 182, and described above. In such a vendor data center 120', in addition to using an FTP server 124, 124' shown in FIGS. 1A and 1B for receiving the configuration information/activity information from each customer institution/facility server 108, 108' therein, because the configuration information/activity information will already reside within the RHCSs 182 and respective RHCS databases 184, for each institution which has utilized the remote vendor data center services for hosting, such remote configuration information/activity information need only be extracted from the RHCSs 182 and respective RHCS databases 184. The configuration information/activity information is, thus, extracted from the RHCSs 182 and respective RHCS databases 184 into the configuration/activity information aggregation server 132' for aggregation of the configuration information/activity information by the configuration/activity information aggregation server 132'.

Aggregation may still be necessary in a remote vendor data center 120' environment when a separate physical or virtual server is used for each institution/facility. In a pure ASP environment described herein, when implemented in a the RHCS 182, if appropriate database tables are implemented similar to the database tables described herein, configuration/activity information aggregation can be extracted or called directly from the RHCS 182 and associated RHCS database 184 into the configuration/activity information access server 136', for use by a customer through a client computer 150' in a similar manner as described with respect to a customer using the remote customer client computer 150 described herein with respect to FIG. 1A, and other figures, for at least the functions provided by RXRULES and BENCHMARK applications described herein.

These remotely hosted vendor data center 120' embodiments can also be implemented with the embodiment of FIG. 1A. Specifically, as shown in FIG. 1B, FTP server 124', representing generally the FTP server 124 from FIG. 1A and having similar connections and functionality as described in relation to FIG. 1A for customer servers 108, can also send/FTP configuration information/activity information to configuration/activity information aggregation server 132' for aggregation of the configuration information/activity information by the configuration/activity information aggregation server 132', in addition to the configuration information/activity information being extracted from RHCS(s) 182 and associated RHCS database(s) 184 into configuration/activity information aggregation server 132'. Moreover, both extraction and FTP processes can take place at a predetermined time, such as at an off-peak usage time (during the middle of the night), simultaneously or at staggered times. In one embodiment, only after all configuration information/activity information is received from the FTP server 124' for all customers and respective customer servers 108, 108', and is received from RHCS(s) 182 and respective RHCS database(s) 184 for all customers using a vendor data center implementation, will the configuration/activity information aggregation server 132' execute an aggregation procedure, as described below with reference to FIG. 3.

When a customer institution/facility user is interested in obtaining access to the aggregated configuration information/activity information stored in the repository 140, 140', the user can access the web interface screen displays of the configuration/activity information application through the remote customer client computers 150, 150'. The web access server 160, 160' is in communication with configuration/activity information access or database server 136, 136', to receive and respond to requests from the remote institution client computer 150', 150' through which the configuration/activity information application can be utilized by the customer institution/facility user. Thus, in one embodiment, the configuration/activity application is a web application that is used to provide an online monitoring/reporting service for at least viewing and reporting on existing institutions and their respective configuration information/activity information for medical devices, such as for medication delivery pumps used within such institutions/facilities. The central vendor/provider computer system or data center 120, 120' and configuration/activity application therein can be hosted by an actual vendor of the medical devices, such as medication delivery pumps and/or medication delivery systems and/or portions thereof, to the customer institutions and facilities therein. Alternatively, the vendor/provider computer system 120, 120' and configuration/activity application therein can be hosted by a third party application service provider.

The multi-institutional medical device/medication delivery pump configuration information and/or activity information gathering, comparing and reporting system 100, 100' and the applications therein, can be implemented in software, firmware, hardware, or a combination thereof. In one mode, the multi-institutional medication delivery pump configuration information and/or activity information gathering, comparing and reporting system 100, 100' is implemented in software, as one or more executable programs or applications, and is executed by one or more special or general purpose digital computer(s), such as a personal computer (PC; IBM-compatible, APPLE-compatible, or otherwise), personal digital assistant, workstation, minicomputer, server, and/or mainframe computer. Therefore, the centralized computers 124, 124', 128, 128', 132, 132', 136 136', 160, 160', 170, 170', 180, and 182 of the central vendor/provider computer system or data center 120, 120', as well as the remote computers 108, 108', 150, and 150' of each customer institution, may be representative of any computers in which the applications of the multi-institutional configuration information and/or activity information gathering, comparing and reporting system 100, 100', and/or central vendor/provider computer system 120, 120', resides or partially resides.

Generally, in terms of hardware architecture, as shown in FIGS. 1 and 2, the computers 124, 124', 128, 128', 132, 132', 136 136', 160, 160', 170, 170', 180, and 182 of the central vendor/provider computer system 120, 120', as well as the remote computers 108, 108', 150, and 150', include a processor, memory, and one or more input and/or output (I/O) devices (or peripherals) that are communicatively coupled via a local interface. The local interface can be, for example, but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the other computer components.

The processors are hardware devices for executing software, particularly software stored in memory. The processors can be any custom made or commercially available processor, a central processing unit (CPU), an auxiliary processor among several processors associated with the computers 124, 124', 128, 128', 132, 132', 136', 160, 160', 170, 170', 180, and 182 of the central vendor/provider computer system 120, 120', as well as the remote computers 108, 108', 150, and 150', a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc., or a 68xxx series microprocessor from Motorola Corporation. The processors may also represent a distributed processing architecture such as, but not limited to, EJB, CORBA, and DCOM. In one embodiment, the FTP server 124 is a WINDOWS based server or series of servers, the configuration information/activity information aggregation server 132 is a WINDOWS based server or series of servers, the configuration information/activity information access server 136 is a WINDOWS based server or series of servers hosting MICROSOFT SQL SERVER, and the web access server 160 is a WINDOWS based server or series of servers.

Each memory of each computer 124, 124', 128, 128', 132, 132', 136', 160, 160', 170, 170', 180, and 182 of the central vendor/provider computer system 120, 120' as well as the remote computers 108, 108', 150, and 150', as well as the multi-institutional configuration/activity information memory or central configuration/activity data repository 140, 140' can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, these memories may incorporate electronic, magnetic, optical, and/or other types of storage media. The memories can have a distributed architecture where various components are situated remote from one another, but are still accessed by the processors of the computers 124, 124', 128, 128', 132, 132', 136', 160, 160', 170, 170', 180, and 182 of the central vendor/provider computer system 120, 120', as well as the remote computers 108, 108', 150, and 150'.

The software within one or more of the above referenced memories may include one or more separate programs. The separate programs comprise ordered listings of executable instructions for implementing logical functions. In the examples of FIGS. 1 and 2, the software in the memories includes suitable operating systems (O/S). A non-exhaustive list of examples of suitable commercially available operating systems is as follows: (a) a WINDOWS operating system available from Microsoft Corporation; (b) a NETWARE operating system available from Novell, Inc.; (c) a MACINTOSH operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time VXWORKS operating system from WindRiver Systems, Inc.; or (g) an appliance-based operating system, such as that implemented in handheld computers or personal digital assistants (PDAs) (e.g., PalmOS™ available from Palm Computing, Inc., and WINDOWS CE available from Microsoft Corporation). The operating systems essentially control the execution of other computer programs, such as the configuration/activity information aggregation application and/or the configuration information application, in accordance with the present invention, and provide scheduling, input-output control, file and data management, memory management, and communication control and related services.

The configuration/activity information aggregation application and/or the configuration information application, and other source programs within the multi-institutional configuration information and/or activity information gathering, comparing and reporting system 100, 100' and/or central vendor/provider computer system 120, 120' may be a source program, executable program (object code), script, or any other entity comprising a set of instructions to be performed. When a source program, the program needs to be translated via a compiler, assembler, interpreter, or the like, which may or may not be included within the memories, so as to operate properly in connection with the O/S. Furthermore, these applications can be written as (a) an object oriented programming language, which has classes of data and methods, or (b) a procedural programming language, which has routines, subroutines, and/or functions, for example but not limited to, VB.Net, C#, C, C++, Pascal, Basic, Fortran, Cobol, Perl, Java, and Ada. In one embodiment, the configuration/activity information aggregation application is written in VB.Net and the configuration information application is written in T-SQL.

The I/O devices referred to above may include input devices, for example input modules for PLCs, a keyboard, mouse, scanner, microphone, touch screens, interfaces for various medical devices, bar code readers, stylus, laser readers, radio-frequency device readers, etc. Furthermore, the I/O devices may also include output devices, for example but not limited to, output modules for PLCs, a printer, bar code printers, displays, etc. Finally, the I/O devices may further include devices that communicate both inputs and outputs, for instance but not limited to, a modulator/demodulator (modem; for accessing another device, system, or network), a radio frequency (RF) or other transceiver, a telephonic interface, a bridge, and a router.

If the computers 124, 124', 128, 128', 132, 132', 136', 160, 160', 170, 170', 180, and 182 of the central vendor/provider computer system 120, 120' as well as the remote computers 108, 108', 150, and 150', are a PC, workstation, PDA, or the like, the software in the respective memories may further include a basic input output system (BIOS) (not shown in FIGS. 1 and 2). The BIOS is a set of essential software routines that initialize and test hardware at startup, start the O/S, and support the transfer of data among the hardware devices. The BIOS is stored in ROM so that the BIOS can be executed when computers 124, 124', 128, 128', 132, 132', 136', 160, 160', 170, 170', 180, and 182 of the central vendor/ provider computer system 120, 120' as well as the remote computers 108, 108', 150, and 150' are activated.

When the computers 124, 124', 128, 128', 132, 132', 136', 160, 160', 170, 170', 180, and 182 of the central vendor/ provider computer system 120, 120', as well as the remote computers 108, 108', 150, and 150', are in operation, the processors therein are configured to execute software stored within respective memories, to communicate data to and from memories, and to generally control operations of the computers 124, 124', 128, 128', 132, 132', 136', 160, 160', 170, 170', 180, and 182 of the central vendor/provider computer system 120, 120', as well as the remote computers 108, 108', 150, and 150', pursuant to the software. The configuration/activity information aggregation application and the configuration information applications, and the O/S, in whole or in part, but typically the latter, are read by respective processors, perhaps buffered within the processors, and then executed.

When the multi-institutional medical device configuration information and/or activity information gathering, comparing and reporting system 100 and/or the central vendor/provider computer system 120, 120' are implemented in software, as is shown in FIGS. 1 and 2, it should be noted that the application programs therein can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The application programs, such as the configuration/activity information aggregation application and the configuration information application can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

In another embodiment, where the multi-institutional medical device configuration information and/or activity information gathering, comparing and reporting system 100, 100' and/or the central vendor/provider computer system 120, 120' are implemented in hardware, these systems can be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

In the context of medication management units (MMUs), a remote institution/facility user of the system through the client computer 150, 150' can see at least "peer" institution pump configuration and activity information, including but not limited to "peer" institution configuration libraries such as drug libraries used in medication delivery pumps or infusers. The institutions/facilities can use this information as a setup guide for their own institutions/facilities, and/or can directly use at least portions of the configuration libraries to define the clinical care areas and configuration libraries. The central configuration/activity data repository 140 and database therein, includes many database files and/or tables for storing and recalling of configuration/activity information about the customer institutions, facilities, and infusers in each facility as well as other information.

For each such existing customer institution and/or related facilities or standalone facility, the configuration information and/or activity information is aggregated at a main server at each institution/facility. A FTP program can be installed and run on the main server at each institution/facility, and the FTP program can be adapted to gather and send the configuration information and/or activity information, to the central FTP server 124, 124'. In one embodiment, the files can be sent in a flat file format, which includes all configuration information and/or activity information residing within the institution. In particular, referring again to FIG. 2, a first main server 200, or customer institution server 108, 108' from FIGS. 1A and 1B, within a medication management system of a first institution is in communication with a first facility server 204 within a medication management system of a first facility, a second facility server 208 within a medication management system of a second facility, and a third facility server 212 within a medication management system of a third facility, all a part of the first institution and medication management system therein. First facility medical devices, such as medication delivery pumps or infusers A, B, C are in communication with the first facility server 204, second facility medical devices such as medication delivery pumps D, E, F are in communication with second facility server 208, and third facility medical devices such as medication delivery pumps G, H are in communication with the third facility server 212. All of the configuration information and activity information related to the configuration and operation of the devices/pumps is received and/or stored at the first, second and third facility servers 204, 208, 212 and aggregated at the first main server 200 for the first institution. The FTP program residing on the first main server 200 sends the most up to date configuration information and activity information relating to the configuration and operation of the medical devices/medication delivery pumps within the first institution to the central FTP server 124.

Likewise, a second main server 216, or customer institution server 108 from FIG. 1A, within a medication management system of a second institution is in communication with a first facility server 220 within a medication management system of a first facility and a second facility server 224 within a medication management system of a second facility, both a part of the second institution and medication management system therein. First facility medical devices such as medication delivery pumps or infusers I, J are in communication with the first facility server 220 and a second facility medical devices such as medication delivery pump K is in communication with second facility server 224. All of the configuration information and activity information related to the configuration and operation of the pumps is received and/or stored at the first and second facility servers 220, 224 and aggregated at the second main server 216 for the second institution. The FTP program residing on the second main server 216 sends the most up to date configuration information and activity information relating to the configuration and operation of the medical devices/medication delivery pumps within the second institution to the central FTP server 124. In one embodiment, it should be understood that the first and second main servers 200, 216 can be considered as facility servers instead of main institution servers, and can directly communicate with and send FTP configuration information and/or activity information to the central FTP server 124, 124' from each facility instead of going through a main institution server. The configuration of the configuration information/activity information application allows for the facilities and the configuration information and/activity information received therefrom to be assigned to and associated with an institution within the central vendor/provider computer system 120, 120'. Likewise, the facility servers 204, 208, 212, 220, 224 can be medication management units (MMUs) as described above, and can report the configuration information and/or activity information to each respective facility server 200, 216 for FTP processing of such information along to the central FTP server 124, 124'. In an embodiment where there is a stand alone or single facility in an institution, a single server will likely be used, connected to multiple MMUs, and the single server will perform the FTP functions for sending the configuration/activity information along to the FTP server 124, 124'.

Likewise, a third main server 230, or customer institution server 108 from FIG. 1A, within a medication management system of a third institution where there is only one facility or first facility server 230 within the medication management system of the institution. Medical devices such as medication delivery pumps or infusers L, M, N, O are in communication with the first facility server. All of the configuration information and activity information related to the configuration and operation of the pumps is received and/or stored at the first facility server 230 and aggregated at this server for the third institution. The FTP program residing on the third main server 230 sends the most up to date configuration information and activity information relating to the configuration and operation of the medical devices/medication delivery pumps within the third institution to the central FTP server 124, 124'. The configuration of the configuration information/activity information application allows for the facilities and the configuration information and/activity information received therefrom to be assigned to and associated with an institution within the central vendor/provider computer system 120, 120'.

As will be described below, institutions, such as hospitals have customer identifiers (IDs) and server identifiers (IDs), and the files which are transferred from an institution server 200, 216 to the central server 124, 124' each can use the customer identifier and server identifier to allow the central FTP server 124, 124' to map and associate the received files with the correct customer institution. In addition, each infuser has an infuser ID and the configuration/activity information for a particular infuser can be associated with the infuser ID. Each infuser can be tied to a location where the infuser is located and communicating. This location can be used to match with location descriptions assigned by each institution by the administrator, as will be understood from the below description. As each institution's information passes into the configuration/activity information aggregation server 132, 132', the server 132, 132' will match the location description of each infuser within each file that is received with the location description assigned by the administrator within the configuration information/activity information application.

As mentioned, an FTP program can be installed within the medication delivery computer at each institution and/or facility, and can run on daily or some other predetermined time interval basis to extract the configuration information and activity information in a file format, and FTP the files to the central FTP server 124, 124'. Another application on the configuration/activity information aggregation server 132, 132' on daily or some other predetermined time interval basis receives the already FTPed configuration information and activity information files from the central FTP server 124, 124', and pushes the aggregated configuration information and activity information, and other information into the configuration information/activity information database within repository 140, 140'. In one embodiment described in relation to FIG. 1B herein, when RHCSs are implemented in an ASP environment, the structure identified in FIG. 2 can be used to structure the ASP database or RHCS database 184. Specifically, institution and facility identifiers can be used to identify respective configuration information/activity information from such institutions and facilities, stored within the RHCS database 184. Likewise, when each RHCS is implemented in separate physical or virtual server, the structure identified in FIG. 2 can be used to structure the RHCS databases 184. Specifically, institution and facility identifiers can be used to identify respective configuration information/activity information from such institutions and facilities, stored within the RHCS databases 184.

Figure 3:
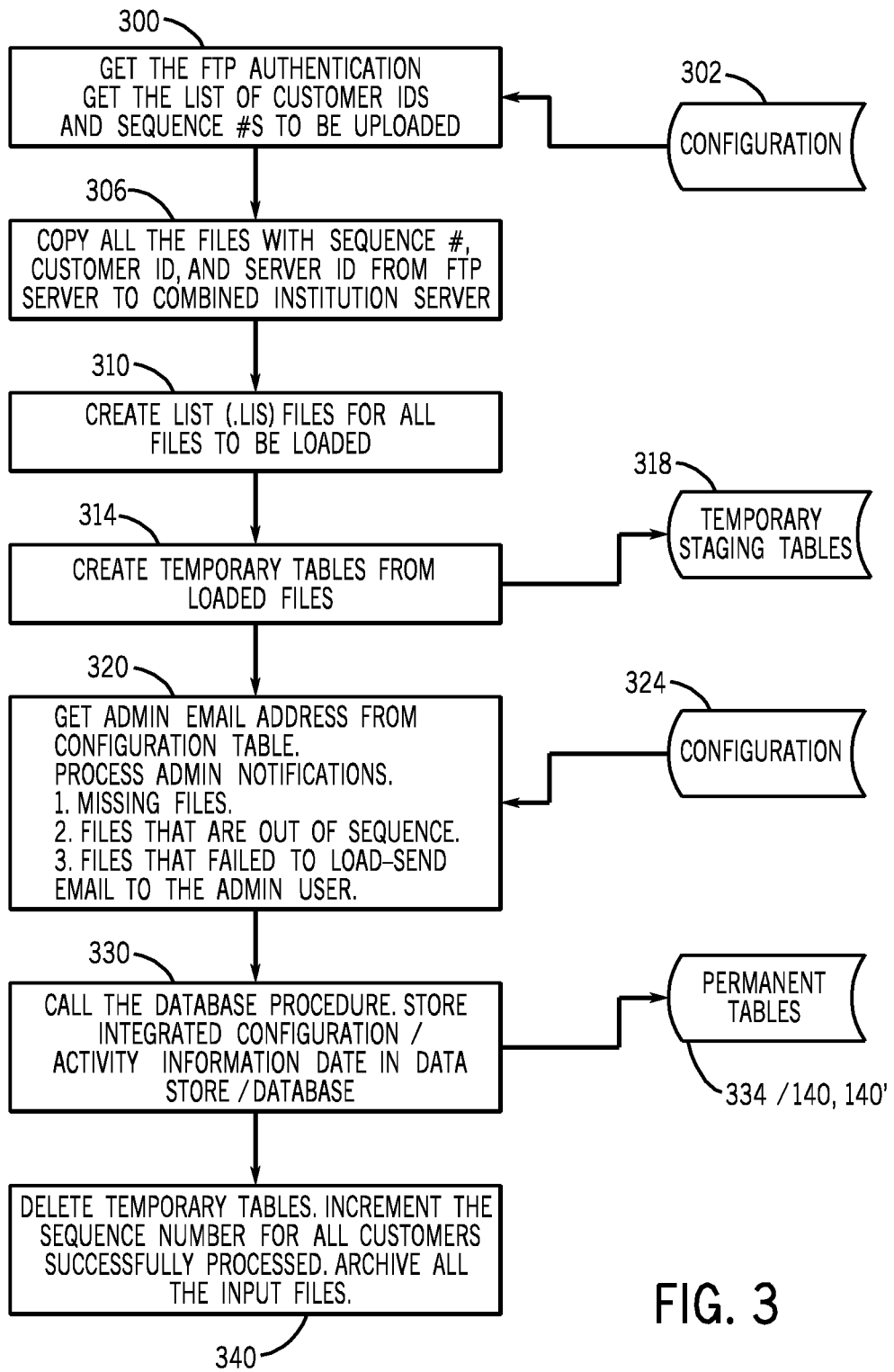
FIG. 3 is a flow chart of a multi-institutional data integration process of the present invention.

Referring to FIG. 3, a flow chart of the configuration information and activity information extracting process is shown for at least the FTP process related to FIG. 1A. Specifically, a first step 300 includes making sure the files being received and/or the servers are authenticated and from a valid institution. This is accomplished by obtaining configuration details 302 such as all of the customer IDs of the institutions for which information has been received or for which the aggregation process should include. This task can be triggered based on a predetermined time, time interval or the satisfaction of some condition that is selected by an administrator. This task can also be triggered on the customer side or on the vendor/provider side for pushing or pulling information respectively. A second step 306 includes copying all of the files having a particular sequence number, customer number, and server ID number from the FTP server 124 to the configuration/activity information aggregation server 132. A similar step of steps could be implemented for configuration information/activity information extracted from the RHCS database(s) 184, related to FIG. 1B. A third step 310 includes creating .lis files for use in the aggregation process. A fourth step 314 includes creating temporary "staging" files 318, as provided below, from the loaded files. A fifth step 320 includes obtaining additional configuration details 324 such as an administrator's e-mail (an administrator is a user having "administrator" or the highest level access to the configuration information/activity information application at an institution; a vendor administrator has the highest level of authority for the entire software application), and processing any administrator notifications, such as that some files are missing from the FTP/extraction process, some files are out of sequence from the FTP/extraction process, and/or that some files failed to load from the FTP server and/or RHCS database 184 and RHCS server 182. A sixth step 330 includes running the configuration information/activity information aggregation application database procedure to populate the permanent database tables 334 within the central configuration/activity data repository 140. A seventh step 340 includes deleting the temporary tables and incrementing the sequence number for all successfully processed customer institution configuration information and activity information files. All input files from the configuration/activity information aggregation server 132 are then archived for a period of time within the configuration/activity information aggregation server 132, as provided herein.

As a part of the extraction/file transfer process, the systems 120, 120' can be configured to include additional steps as follows: the FTP server 124, 124', front end server 180 or other server can be configured to automatically generate a reminder, such as by sending an e-mail reminder, to remind the customer to manually upload their drug libraries from the medical devices into the customer server 108, 108', used to extract/FTP configuration/activity data from. In some settings, this is a useful and potentially necessary action to obtain current configuration/activity information, as some "hard wired" medical devices into the network of devices must be manually controlled to cause uploads of configuration/activity information into the customer server 108, 108' to occur. In addition, a generic names cleanup routine can be performed to make sure that generic names used within the configuration/activity information databases 108, 108' at each institution match the generic names used within the configuration/activity information database 140, 140'. This routine can be run at each institution prior to data extraction or transfer or can be run within the central vendor/provider computer system 120, 120'. Particular rules are used to ensure that data is properly matched can be implemented, such as generic names shall not contain dosage amounts; generic names shall be in lower case; generic names shall not contain a display name. With respect to use of this generic name data cleaning functionality through central vendor/provider computer system 120, 120', the system will attempt to match the user's configuration information, such as drug library entries to a generic entry for drugs when importing configuration information into the system 120, 120' and/or exporting configuration information from the system 120, 120'. The system 120, 120' can be configured to automatically identify common generic names and common generic name errors. The system can be configured to allow a user to establish a common generic name errors table for entering into such table common generic name errors for automatically mapping such errors onto the correct generic name in the automated cleaning process. During the automated cleaning process, if a generic name error cannot be found in a mapping table, then system will add or write such unfound error into an error file for later review by an administrator (vendor or customer). This and other generic name cleaning processes can be integrated into the shopping cart functionality described herein.

In one embodiment, the following file format names can be used: <customerID>_<serverID>_<timestamp>_<sequence number>_<type of file>.txt. Various checks can be done to ensure that correct files are being received by the aggregation server 132 and aggregation application therein. First, the aggregation application can make sure that the FTP server received the correct files by checking the customer ID and server ID for each file. Next, the aggregation application can make sure that no file is missed. This is accomplished on the aggregation server by extracting the sequence number stored inside the file itself, and verifying the number is in sequence. The processing will fail if any of the files come out of sequence. A central or vendor administrator at the vendor location can be provided with the ability to notify the subject institution, if needed, as will be explained below within the description of the administrator maintenance interface screens.

In one embodiment of the aggregation process, a user type table is generated to store the user types within the database 140. The following table provides an example of some of the details of what can be stored in this table:

| Column Name | Description | Data Type |
| --- | --- | --- |
| USER_TYP_ID | User Type id—identity column starts with 1 and incremented by 1. | NUMERIC |
| USER_TYP_NAME | Name of the user type to be displayed in the drop down. | VARCHAR |
| USER_TYP_DESC | Description for the user type | VARCHAR |
| IS_ACTIVE | Whether the user type is active or not (Y—Active, N—Inactive) | CHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a user profile table is generated to store the user profiles within the database 140. The following table provides an example of some of the details of what can be stored in this table:

| Column Name | Description | Data Type |
| --- | --- | --- |
| USER_ID | User ID—identity column starts with 100000 and incremented by 1. | NUMERIC |
| FIRST_NAME | First Name of the user | VARCHAR |
| LAST_NAME | Last Name of the user | VARCHAR |
| IS_ACTIVE | Whether the user is active or not (Y—Active, N—Inactive) | CHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| TITLE | Title (like Mr, Ms, Dr, Prof etc.) | VARCHAR |
| MID_NAME | Middle Name of the user | VARCHAR |
| SUFFIX | Suffix for the user name like I, II, Jr, Sr, etc. | VARCHAR |
| ADDR1 | Address | VARCHAR |
| ADDR2 | Address line 2 | VARCHAR |
| CITY | City | VARCHAR |
| STATE_ID | State ID | VARCHAR |
| ZIP | Zip code | VARCHAR |
| COUNTRY | Country | VARCHAR |
| CELL_PHONE | Cell Phone | VARCHAR |
| WORK_PHONE | Work Phone | VARCHAR |
| FAX | Fax | VARCHAR |
| EMAIL_ADDR | Email Address | VARCHAR |
| USER_TYP_ID | User Type ID | NUMERIC |
| REG_DATE | Registered date | DATETIME |
| ACCESS_TYPE | Access Type (Trial/Extended/Expired) | CHAR |
| BM_EXPIRY_DT | BenchMark Expiry Date. If null, user is not allowed at all times. | DATETIME |
| RX_EXPIRY_DT | RxRules Expiry Date. If null, user is not allowed at all times. | DATETIME |
| LAST_LOGIN_DTTM | Last Login Date Time | DATETIME |
| PREV_LOGIN_DTTM | Previous Login Date Time | DATETIME |
| PASSWORD | Password | VARCHAR |
| PASSWORD_EXPIRY_DT | Password Expiry Date | DATETIME |
| SEC_QN_CD | Secret Question Code-available in lookup table. | VARCHAR |
| SEC_QN_ANS | Secret Question Answer. | VARCHAR |
| ACC_LOCKED | Whether the account is locked or not | CHAR |
| ADDL_INFO | Additional Information | VARCHAR |
| SHIPTO_ID | Ship to ID | VARCHAR |
| PREF_PEERGROUP_TYPE | Preferred Peer Group Type ID | NUMERIC |
| PREF_PEERGROUP_SIZE | Preferred Peer Group Size ID | NUMERIC |
| PREF_DEVICETYPE | Preferred Device Type ID | NUMERIC |

| Column Name | Description | Data Type |
| --- | --- | --- |
| PREF_DISPLAY | Preferred Display (1 for Display by Month, 2 for Display by Quarter) | CHAR |

In one embodiment of the aggregation process, a track user usage table is generated to store the history of user interaction with the system. This is stored within the database 140. The following table provides an example of some of the details of what can be stored in this table:

| Column Name | Description | Data Type |
| --- | --- | --- |
| USER_USAGE_ID | User Usage ID | NUMERIC |
| USER_ID | User ID | NUMERIC |
| ADD_DT | Added date | DATETIME |
| ADD_BY | Added by | VARCHAR |
| ADD_PRGM | Added program | VARCHAR |
| ACTION | Specific action like Login Benchmark Report RxRules report Password Expiry Password Reset Account locked out | VARCHAR |
| ACTION_DT | Datetime the action happened. | DATETIME |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a user history table is generated to store all user profile changes within the database 140. The following table provides an example of some of the details of what can be stored in this table:

| Column Name | Description | Data Type |
| --- | --- | --- |
| USER_HISTORY_ID | History ID | NUMERIC |
| USER_ID | User ID | NUMERIC |
| COLUMNNAME | Column Name | VARCHAR |
| ADD_DT | Added date | DATETIME |
| ADD_BY | Added by | VARCHAR |
| ADD_PRGM | Added program | VARCHAR |
| OLDVALUE | Old Value | VARCHAR |
| NEWVALUE | New Value | VARCHAR |
| ACTION_DESC | Action Performed | VARCHAR |

In one embodiment of the aggregation process, a health system detail table is generated to store a health system details within the database 140. The following table provides an example of some of the details of what can be stored in this table:

| Column Name | Description | Data Type |
| --- | --- | --- |
| HEALTHSYSTEM_ID | HealthSystem ID—identity column starts with 1 and incremented by 1. | NUMERIC |
| IS_ACTIVE | Whether the HealthSystem is active or not (Y—Active, N—Inactive). | CHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| CUSTOMERID | Customer ID | NUMERIC |
| AHA_NMBR | AHA Number | VARCHAR |
| HIN_NMBR | HIN Number | NUMERIC |
| NAME | Name of the HealthSystem. | VARCHAR |
| ADDR | Address | VARCHAR |
| CITY | City | VARCHAR |
| STATE | State | VARCHAR |
| ZIP | Zip | VARCHAR |
| COUNTRY | Country | VARCHAR |
| PHONE_NO | Phone Number | VARCHAR |
| EMAIL_ADDR | Email Address | VARCHAR |
| CNTT_NAME | Contact Name | VARCHAR |
| CMI | Case Mix Index | VARCHAR |
| REG_DATE | Registered Date | DATETIME |
| PEER_GROUP_ID | Peer Group ID | NUMERIC |
| TYPE_ID | Peer Group Type | NUMERIC |
| NO_OF_BEDS | No. of Beds in the HealthSystem (Sum of beds in the Facilities) | NUMERIC |

In one embodiment of the aggregation process, a facility detail table is generated to store the facility detail within the database 140. The following table provides an example of some of the details of what can be stored in this table:

| Column Name | Description | Data Type |
| --- | --- | --- |
| FCLTY_ID | Facility ID—identity column starts with 1 and incremented by 1. | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| PEER_GROUP_ID | Peer Group ID | NUMERIC |
| LOCATION_DESCRIPTOR | Location Descriptor | CHAR |
| HIN_ID | HIN ID | NUMERIC |
| AHA_NMBR | AHA Number | NUMERIC |
| NAME | Name of the Facility. | VARCHAR |
| ADDR | Address | VARCHAR |
| CITY | City | VARCHAR |
| STATE | State | VARCHAR |
| ZIP | Zip | VARCHAR |
| COUNTRY | Country | VARCHAR |
| PHONE_NO | Phone Number | VARCHAR |
| EMAIL_ADDR | Email Address | VARCHAR |
| PARENT_HEALTHSYSTEM_ID | Parent HealthSystem ID | NUMERIC |
| SERVERID | Server ID | NUMERIC |
| TYPE_ID | Peer Group Type ID | NUMERIC |
| NO_OF_BEDS | No of Beds in the Facility | NUMERIC |
| REG_DATE | Registered Date | DATETIME |
| IS_ACTIVE | Whether the facility is still active or not (Y—Active, N—Inactive). | CHAR |
| FCLTY_ACCESS_TYPE | Facility Access Type | NUMERIC |

In one embodiment of the aggregation process, a user health system facility detail table is generated to store the user/health system/facility mapping within the database 140. The following table provides an example of some of the details of what can be stored in this table:

| Column Name | Description | Data Type |
| --- | --- | --- |
| USER_ID | User ID | NUMERIC |
| HEALTHSYSTEM_FACILITY_ID | Health System Facility ID | NUMERIC |

| Column Name | Description | Data Type |
| --- | --- | --- |
| HEALTHSYSTEM_FCLTY | HealthSystem or Facility (S—HealthSystem, F—Facility) | CHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a user health system server detail table is generated to store the health system server detail within the database 140. The following table provides an example of some of the details of what can be stored in this table:

| Column Name | Description | Data Type |
| --- | --- | --- |
| HEALTHSYSTEM_ID | HealthSystem ID | NUMERIC |
| SERVER_ID | Server ID | NUMERIC |
| SERVER_DESC | Server Description | VARCHAR |
| BM_FTP_NO | BenchMark FTP Number | NUMERIC |
| RX_FTP_NO | RxRules FTP Number | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a peer group master table is generated to store the peer group definitions within the database 140. The following table provides an example of some of the details of what can be stored in this table:

| Column Name | Description | Data Type |
| --- | --- | --- |
| PEER_GROUP_ID | Peer Group ID—Identity column start with 1 and incremented by 1. | NUMERIC |
| TYPE_ID | Peer Group Type ID | NUMERIC |
| SIZE_ID | Peer Group Size ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a peer group type table is generated to store the peer group types within the database 140. The following table provides an example of some of the details of what can be stored in this table:

| Column Name | Description | Data Type |
| --- | --- | --- |
| TYPE_ID | Peer Group Type ID—Identity column start with 1 and incremented by 1. | NUMERIC |
| IS_ACTIVE | Is the peer group Type active or not (Y—Active, N—Inactive)? | CHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| TYPE_NAME | Peer Group Type Name | VARCHAR |
| TYPE_DESC | Peer Group Type Description | VARCHAR |

In one embodiment of the aggregation process, a peer group size table is generated to store the peer group sizes within the database 140. The following table provides an example of some of the details of what can be stored in this table:

| Column Name | Description | Data Type |
| --- | --- | --- |
| SIZE_ID | Peer Group Size ID— Identity column start with 1 and incremented by 1. | NUMERIC |
| SIZE_NAME | Peer Group Size Name | VARCHAR |
| IS_ACTIVE | Is the peer group Size active or not (Y—Active, N—Inactive)? | CHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| SIZE_DESC | Peer Group Size Description | VARCHAR |
| LOW_VALUE | Peer Group Low Limit for No. of Beds | NUMERIC |
| HIGH_VALUE | Peer Group High Limit for No. of Beds | NUMERIC |

In one embodiment of the aggregation process, a general parameter table is generated to store general parameters within the database 140, as will be understood from at least the administrator interface screen description below. The following table provides an example of some of the details of what can be stored in this table:

| Column Name | Description | Data Type |
| --- | --- | --- |
| PARM_ID | Parameter ID—Identity column start with 1 and incremented by 1. | NUMBER |
| PARM_NAME | Parameter Name | VARCHAR |
| PARM_DESC | Parameter Description | VARCHAR |
| PARM_TYPE | Parameter Value | VARCHAR |
| PARM_VALUE | Parameter Value | VARCHAR |
| IS_ACTIVE | Is the configuration parameter is active or not (Y—Active, N—Inactive)? | CHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a "benchmark" or activity information summary table is generated to store summary results of activity information within the database 140. The following table provides an example of some of the details of what can be stored in this table:

| Column Name | Description | Data Type |
| --- | --- | --- |
| BENCHMARK_ID | BenchMark ID | NUMERIC |
| DISP_YEAR | Display Year Number | NUMERIC |
| DISP_MONTH | Display Month Number | NUMERIC |
| CHART_TYPE | Chart Type | VARCHAR |
| CHART_ID | Chart ID | NUMERIC |
| DEVICETYPEID | DeviceType ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| SERVERID | Server ID | NUMERIC |
| CUSTOMERID | Customer ID | NUMERIC |
| PEER_GRP | Peer Group ID | NUMERIC |
| SYSTEM_ID | Health System ID | NUMERIC |
| FCLTY_ID | Facility ID | NUMERIC |
| GRP_NAME | Group Name—Data Point Name | VARCHAR |
| GRP_VALUE | Value for the group | NUMERIC |

In one embodiment of the aggregation process, an asset location table is generated to store institutional asset location information within the database 140. The following table provides an example of some of the details of what can be stored in this table:

| Column Name | Description | Data Type |
| --- | --- | --- |
| SERVERID | Server ID | NUMERIC |
| CUSTOMERID | Customer ID | NUMERIC |
| ASSETLOCATIONID | Asset Location ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| LOCATIONID | Location ID | VARCHAR |
| LOCATIONDESCRIPTOR | Location Descriptor | VARCHAR |

In one embodiment of the aggregation process, an asset table is generated to store institutional asset information within the database 140. The following table provides an example of some of the details of what can be stored in this table:

| Column Name | Description | Data Type |
| --- | --- | --- |
| SERVERID | Server ID | NUMERIC |
| CUSTOMERID | Customer ID | NUMERIC |
| ASSETID | Asset Id | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| LOGICALID | Logical ID | VARCHAR |
| LOCATIONTIME | Location Time | DATETIME |
| ASSETLOCATIONID | Asset Location ID | NUMERIC |
| ASSETTYPEID | Asset Type ID | NUMERIC |
| IPADDRESS | IP Address | VARCHAR |

In one embodiment of the aggregation process, a device table is generated to store the infusers/pumps associated to a server within the database 140. The following table provides an example of some of the details of what can be stored in this table:

| Column Name | Description | Data Type |
| --- | --- | --- |
| SERVERID | Server ID | NUMERIC |
| CUSTOMERID | Cutomer Id | NUMERIC |
| DEVICEID | Device ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| FCLTY_ID | Facility ID | NUMERIC |
| ASSETID | Asset ID | NUMERIC |
| COMPARTMENTINDEX | Compartment Index | NUMERIC |
| CCANAMEID | CCA Name ID | NUMERIC |
| DEVICETYPEID | Device Type ID | NUMERIC |
| DOWNLOADSTATEID | Download State ID | NUMERIC |
| PREVIOUSDOWNLOADSTATE | Previous Download State ID | NUMERIC |
| CURRENTDRUGLIBRARYID | Current Drug Library ID | NUMERIC |
| DEVICESTATEID | Device State ID | NUMERIC |
| INVENTORYSTATUS | Inventory Status | VARCHAR |
| DELETED | Deleted Flag | CHAR |
| DATEDELETED | Date Deleted | DATETIME |
| LASTLOGUPLOAD | Last Log Upload | DATETIME |
| CURRENTDRUGLIBRARYNAME | Current Drug Library Name | VARCHAR |

In one embodiment of the aggregation process, an event type table is generated to store the types of events, such as an "alarm" type of event, within the database 140. The following table provides an example of some of the details of what can be stored in this table:

| Column Name | Description | Data Type |
| --- | --- | --- |
| SERVERID | Server ID | NUMERIC |
| CUSTOMERID | Customer ID | NUMERIC |
| EVENTTYPEID | Event Type Id | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| NAME | Name | VARCHAR |
| DEVICETYPEID | Device Type ID | NUMERIC |
| LOGFORMAT | Log Format | VARCHAR |
| DESCRIPTION | Description | VARCHAR |
| STOREPARAMETERS | Store Parameters | BIT |

In one embodiment of the aggregation process, an event log table is generated to store a log of the infuser activity within the database 140. The following table provides an example of some of the details of what can be stored in this table:

| Column Name | Description | Data Type |
| --- | --- | --- |
| SERVERID | Server ID | NUMERIC |
| CUSTOMERID | Customer ID | NUMERIC |
| EVENTID | Event ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| YEARMONTHDAY | Year Month Day | VARCHAR |
| EVENTTYPEID | Event Type ID | NUMERIC |
| EVENTTIME | Event Time | DATETIME |

-continued

| Column Name | Description | Data Type |
| --- | --- | --- |
| RAWDATA | Raw Data | VARCHAR |
| DEVICEID | Device ID | NUMERIC |
| PRIMARYCATEGORYID | Primary Category ID | NUMERIC |
| LOGINDEX | Log Index | NUMERIC |
| LOGTIME | Log Time | DATETIME |
| DEVICETYPEID | Device Type ID | VARCHAR |
| CCANAME | CCA Name | VARCHAR |
| DATAFROMDEVICE | Data from Device | VARCHAR |

In one embodiment of the aggregation process, an event parameter data table is generated to store the parameter data for the events within the database 140. The following table provides an example of some of the details of what can be stored in this table:

| Column Name | Description | Data Type |
| --- | --- | --- |
| SERVERID | Server ID | NUMERIC |
| CUSTOMERID | Customer ID | NUMERIC |
| EVENTPARAMETERDATAID | Event Parameter Data ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| YEARMONTHDAY | Year Month Day in YYYYMMDD format. | VARCHAR |
| EVENTID | Event ID | NUMERIC |
| EVENTPARAMERTYPEID | Event Parameter Type ID | NUMERIC |
| PARAMVALUE | Parameter Value | VARCHAR |

In one embodiment of the aggregation process, an event parameter type table is generated to store the types of event parameters within the database 140. The following table provides an example of some of the details of what can be stored in this table:

| Column Name | Description | Data Type |
| --- | --- | --- |
| SERVERID | Server ID | NUMERIC |
| CUSTOMERID | Customer ID | NUMERIC |
| EVENTPARAMETERTYPEID | Event Parameter Type ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| PARAMNAME | Parameter Name | VARCHAR |
| PARAMTYPENAMEID | Parameter Type Name ID | NUMERIC |
| PARAMDISPLAYFORMAT | Parameter Display Format | VARCHAR |

In one embodiment of the aggregation process, a generic medication or configuration table is generated to store the generic configuration data, such as generic drug data, within the database 140. This table can be built from the input data in the configuration library. The following table provides an example of some of the details of what can be stored in this table:

| Column Name | Description | Data Type |
| --- | --- | --- |
| GENERICDRUGID | Generic Drug ID | NUMERIC |
| SERVERID | Server ID | NUMERIC |
| GENERICNAME | Generic Name | VARCHAR |

-continued

| Column Name | Description | Data Type |
| --- | --- | --- |
| CUSTOMERID | Customer ID | NUMERIC |
| DEVICETYPEID | Device Type ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a service line table is generated to store the service line identifiers and descriptions within the database 140. This table can also be built from the input data in the configuration library. The following table provides an example of some of the details of what can be stored in this table:

| Column Name | Description | Data Type |
| --- | --- | --- |
| SERVICELINEID | Service Line ID | NUMERIC |
| SERVERID | Server ID | NUMERIC |
| CUSTOMERID | Customer ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| SERVICELINEDESC | Service Line Description | VARCHAR |

In one embodiment of the aggregation process, a clinical care area (CCA) detail table is generated to store the clinical care areas mapped to service lines within the database 140. This table can also be built from the input data in the configuration library. The following table provides an example of some of the details of what can be stored in this table:

| Column Name | Description | Data Type |
| --- | --- | --- |
| CCA_ID | CCA ID | NUMERIC |
| SERVICELINEID | Service Line ID | NUMERIC |
| CCANAME | CCA Name | VARCHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a device type table is generated to store the types of devices within the database 140. This table can also be built from the input data in the configuration library. The following table provides an example of some of the details of what can be stored in this table:

| Column Name | Description | Data Type |
| --- | --- | --- |
| DEVICE_TYPE_ID | Device Type ID | NUMERIC |
| DEVICE_TYPE_DESC | Device Type Description | VARCHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |

In one embodiment of the aggregation process, a configuration library table is generated to store the generic drug/service line/CCA mapping of configuration libraries from each institution within the database 140. The following table provides the example of some of the details of what can be stored in this table:

| Column Name | Description | Data Type |
| --- | --- | --- |
| DRUGLIBRARY_ID | Drug Library ID | NUMERIC |
| GENERICDRUGID | Generic Drug ID | NUMERIC |
| SERVICELINEID | Service Line ID | NUMERIC |
| CCA_ID | CCA ID | NUMERIC |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| FINALIZATIONDATE | Finalization Date | DATETIME |

In one embodiment of the aggregation process, a configuration library detail parameterized table is used to store configuration library details, such as drug library details for each device type in each institution in the database 140. This table can also be built from the input data in the configuration library. The following table provides an example of some of the details of what can be stored in this table:

| Column Name | Description | Data Type |
| --- | --- | --- |
| DRUGLIBRARY_ID | Drug Library ID | NUMERIC |
| PARAMETERNAME | Parameter Name | VARCHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed program | VARCHAR |
| PARAMETERVALUE | Parameter Value | VARCHAR |

In one embodiment of the aggregation process, a ship to table is used to store institution ship to identifiers in database 140. The following table provides an example of some of the details of what can be stored in this table:

| Column Name | Description | Data Type |
| --- | --- | --- |
| SHIPTO_ID | Ship To ID. | VARCHAR |
| ADD_DT | Added date | DATETIME |
| ADD_BY | Added by | VARCHAR |
| ADD_PRGM | Added program | VARCHAR |
| LST_CHNG_DT | Last changed date | DATETIME |
| LST_CHNG_BY | Last changed by | VARCHAR |
| LST_CHNG_PRGM | Last changed prgm | VARCHAR |
| ZIPCODE_ID | Zip Code ID | VARCHAR |
| ACCOUNT_ID | Account ID | VARCHAR |
| DEA_NMBR | DEA Number | VARCHAR |
| STATE_ID | State ID | VARCHAR |
| CITY | City | VARCHAR |
| HIN_NMBR | HIN Number | VARCHAR |
| ADDRESS | Address | VARCHAR |
| LABEL | Label | VARCHAR |
| STATUS | Status | VARCHAR |

As mentioned above, as a part of building the above and other permanent tables from the configuration information and activity information received from each of the institutions and medication delivery systems therein, various temporary tables are also generated each time an institution sends new information. The temporary tables are updated with each of the respective data which is appropriate for the table in question, from each of the institutional configuration information, activity information and other information, one institution and/or one specific table at a time. Once all of the information from all of the institutions has been processed or aggregated into the temporary tables, permanent tables are loaded with the information from the temporary tables. In one embodiment, temporary tables are created before loading the permanent tables for at least the following permanent tables: asset, asset location, device, event log, event parameter type, event parameter data, event type, and configuration library, such as drug library.

After all the data available in the uploaded institution files are moved into the temporary tables, the aggregation application will process the uploaded institutional/facility data and update certain master tables, benchmark or activity information tables, and configuration library tables. Specifically, the following master tables are updated (if there is new information to update the tables with): infuser, infuser type, service line, and generic drug. In one embodiment, the aggregation application selects a distinct customer ID (institution) from the event log table to update the "benchmark" or activity information summary information. The existing benchmark summary information for the selected institution for a particular date will be deleted from the benchmark summary table and new details will be inserted. For each benchmark report, described below, the summary information will be calculated and will be updated in the benchmark summary table.

Referring to FIGS. 4A, 5, and 6, certain "benchmarking" or activity information reporting functionality is provided through interface screen displays which are generated by the configuration/activity information application, through the web access server 160 or other server, for use at the client computer 150. Prior to the screen display shown in FIG. 4A appearing, an institutional/facility user is provided with a login screen for the user to enter a user ID and a password. Users can be categorized for different access to information within the system. Specifically, a user can have a user type, for example a "BENCHMARK" or activity information user type, an RXRULES or configuration information user type, or both. The user ID, passwords, user types and other user details are maintained and can be entered and/or modified by an administrator, as will be described further below. Assuming the user is a BENCHMARK user type, once a successful login occurs, a welcome screen display appears and a preferences option appears on the screen for the user to select, along with other options such as BENCHMARK, help, logoff, and/or other options to select. Within the preferences interface screen display shown in FIG. 4A, the user is provided with the ability to set preferences on what activity information from its other institutional activity information within the database 140 that the user is interested in viewing, for which that user has access to based on the user's system account. In particular, the user is provided with an entity name drop down selection menu 400 to choose from a list of entities that the user is interested in viewing activity information on within the user's own institution. The user is also provided with an entity type drop down 404 selection menu to select or include, but not limited to, the following entity types: rural, community, teaching/university, and multi-hospital health system. As indicated above, entity types can include rural, community, or teaching/university. Health system types, excluding stand alone facilities, can include multi-hospital health systems. The user is further provided with a bed size drop down selection menu 408 to select from one of the following predetermined or selected ranges: 1-99, 100-199, 200-299, >=300. The application can be structured to allow a user to modify these ranges or create customized ranges. The user is also provided with a drop down default infuser type selection menu 412 to select from one of the following: PLUM A+ and LIFECARE PCA, which are trademarks of the assignee of the present invention, HOSPIRA, INC., for specific medical devices such as specific medication delivery pumps. Other specific medical devices can be provided on the list, which are provided by the vendor or other vendors of medical devices The user can further be provided with a default time frame drop down selection menu 416 to include, but not limited to the following time frames to run activity information reports: by month and by quarter. The interface and application can be configured to allow the user to display results by a time frame designated by the user other than these specific time frames, such as by entering a number of days, a number of weeks, a number of months, a number of years, a combination of one of more of the previously mentioned time frames, and/or a beginning date and an ending date, such as a beginning month and an ending month. Other configuration and/or activity information reports can be generated using these and other time parameters. The entity type and the bed size typically makes up what is identified as an institution's "peer group," although additional and/or other criteria can be used. When running a specific activity information report, the user can change any one of the default selections to another selection. In addition to the above-described drop down selection menus shown in FIG. 4, the configuration/activity information application could be configured and the configuration/activity information database in the repository 140 could be configured to provide additional drop down selection menus for additional search criteria. For example, the screen display of FIG. 4 can also provide the ability to select one or more peer groups outside of the facility's peer group or all peer groups in addition to the options shown, and obtain similar trending and other information as provided in FIGS. 5 and 6 described below, but for facilities within and outside of (or both) their own institution.

From the main user screen for BENCHMARK user types, which appears after login is successful, the user can select the BENCHMARK option, and two further options can then be provided for the user to select from. Specifically, the user can be provided with a "Summary—Last Available Month" (summary activity information) option and a "Peer Group Comparison Trend" or peer group activity information. In order to view summary activity device/pump information on devices/pumps within the selected facility from within preferences interface display screen, the user can select the Summary—last available month (summary activity information) option. Once this option is selected, the user is presented with a summary screen for the entity results they desire to view, pre-loaded based on their user preferences, the user is then provided with a dropdown menu to select a device/pump type. The previously selected device/pump type from the default infuser type drop down menu 412 within the preferences interface screen display appears. However, the user can change this selection. Once the user selects the device/pump type for which the user would like to run the report, the user can select a show report button and the interface screen display similar to that which is shown in FIG. 5A will appear.

Figure 5A:
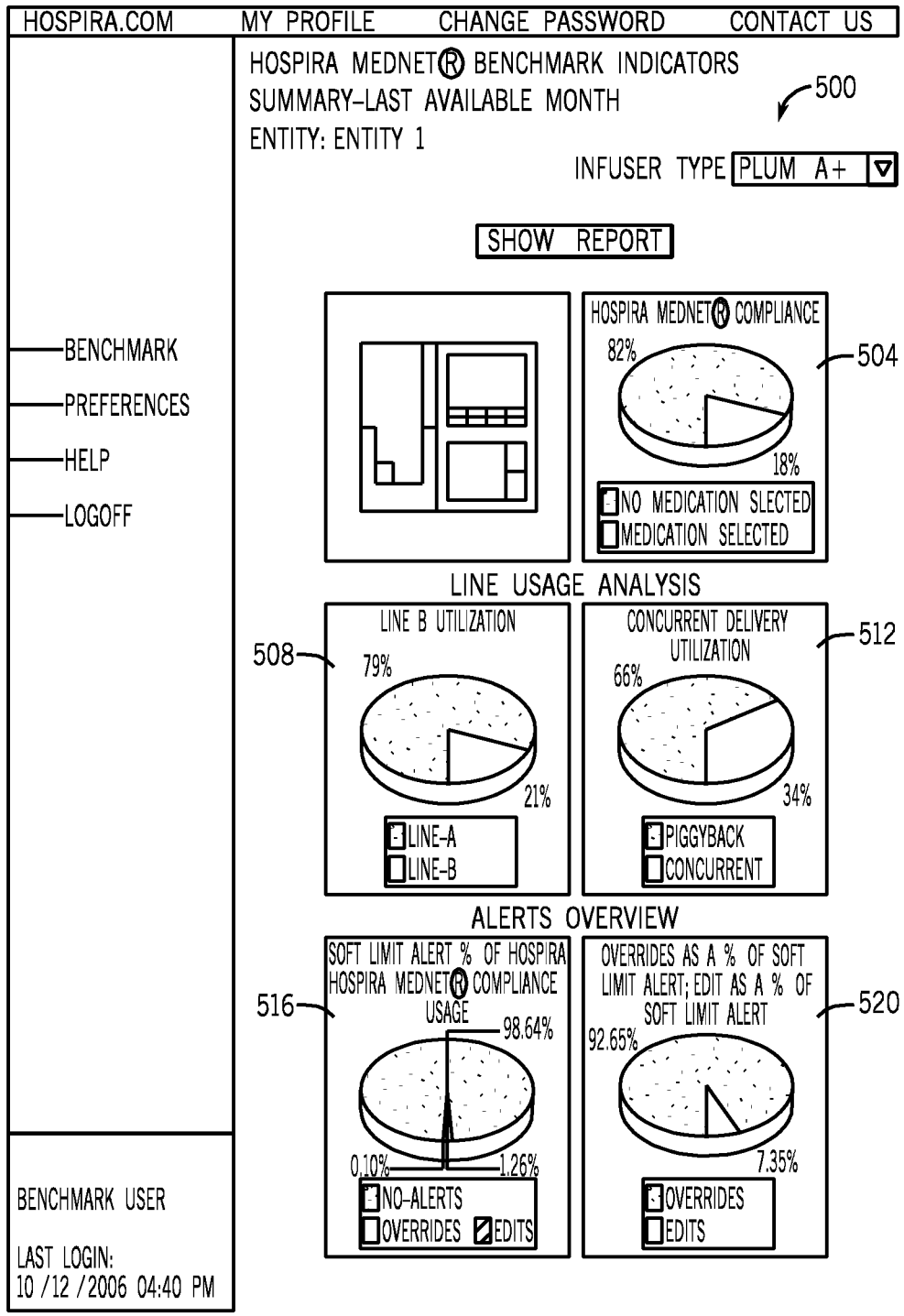
FIG. 5A is an interface screen display of results of particular preferences selected using the selection functions of FIG. 4A or FIG. 4B over the last month.

The summary report 500 shown in FIG. 5A for PLUM A+ infusion devices includes a compliance chart 504, a line B utilization chart 508, a concurrent delivery utilization chart 512, a soft limit alert chart 516, and an overrides and edits chart 520. This information will change based on the medical device being considered. In FIG. 5A, the compliance chart 504 provides an indication of the percent of time that a medication is selected by a clinician from the drug libraries within each device/pump for that pump type during programming of the device/pump. The line B utilization chart 508 provides an indication of the amount of time that the second line of each pump of that pump type is being used within the selected institution. The concurrent delivery utilization chart 512 provides an indication of the percent of time that concurrent verses piggyback usage is taking place within the selected institution for pumps of the selected pump type. The soft limit alert chart 516 provides an indication of the percent of time that that soft limit alerts are taking place in relation to when the drug library information, including limits, are used on a per delivery basis. The overrides and edits chart 520 provides an indication of the percent of time that overrides occur (pump ran as programmed despite alert) and the percent of time edits (changes) to the delivery parameters occur in relation to when soft limit alerts occur, on a per soft limit alert basis. These charts are only a few examples of the type of device/pump activity information that can be reported to institutional users based on the device type, and other selectable preferences.

Figure 5B:
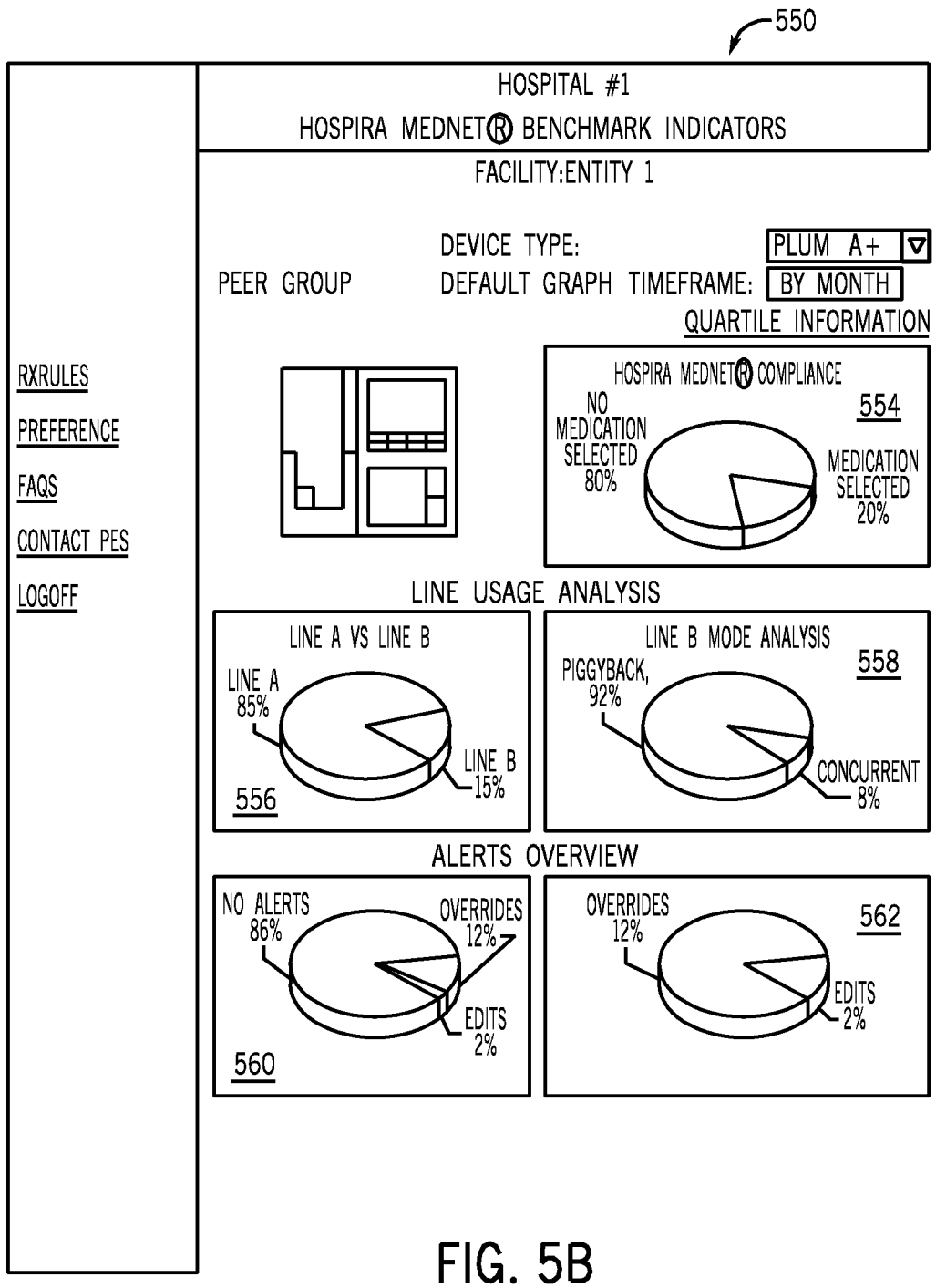
FIG. 5B is an interface screen display of results using alternative reporting preferences, and providing additional information as compared to FIG. 5A.

Specifically, the summary report 550 shown in FIG. 5B for PLUM A+ infusion devices includes a compliance chart 554, a line A vs. line B usage chart 556, a line B mode utilization chart 558, no alerts vs. overrides vs. edits chart 560, and an overrides vs. edits chart 562. This information will change based on the medical device being considered. In FIG. 5B, the compliance chart 554 provides an indication of the percent of time that a medication is selected by a clinician from the drug libraries within each device/pump for that pump type during programming of the device/pump. The line A vs. line B utilization chart 556 provides an indication of the amount of time that the first line of each pump of that pump type is being used within the selected institution verses the amount of time that the second line of each pump of that pump type is being used within a selected institution. The line B utilization chart 558 provides an indication of the amount of time that the second line of each pump of that pump type is used in a "piggyback" implementation and the amount of time that the second line of each pump of that pump type is used in a "concurrent" implementation, within the selected institution. An alert/override/edits chart 560 provides an indication of the percent of time that there are no alerts, there is an alert and an alert override was performed without an edit, and there are edits to the delivery parameters once a soft limit alert issues. The overrides and edits chart 562 provides an indication of the percent of time that overrides occur (pump ran as programmed despite alert) and the percent of time edits (changes) to the delivery parameters occur in relation to when soft limit alerts occur. Each of these charts can be provided for particular timeframes, such as months, and/or for particular peer groups or all peer groups. Again, other examples of device/pump activity information can be reported to institutional users based on the device type, and other selection preferences. In FIG. 5B, the user in this figure is also an RXRULES user, as an RXRULES link or option appears on the left side of the screen display, other options such "preferences" are available as well. A generic "Peer Group" indicator is listed at the top of the screen display, which indicates that a particular peer group can be selected or all peer groups can be selected for reporting the activity information.

As mentioned, a BENCHMARK user type user can also be provided with a "Peer group comparison—Trend" information or peer group activity information option. This option will provide an institutional/facility user with the ability to compare device/pump activity information for their selected institution to all of the peer institutions within the selected entity's peer group. After selecting this option, the user will be provided with a summary screen display which allows the user to select a time frame drop down selection menu allowing display of summarized data by quarter, by month or some other time frame to be defined later. The user can be provided with a show report button on this screen as well. If the user selects the show report button, the user will be provided with an interface screen display similar to that which is shown in FIG. 6A.

Figure 6A:
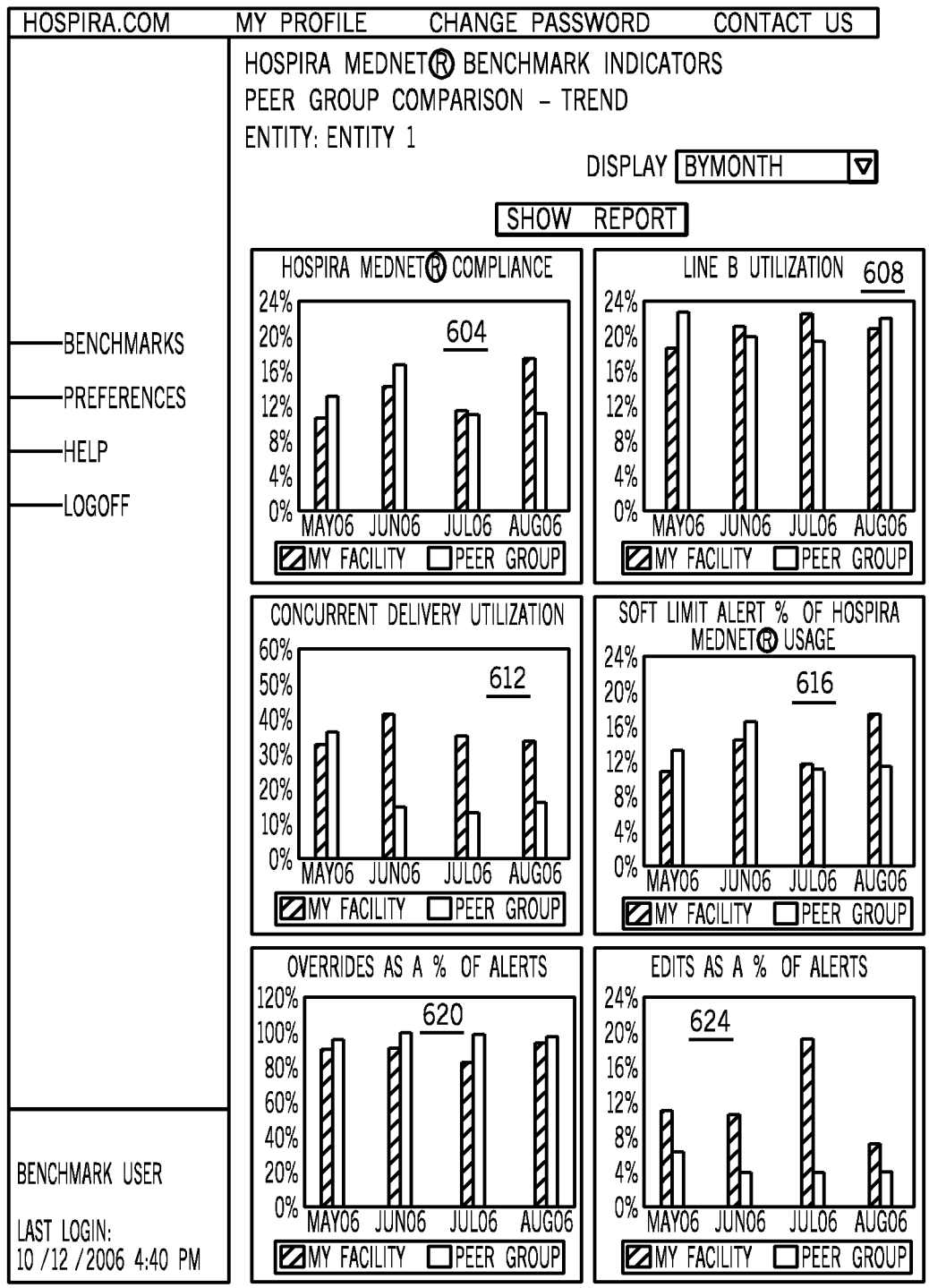
FIG. 6A is an interface screen display of results of particular preferences selected using the selection functions of FIG. 4A or FIG. 4B over a selected time period.

The interface screen display shown in FIG. 6A for PLUM A+ infusion devices includes a compliance graph 604, a line B utilization graph 608, a concurrent delivery utilization graph 612, a soft limit alert graph 616, an overrides graph 620, and an edits graph 624. The compliance graph 604 provides an indication of the percent of time that a medication is selected by a clinician using the configuration information, such as drug libraries, within each device/pump for that device/pump type during programming of the device/pump, for the user's institution and for the entire peer group to which the facility is a part. The line B utilization graph 608 provides an indication of the amount of time that the second line of each device/pump of that device/pump type is being used within the user's facility and within the entire peer group to which the facility is a part. The concurrent delivery utilization graph 612 provides an indication of the percent of time that concurrent (versus piggyback) usage is taking place within the user's institution and within the entire peer group to which the facility is a part. The soft limit alert graph 616 provides an indication of the percent of time that soft alerts are taking place in relation to when the drug library information, including limits, are used on a per delivery basis, for the user's institution and for the entire peer group to which the institution is a part. The overrides graph 620 provides an indication of the percent of time that overrides occur, as well as the percent of time edits to the delivery parameters occur, in relation to when soft limit alerts occur, on a per soft limit alert basis, for the user's institution and for the entire peer group to which the institution is a part. The edits graph 624 provides an indication of the percent of time that edits to the delivery parameters occur in relation to when soft limit alerts occur, on a per soft limit alert basis, for the user's institution and for the entire peer group to which the institution is a part. These graphs are only a few examples of the types of device/pump activity information that can be reported to institutional users for a PLUM A+ device.

Figure 6B:
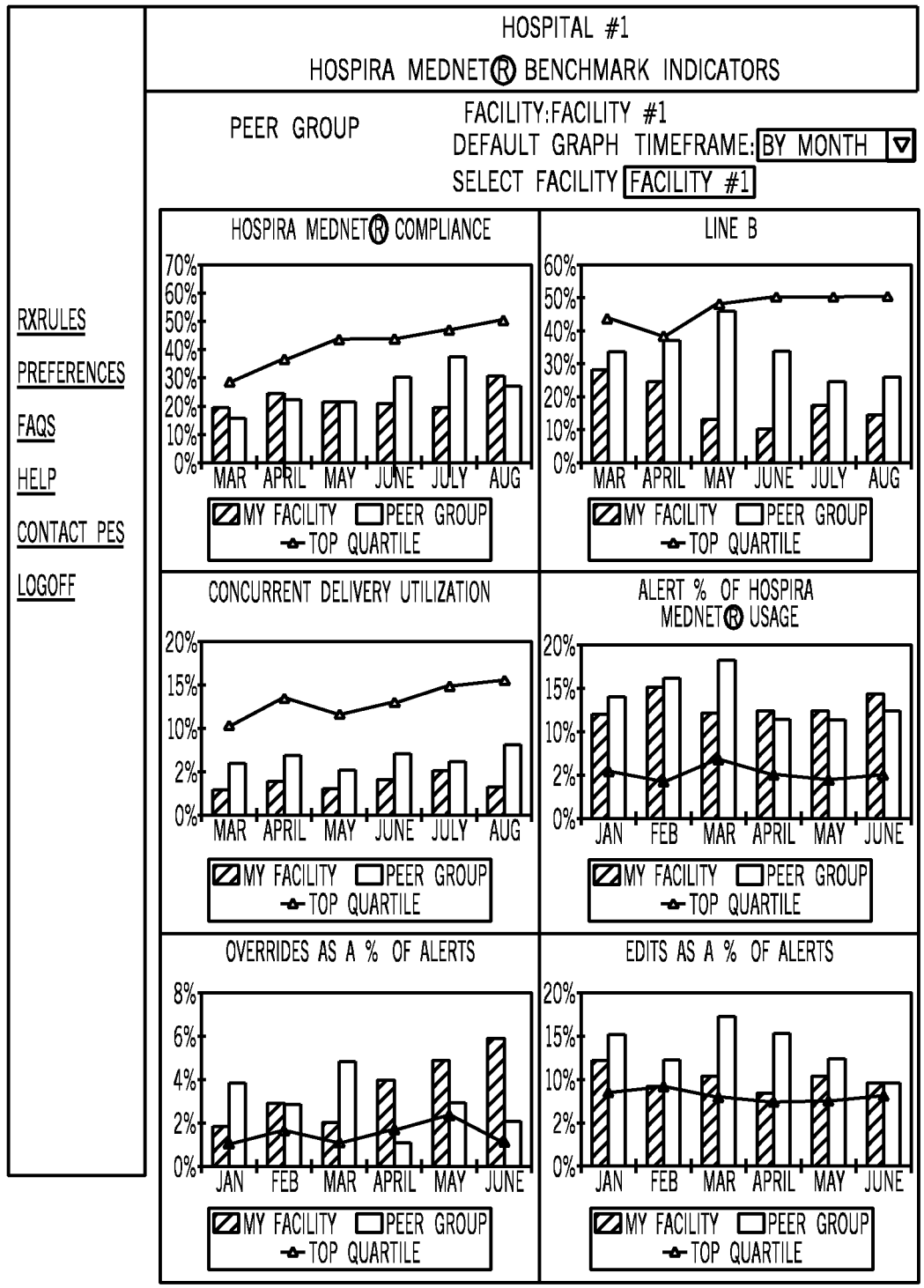
FIG. 6B is an interface screen display of results using alternative reporting preferences, and providing additional information as compared to FIG. 6A.

Specifically, interface screen display shown in FIG. 6B for medication delivery devices having a "line B" (for example, infusion pumps having first and second infusion lines) generally shows the same charts as shown in FIG. 6A. However, FIG. 6B also shows at least the "top quartile" for a selected peer group or for all peer groups, if all peer groups are selected or if no peer group is selected.

Figure 6C:
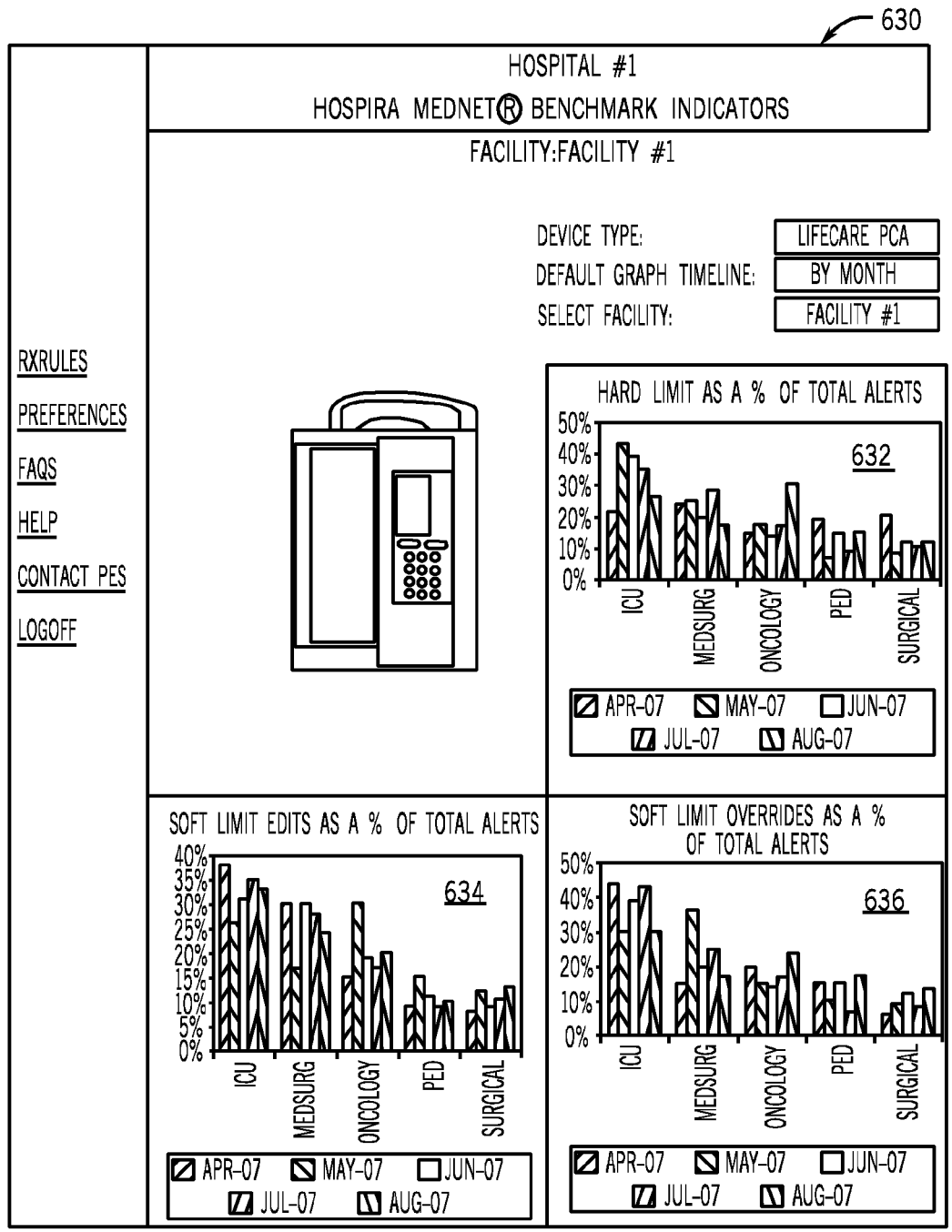
FIG. 6C is an interface screen display of results using alternative reporting preferences, and providing additional information as compared to FIG. 6A.

FIG. 6C shows a further summary report 630 that can be generated within the BENCHMARK application. The summary report 630 shown is for LIFECARE PCA infusion devices (manufactured and sold by the assignee of the present invention, HOSPIRA, INC.), and includes hard limit edits chart 632, a soft limits edits chart 634, and a soft limits overrides chart 636. This information will change based on the medical device being considered. In FIG. 6C, the hard limit edits chart 632 provides an indication of the percent of time that a hard limit edit occurred when an alert occurred, for each clinical care areas (CCAs) of ICU, MedSurg, Oncology, Ped (pediatrics), and Surgical, for each of the five (5) different months listed. The soft limit edits chart 634 provides an indication of the percent of time that a soft limit edit occurred when an alert occurred, for each clinical care areas (CCAs) of ICU, MedSurg, Oncology, Ped, and Surgical, for each of the five (5) different months listed. The soft limit override chart 636 provides an indication of the percent of time that a soft limit override occurred when this type of alert occurred, for each clinical care areas (CCAs) of ICU, MedSurg, Oncology, Ped, and Surgical, for each of the five (5) different months listed. Each of these charts can be provided for different timeframes, for different facilities, and/or for particular peer groups or all peer groups. Again, other examples of device/pump activity information can be reported to institutional users based on the device type, and other selection preferences. A total compliance chart can be added by clicking on "Add Total Compliance" link at the top of the screen display. In addition, a "Looking for more reports options" link can be provided to allow a user to have access to additional reporting options.

Figure 6D:
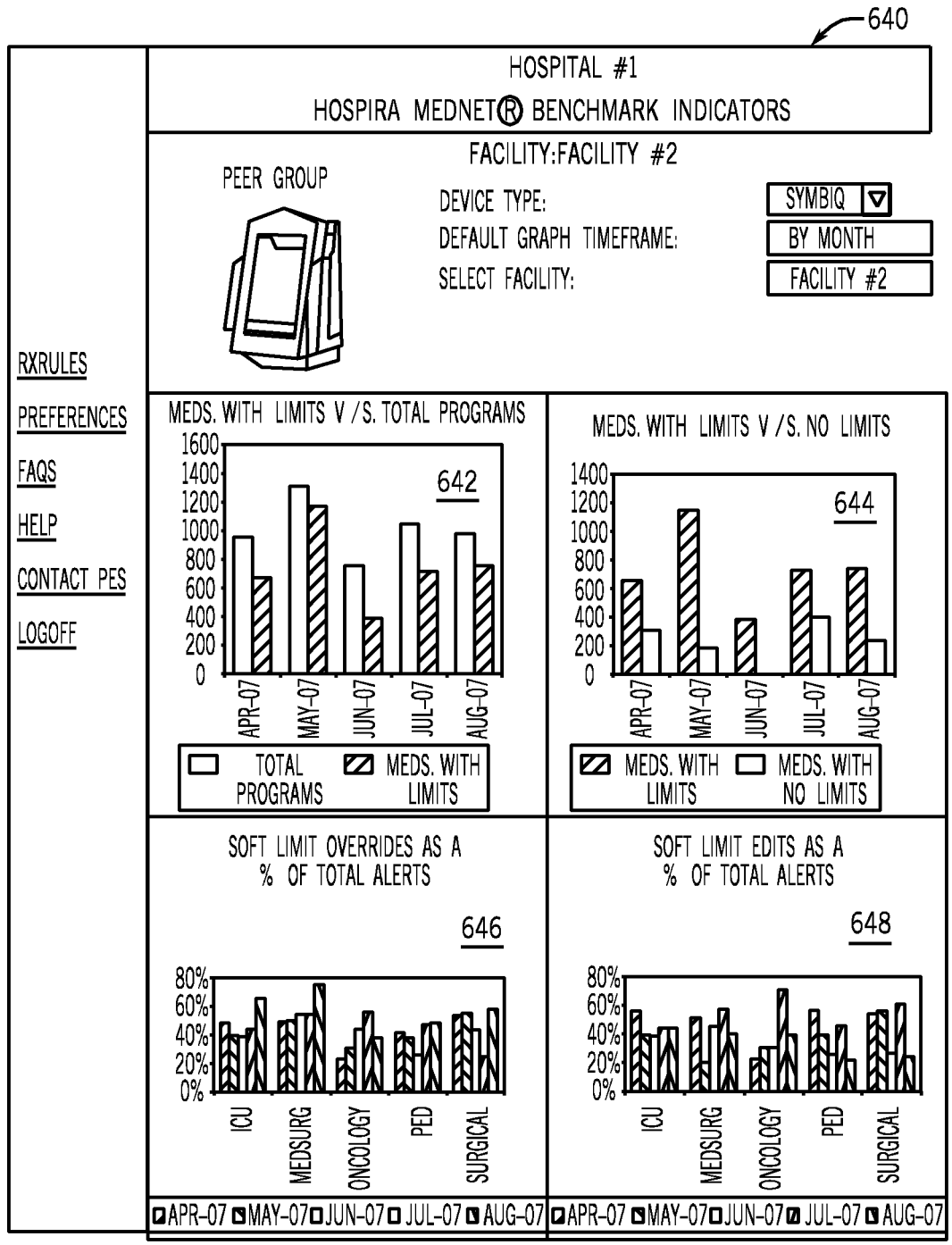
FIG. 6D is an interface screen display of results using alternative reporting preferences, and providing additional information as compared to FIG. 6A.

FIG. 6D shows a further summary report 640 that can be generated within the BENCHMARK application. The summary report 640 shown is for SYMBIQ infusion devices (manufactured and sold by the assignee of the present invention, HOSPIRA, INC.), and includes a medications with limits vs. total programs chart 642, a medications with limits vs. no limits chart 644, a soft limits overrides chart 646, and a soft limits edits chart 648. This information will change based on the medical device being considered. In FIG. 6D, the medications with limits vs. total programs chart 642 provides an indication of the number of times the SYMBIQ infusion pumps are programmed for delivery with medications having limits along with an indication of the total number of times the SYMBIQ infusion pumps have been programmed, for each of the five (5) different months listed. The medications with limits vs. no limits chart 644 provides an indication of the number of times the SYMBIQ infusion pumps are programmed for delivery with medications having limits along with an indication of the number of times the SYMBIQ infusion pumps have been programmed for delivery with medications having no limits, for each of the five (5) different months listed. The soft limit override chart 646 provides an indication of the percent of time that a soft limit override occurred when this type of alert occurred, for each clinical care areas (CCAs) of ICU, MedSurg, Oncology, Ped, and Surgical, for each of the five (5) different months listed. The soft limit edits chart 648 provides an indication of the percent of time that a soft limit edit occurred when an alert occurred, for each clinical care areas (CCAs) of ICU, MedSurg, Oncology, Ped, and Surgical, for each of the five (5) different months listed. Each of these charts can be provided for different timeframes, for different facilities, and/or for particular peer groups or all peer groups. Again, other examples of device/pump activity information can be reported to institutional users based on the device type, and other selection preferences.

Figure 6E:
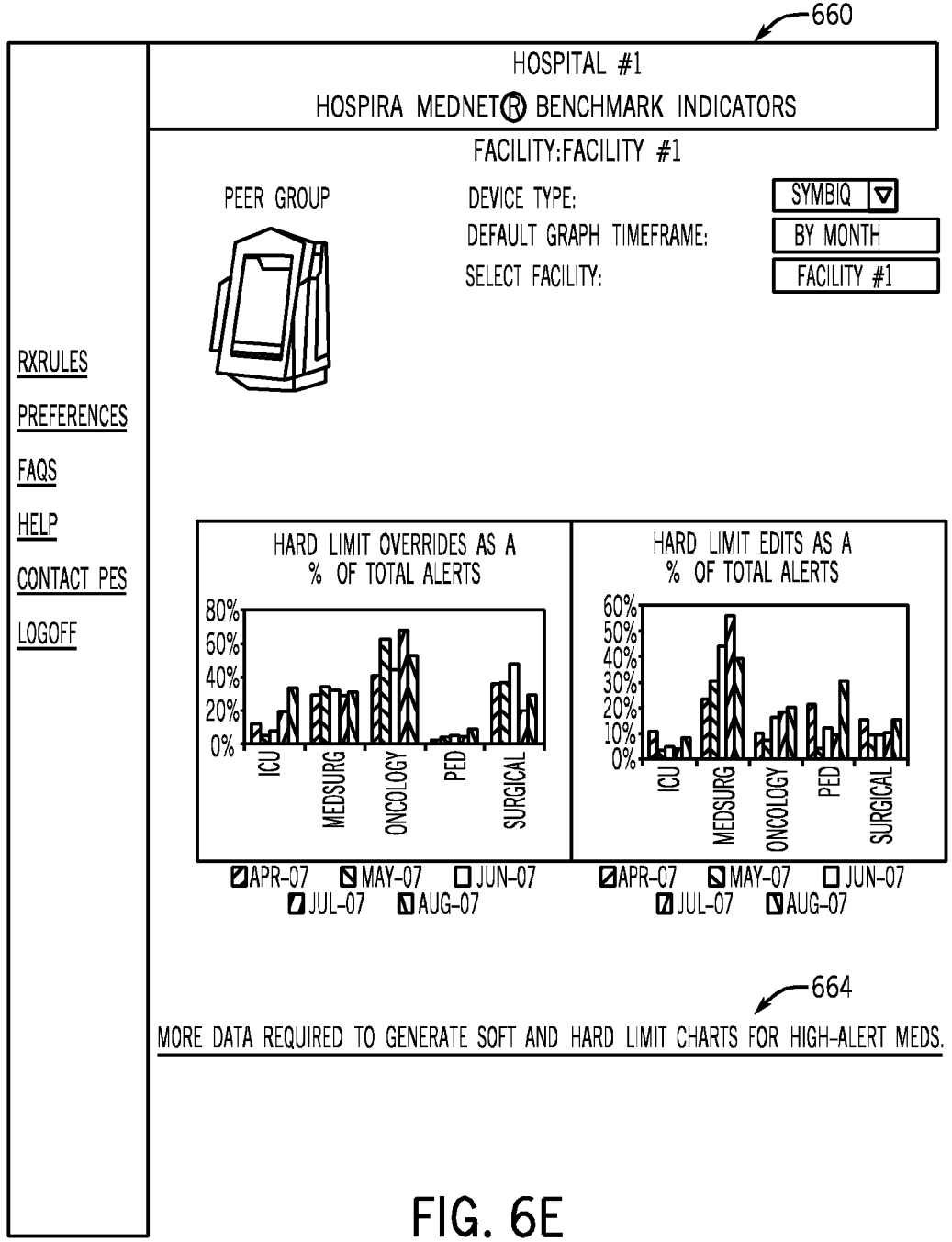
FIG. 6E is an interface screen display of results using alternative reporting preferences, and providing additional information as compared to FIG. 6A.

FIG. 6E shows a further summary report 660 that can be generated within the BENCHMARK application. The summary report 660 shown is for SYMBIQ infusion devices, and includes the same or similar charts as prior figures, such as FIG. 6C. However, this report includes a data warning 664, stated as "More data required to generate soft and hard limit charts for High-Alert meds." Specifically, the activity information/configuration information application 136, 136' can be configured to issue a data warning 664 if there is not enough activity information in the configuration/activity information database 140, 140'. When the customer/user enters reporting preferences for generating a report of chart through a screen display for generating such a report, the configuration information/activity information application 136, 136' receives the reporting preferences or parameters.

The configuration information/activity information application 136, 136' can be configured to determine if sufficient data has been received and stored to generate such a report based on the received preferences or parameters. In one embodiment, the configuration information/activity information application 136, 136' performs this determination by comparing an amount of data received and stored in the configuration/activity information database 140, 140' related to the at least one of the report parameters to a predetermined data input level. If the amount of data received and stored in the configuration/activity information database 140, 140' related to the at least one of the report parameters does not meet the predetermined data input level, the configuration information/activity information application 136, 136' is configured to generating a data warning 664, in the place of one or more report charts within the generated report. Alternatively, if there is some data, but not enough data in relation to the predetermined data input level, in the configuration/activity information database 140, 140' relating to the parameters entered to generate the report, the configuration information/activity information application 136, 136' can be configured to still run the report including the chart related to the requested parameters, but instead generate a warning proximate to the respective chart(s) that the chart has been generated with less then an optimal amount of data for the requested parameters. In one embodiment, the data warning 664 can read as follows: "Warning—this chart has been generated using data from less than five (5) institutions, and therefore may not be reliable data and should not be used to make administrative decisions". It has been determined that using data from less than five (5) institutions may not be reliable for making administrative decisions.

If the configuration information/activity information application 136, 136' determines that the amount of data received and stored in the configuration/activity information database 140, 140' meets (greater than/greater than or equal to) the predetermined input level (such as data from five (5) institutions from an FTP process or data extraction referred to herein), then the configuration information/activity information application 136, 136' will run the report including generating the chart for the received report preferences or parameters. In a further embodiment, instead issuing a data warning 664, even when the amount of data received and stored in the configuration/activity information database 140, 140' meets (greater than/greater than or equal to) the predetermined input level relating to the requested preferences/parameters for the report, when the report and chart(s) is generated, a data warning 664 can be issued which indicates the number of institutions which were used to generate the information with the chart. Thus, a data warning 664 can be displayed for each chart indicating the level of data used to generate such chart. Further, when the configuration information/activity information application 136, 136' generates each report and/or chart therein, the configuration information/activity information application 136, 136' can also calculate statistical information, such as a "P Value", an "R Value", and/or a standard deviation, and display such statistical information within each report and/or proximate each chart for which such statistical information is calculated.

In the context of the data warning 664 issuing under the circumstances described herein, in the process of the configuration information/activity information application 136, 136' determining if sufficient data has been received and stored to generate a reliable report based on the received preferences or parameters, the configuration information/activity information application 136, 136' can also or instead, calculate statistical information and compare the statistical information to one or more predetermined minimum statistical reliability thresholds. The predetermined minimum statistical reliability thresholds can be a "P Value", "R Value", standard deviation, and/or some other statistical threshold, which can be set by the customer or user. If one or more of the predetermined minimum statistical reliability thresholds are not met, then the configuration information/activity information application 136, 136' can be configured to generate a data warning 664, in the place of one or more report charts within the generated report or in addition to the chart(s) for which the predetermined minimum statistical reliability threshold has not been met. In this embodiment, the data warning 664 can include the one or more of the calculated statistical information as reasons for the warning. For example, the warning can include the following: "Warning—the P Value for the data used to generate this chart is X. Therefore, the amount of data used to generate this chart may not be reliable and this chart should not be used to make administrative decisions." "X" can be a numerical value. Other statistical information can be presented instead of this example or in addition to this example.

Within the above and other "BENCHMARKING" interface screens and respective reports, charts and other forms of presenting the activity information provided through such interface screens from use of the configuration information/activity information application 136, 136', such activity information is typically being provided to a customer for a customer's own institution. However, in one further embodiment, the configuration information/activity information application 136, 136' can be configured to allow a customer to view and run reports on another institution's activity information, such as allowing a customer to run the above and other reports about another institution's activity information. The configuration information/activity information application 136, 136' can also be configured to allow a customer to view and run reports on other details about such other institution(s), such as the number of beds, the peer group such other institution falls within, etc., to allow a customer to compare the other institution's activity information with their own. In one preferred embodiment, such other institution's identity will not be provided to the customer. In a further embodiment, the configuration information/activity information application 136, 136' can also be configured to allow a customer to obtain this and other activity information about another institution, and to allow such a customer to compare such other institution's activity information against an the entire database of all of the institutions' activity information for the preferences requested by the customer, compare such other institution's activity information against the entire database of all of the institutions' activity information for one peer group for the preferences requested by the customer. Using this feature, a customer may be able to more readily "benchmark" the activity information, and thus their own configuration information, for their institution against the activity information, and thus the configuration information, of other institutions.

After activity information and/or configuration information is transferred from and/or extracted from institution/facility servers, and transferred to the configuration/activity information aggregation server 132, 132', as a part of the aggregation process or after the aggregation process of the configuration/activity information from all of the institutions into the multi-institutional configuration/activity information database 140, 140', a cleaning process can be performed by the aggregation server and/or application 132, 132' or by the configuration/application server/application 136, 136'. This cleaning process includes removing all institution/facility identifying information which would allow a user of the configuration information/activity information application 136, 136' to otherwise identify the name, location or other information about any of the institutions which would allow a user to determine the identity of such institution/facility for which activity information/configuration information had been included within the activity/configuration information database 140, 140'. Fake or generic institution/facility/other names and/or identifiers could be substituted for actual institution/facility/other names and/or identifiers during the cleaning process. Without such actual institution/facility identifying information, the activity/configuration information database 140, 140' could be made available to third parties that are not an institution/facility and that are not a vendor. The vendor could lease and/or sell the "cleaned" database to such third parties for access by such third parties for allowing such third parties to run reports and perform comparisons described herein and run other reports and perform other comparisons. In one embodiment, this distribution of the "cleaned" database of configuration/activity information to third parties can be included with the leasing and/or sale of a modified version (third-party version) of the configuration information/activity information application, which would otherwise allow a third party to run the BENCHMARKING and/or RXRULES reports, and other reports. The modifications could include at least reduced administration functions, which for example would not need to include file transfer/extraction processes, settings, and interface screens to provide such settings. In one embodiment, the "cleaned" database of configuration/activity information, as well as the modified version (third-party version) of the configuration information/activity information application can be included within an RCLDA 182 or as a part of the HOSPIRA MEDNET application implemented within an institution server 108, 108' for use by a customer to assist the customer is setting up configuration information, such as a drug library, for the customer institution, as described herein.

In addition to the reports and information that can be provided through and/or within the interface screens shown in FIGS. 4A-6E, the configuration information/activity information application 136, 136' can be configured to also generate other reports or summary information, such as a time to program report, in chart or other form, which conveys a high, low, average, and/or median amount of time it takes to program medical devices, such as infusion pumps, by time frame, by peer group (or all peer groups), by CCA, and/or by some other preference. Comparisons can be performed between or against certain or all CCAs, peer groups, and/or other target groups, as is shown and described for other reports herein. The configuration information/activity information application 136, 136' can also be configured to generate a time to transfer information report, in chart or other form, which conveys a high, low, average, and/or median amount of time it takes for each FTP and or data extraction process on an institution by institution level, for all institutions, by time frame such as each day, by peer group (or all peer groups), and/or by some other preference. Comparisons can be performed based on at least size or peer group of institutions. The configuration information/activity information application 136, 136' can also be configured to generate a medical device usage report in chart or other form, which conveys how many medical devices are used in an institution, frequency of use of such medical devices, and/or how many medical devices are not used within in an institution, by time frame, by peer group (or all peer groups), by CCA, and/or by some other preference. The frequency of use can be displayed with a high, low, average, and/or median frequency of use details. The configuration information/activity information application 136, 136' can further be configured to generate a configuration information download report in chart or other form, which conveys when and how often configuration information, such as a drug library, is downloaded from a medication management unit (MMU) or from an RCLDA 182, such as from a HOSPIRA MEDNET software application running on a local or remote server, to a medical device, such as infusion pump. This configuration information download report can also provide information on which user performed each download and/or how many downloads each user performs. The configuration information download report can be run by time frame, by peer group (or all peer groups), by CCA, and/or by some other preference.

The configuration information/activity information application 136, 136' can further be configured to generate a medical device button press count report in chart or other form which conveys how many times a user or caregiver presses buttons on a medical device, such as an infusion pump, when the user is programming the medical device for each set of programming actions (for one (1) programming). Like the other information for which reports can be run and information provided therein, this information is tracked and stored as a part of the activity information for each medical device. Specifically, which buttons are pressed, when such buttons are pressed, which caregiver pressed such buttons, during which programming, and other information is tracked and stored. The medical device button press count report can be run by time frame, by peer group for all users (or all peer groups), by CCA, and/or by some other preference. A comparison can then be performed for a user's information vs. all users in a CCA vs. all users in a particular peer group, and/or vs. some other preference to determine how well that user is performing. A further comparison can then be performed for a user's information vs. the number of alarms, alerts and/or errors that occurred for such programmings in relation to alarms, alerts, and/or errors that occurred for similar types of programmings by others, overall, by peer group, by CCA, and/or by some other preferences, to determine whether such user programmings are indicative a particular user being more susceptible to errors in programming Statistical information can be calculated for each of the reports to assist in determining whether the reported information is quantitatively significant and the level of significance of such information. The configuration information/activity information application 136, 136' can be configured to also generate other reports, such as a caregiver level report, in chart or other form, which conveys a high, low, average, and/or median number of alerts (soft limit exceeded) and/or alarm (hard limit exceeded) for medical device programmings for each caregiver level, by time frame, by peer group (or all peer groups), by CCA, and/or by some other preference. Comparisons can be performed between or against certain or all CCAs, peer groups, and/or other target groups, as is shown and described for other reports herein. This caregiver level report will allow a user to determine where training may be needed, for junior and/or more senior caregivers, broken down by CCA and other criteria mentioned above.

Certain medication when delivered through a medical device such as an infusion pump, are considered to be "high alert" medications. For example, the ISMP has designated at least the following medications as high alert medications: amiodarone, colchicine, heparin, insulin, lidocaine, magnesium sulfate, nesiritide, nitroprusside, potassium chloride, potassium phosphate, propofol, and sodium chloride (hypertonic—above 0.9% concentration). As such, the configuration information/activity information application 136, 136' can be configured to also generate a "high alert" medications report, in chart or other form, which can convey one or more or the following information: 1) soft limit overrides for a particular, or all, high alert medication(s) as a percent of total programs (programmings) of the particular high alert medication and/or all high alert medications; 2) soft limit edits for a particular, or all, high alert medication(s) as a percent of total programs (programmings) of the particular high alert medication and/or all high alert medications; 3) hard limit overrides for a particular, or all, high alert medication(s) as a percent of total programs (programmings) of the particular high alert medication and/or all high alert medications; and 4) hard limit edits for a particular, or all, high alert medication(s) as a percent of total programs (programmings) of the particular high alert medication and/or all high alert medications. Similar to all other activity/configuration information reporting herein, high, low, average, and/or median information can be provided for the activity information. Also similar to all other activity/configuration information reporting herein, such reporting can be provided for each caregiver level, by time frame, by peer group (or all peer groups), by CCA, and/or by some other preference. Comparisons can be performed between or against certain or all CCAs, peer groups, and/or other target groups, as is shown and described for other reports herein. Further, similar to all other activity/configuration information reporting herein, statistical and other useful information can be calculated for the reported activity/configuration information, and can be used by the configuration information/activity information application 136, 136' to further issue warnings and/or further alerts on the interface screen of the report, by email notification, or by some other electronic means, to provide warnings related to the activity/configuration information for which the calculations were performed. As explained and contemplated by the various embodiments described herein, once a customer/user runs a report herein, as an option in the reports or as provided through some other interface mechanism, the configuration information/activity information application 136, 136' can provide the user with a "show medication library" or "show library entry(s)" icon (not shown) a listing of the drug library entries which are directly related to the results of the report. Such a "show medication library" or "show library entry(s)" icon (not shown) can be provided for each chart within a report, for the set or subset of activity/configuration information resulting from the parameters/preferences used to generate the report. For example, if a user runs a report for a particular type of infusion pump, a particular CCA, and a particular peer group and is provided with information such as is shown in one or more of FIGS. 5A-6E, if the user likes the results, the user could then click on the "show library entry(s)" and be provided with the ability to select one or more drug library entries, and place such entries within a shopping cart (described in greater detail below) or place such entries directly into a library or sub-library, such as for a particular CCA, being created by the user. This functionality can be implemented with all reporting features, as appropriate for such reporting features.

Instead of or in addition to focusing in on "high alert" ISMP medications, the configuration information/activity information application 136, 136' can be also be configured to allow a user to enter preferences and run reports on medications which are used the most within all institutions, within peer groups, within CCAs, etc. For example, the configuration information/activity information application 136, 136' can be also be configured to allow a user to request reporting on the "Top X" medications. The configuration information/activity information application 136, 136' can be configured to receive a value for X, through user selection from a drop down menu or through some other interface means. Thus, if the user selects 20 for X, the configuration information/activity information application 136, 136', similar to the "high alert" medications reporting, can be configured to generate a top medications report, in chart or other form, which can convey one or more or the following information: 1) soft limit overrides for the 20 most used medications as a percent of total programs; 2) soft limit edits for the 20 most used medications as a percent of total programs; 3) hard limit overrides for the 20 most used medications as a percent of total programs; and 4) hard limit edits for the 20 most used medications as a percent of total programs, which can be broken down and utilized in a similar manner as the "high alert" medicine reported information, including at least comparisons, calculation of additional/statistical information, and listing of directly related drug library entries for use in development of new drug libraries and/or editing existing drug libraries.

Some medical devices are arranged or built in a modular configuration. For example, some medical devices can include a central interface module having at least processor, memory, a display, soft and hard keys for a user to interface with the display and program the medical device, a communications interface, as well as software to control the operation of the central interface module and to interface and control the operation of specific purpose modules which can be included in the same housing with the central interface module, removably attached to the central interface module, connected to the central interface module, or merely in communication with the central interface module. One specific purpose module can include a first infusion line control module which acts as a single line infusion pump for infusing a fluid, such as medication, to a patient. The first infusion line control module can have its own processor, memory, software, communications interface, a display and control keys, such as hard and soft keys. Another specific purpose module can include a second infusion line control module which acts as an additional single line infusion pump for infusing a fluid, such as medication, to a patient. A third or additional infusion line control module can be in communication with, connected to or removably attached to the central interface module as well. Other types of modules can operate in conjunction with the central interface module. When this type of medical device is implemented in conjunction with the present invention, activity information and configuration information for each of the modules together, yet separately grouped, can be captured and stored at an MMU or similar server, extracting/transferred, and then aggregated into the configuration/activity information database 140, 140'. The configuration information/activity information application 136, 136' can be configured to allow a customer/user to run reports on activity information for all second infusion line control modules and/or third infusion line control modules, etc., such as for example how often such line is used, for an institution, for all institutions, for all institutions within a peer group, for a particular CCA within all institutions or within a particular peer group, etc., as would be understood from the reporting techniques described herein. If a user obtained access to the configuration information/activity information application 136, 136' prior to making purchasing decisions about how many second infusion line control modules, third infusion line control modules, etc. to purchase, this information could be used to assist such user in determining how many second infusion line control modules, third infusion line control modules, etc. to purchase at the outset, saving time in making such decisions, saving money in not over purchasing, and preventing a shortage of medical device equipment from occurring at some point in time in the future. The configuration information/activity information application 136, 136' can further be configured to suggest how many second infusion line control modules, third infusion line control modules, etc., and other modules and/or medical device equipment based on this and other reports which come to mind based on the present description. Other reports are contemplated by the present description.

Figure 7:
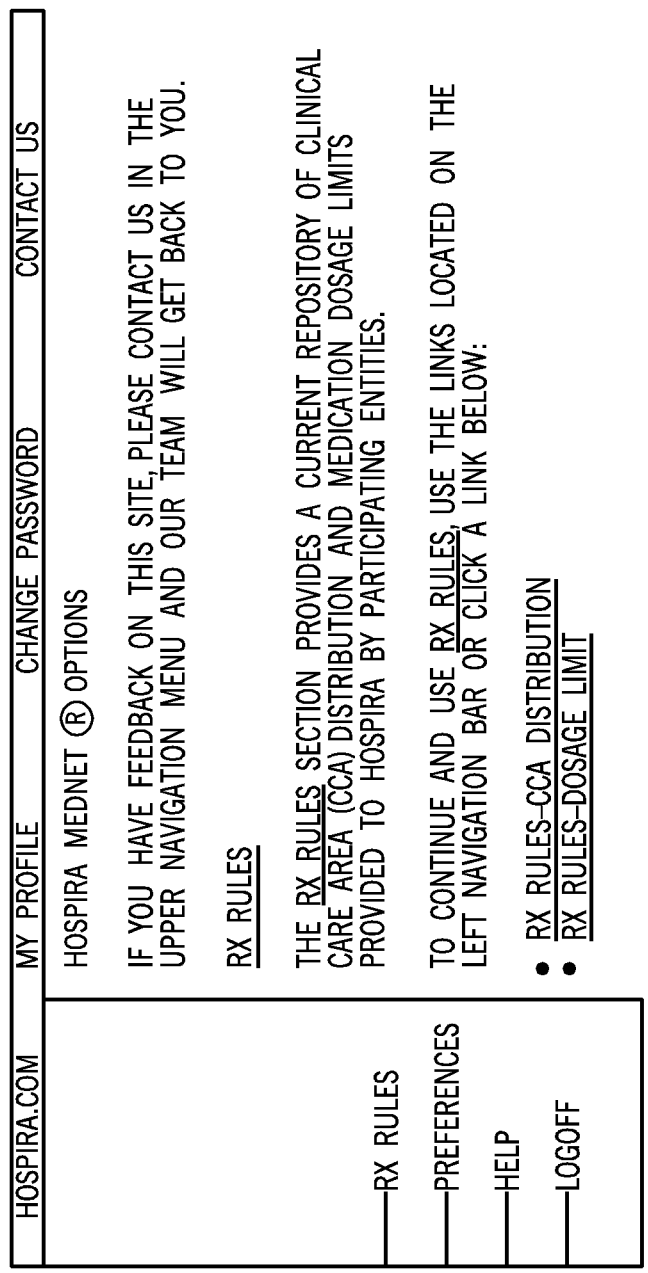
FIG. 7 is an interface screen display of a main menu for configuration information functions.

After a successful login, an RXRULES or configuration user type user is provided with a welcome screen shown in FIG. 7. This screen presents several options to select from including, but not limited to, help, logoff, and preferences. Within the preferences interface screen display shown in FIG. 4B, the user is provided with the ability to set preferences on what configuration information from its other institutional configuration information, if applicable, within the database 140 that the user is interested in viewing. Of course, the user must have the appropriate authorization to such access based on the user's system account. In particular, the user is provided with a entity name drop down selection menu 400 to choose from a list of entities that the user is interested in viewing configuration information on within the user's own institution. The user is also provided with a entity type drop down 404 selection menu to select from, but not limited to, one of the following entity facility types: rural, community, teaching/university, and multi-hospital health system. The user is further provided with a bed size drop down selection menu 408 to include, but not limited to, the following ranges: 1-99, 100-199, 200-299, >=300. The user is also provided with a drop down default infuser type selection menu 412 to select from one of the following: PLUM A+ and LIFECARE PCA, which are trademarks of the assignee of the present invention, HOSPIRA, INC., for specific medication delivery pumps. The entity type and the bed size typically makes up what is identified as an institution's "peer group," although additional and/or other criteria can be used. When running a specific configuration information report, the user can change any one of the default selections to another selection.

From the main user screen for RxRules user types shown in FIG. 7, which appears after login is successful, other choices can be provided. The first choice for selection by the user is RxRules—CCA (clinical care area) Distribution and the second choice is RxRules—Dosage Limits. If the user selects the CCA Distribution option, the user will be provided with an interface screen display similar to that which is shown in FIG. 8.

Figure 8:
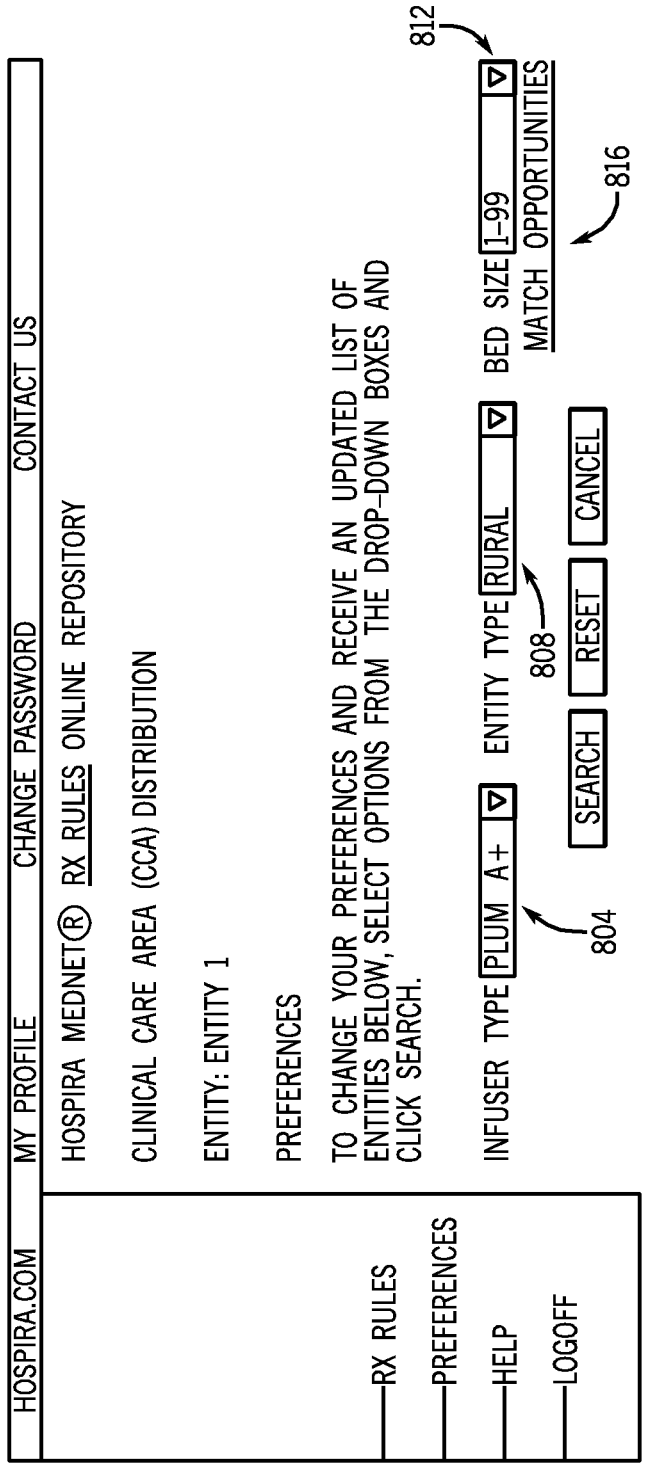
FIG. 8 is an interface screen display of selection functions for facility viewing of critical care area configuration information preferences.

The interface screen display of FIG. 8 provides the user with the ability to select initial criteria or parameters for viewing of other institutions clinical care areas (CCA) distributions. This can help an institution gauge whether their own institution is set up in a manner which is most beneficial to the operation of their institution, and in modifying and/or configuring their own clinical care area distributions. Specifically, the interface screen display of FIG. 8 includes an infuser type drop down selection menu 804 for selecting the type of infuser to view CCA configuration information. Choices for infuser type can include, but are not limited to, PLUM A+ and LIFECARE PCA, which are trademarks of the assignee of the present invention, HOSPIRA, INC., for specific medical devices or medication delivery pumps. Other choices are possible, depending on the type of infuser being used within an institution. The interface screen display of FIG. 8 also includes an entity type drop down selection menu 808 for selecting the type of entities to view CCA configuration information. Choices for entity type include, but are not limited to, rural, community, teaching/university, and multi-hospital health system. Other entity types are possible. The interface screen display of FIG. 8 also includes a bed size drop down selection menu 812 for selecting the number of beds within a facility to view CCA configuration information for such a facility. Choices for bed size include, but are not limited to, 1-99, 100-199, 200-299, >=300. Other ranges are possible.

Once the above initial search parameters are selected, the user can select a "match opportunities" button 816 and the user will be provided with an interface screen display similar to that which is shown in FIG. 9. The interface screen display of FIG. 9 provides the user with a preliminary search results table 900 showing the available search opportunities for which an actual search to find actual CCA results can be performed. If the available search opportunities within the preliminary search results table 900 are acceptable, the user can select a search button to perform the search. Otherwise the user can select a reset button and select other search parameters. In addition, the interface screen display of FIG. 8 can also provide other drop down selection menus for additional targeted searching. Specifically, the screen display of FIG. 8 can include a service line drop down selection menu (not shown) for selecting a service line. CCAs are particular to each institution/facility. However, service lines are the same across different institutions/facilities. Thus, each institution/facility can have one or more CCAs for each service line defined as a part of each institution/facility's defined parameters/information in memory 140. However, each CCA cannot have more than one service line as a part of each institution/facility's defined parameters/information in memory 140. Some examples of service lines are shown in FIG. 10 within the CCA lists 1004, 1008. Other examples of service lines include: behavioral health, bone marrow transplant, burn unit, emergency services endocrinology, eye ear nose & throat, geriatric, hematology, ICU (intensive care unit)—cardiac, ICU—general, ICU—medical, ICU—neonatal, ICU—pediatrics, ICU—surgical, medicine—adult, medicine—neonatal, medicine—pediatric, obstetrics/gynecology, oncology—adult, oncology—pediatric, orthopedics, pain management, rehabilitation, renal, skilled nursing, surgical—adult, surgical—cardiovascular, surgical pediatrics, transplant, trauma, urology, multiple service lines. Other specialty need service lines can include: anesthesia, out patient surgery, telemetry, special procedures, transfusion center, and/or ambulatory. In addition to the above-described drop down selection menus shown in FIG. 8, configuration/activity information application could be configured and the configuration/activity information database in the repository 140 could be configured to provide additional drop down selection menus for additional search criteria. For example, the screen display of FIG. 8 can also provide the ability to select one or more peer groups outside of the facility's peer group or all peer groups in addition to the options shown. In one embodiment, the vendor's system administrator can establish the available drop down selections. In another embodiment, the user institutions may be provided with some flexibility to establish their own drop down selection options.

If the user selects the search button, the user will be provided with an interface screen display similar to that which is shown in FIG. 10. The interface screen display of FIG. 10 provides the user with a generic entity selection window 1000 to select which entities the user would like to view the CCAs for, from those entities which match the search criteria parameters with the database 140. The user can select all or less than all of the entities within the entity selection window 1000. Once the user selects the entity or entities the user would like to view the CCAs for, the user can select the "Show Report"

button, and the user will be provided with an interface screen display similar to that which is shown in FIG. 11. The interface screen display of FIG. 11 provides the user with a listing of the clinical care areas for the first two entities within the entity selection window 1100. Specifically, a first CCA list 1104 is provided within the interface screen display of FIG. 11 showing all of the CCAs for a first entity, the name of which is not identified and remains anonymous. A second CCA list 1108 is also provided within the interface screen display of FIG. 11 showing all of the CCAs for a second entity, the name of which us also not identified and remains anonymous. No information is provided from which the identification of the entities can be determined. Each CCA list 1104, 1108 provides a listing of a service line and a CCA name therefore, providing at least one indication of how the entity distributes and organizes its CCAs.

Figure 12:
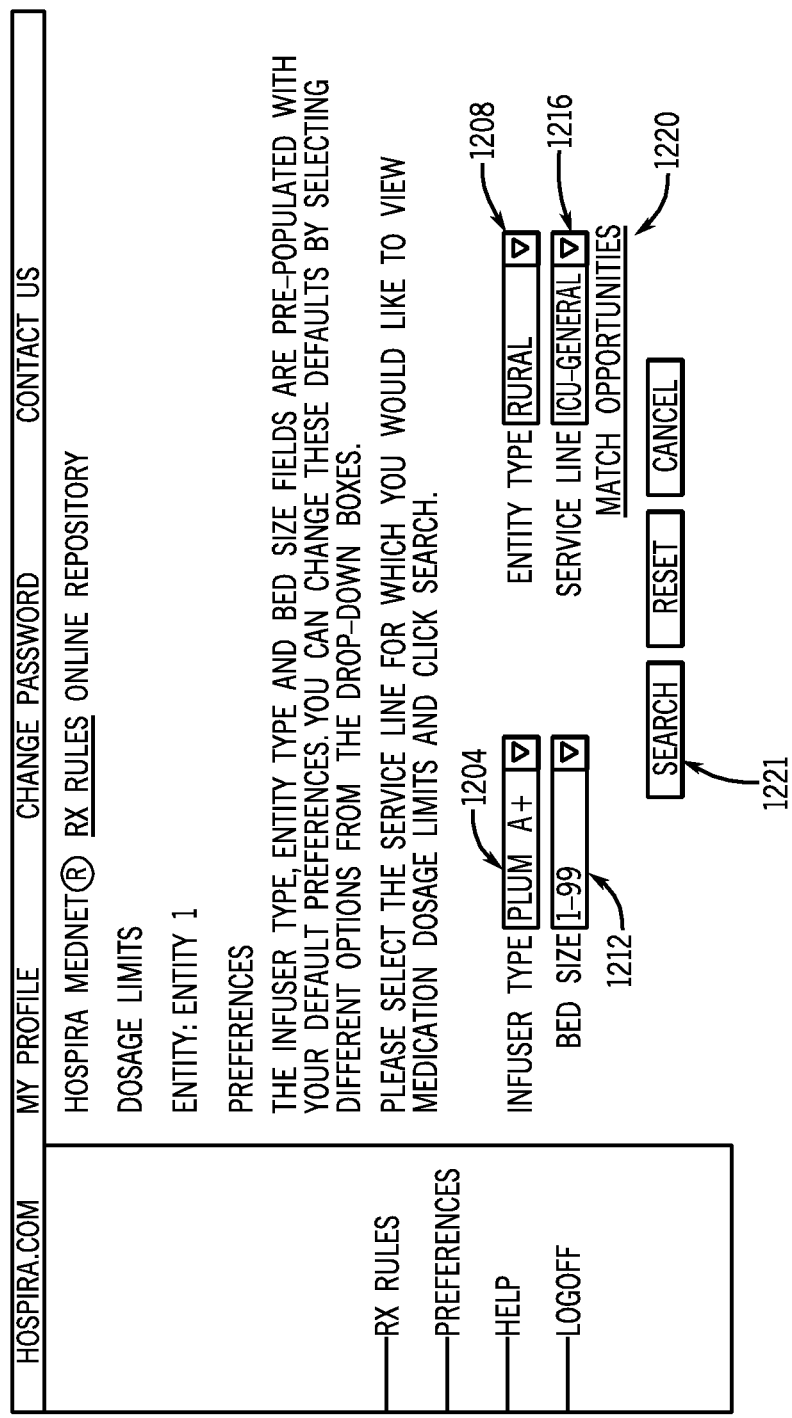
FIG. 12 is an interface screen display of selection functions for facility viewing of aggregated medication dosage limits configuration information preferences.

When an RXRULES or configuration information user type chooses the RxRules—Dosage Limits option, the user will be provided with an interface screen display similar to that which is shown in FIG. 12, for selecting search criteria or parameters to provide drug library information on at least dosage limits within pumps meeting the search parameters. Specifically, the interface screen display of FIG. 12 provides an infuser type drop down selection menu 1204 for selecting an infuser type similar to prior interface screen displays. The interface screen display of FIG. 12 further provides an entity type drop down selection menu 1208 for selecting an entity type similar to prior interface screen displays. The interface screen display of FIG. 12 also provides a bed size drop down selection drop menu 1212 for selecting a bed size similar to prior interface screen displays. In addition, the interface screen display of FIG. 12 further provides a service line drop down selection menu 1216 for selecting a service line. CCAs are particular to each institution/facility. However, service lines are the same across different institutions/facilities. Thus, each institution/facility can have one or more CCAs for each service line defined as a part of each institution/facility's defined parameters/information in memory 140. However, each CCA cannot have more than one service line as a part of each institution/facility's defined parameters/information in memory 140. Some examples of service lines are shown in FIG. 11 within the CCA lists 1104, 1108. Other examples of service lines include: behavioral health, bone marrow transplant, burn unit, emergency services endocrinology, eye ear nose & throat, geriatric, hematology, ICU (intensive care unit)—cardiac, ICU—general, ICU—medical, ICU—neonatal, ICU—pediatrics, ICU—surgical, medicine—adult, medicine—neonatal, medicine—pediatric, obstetrics/gynecology, oncology—adult, oncology—pediatric, orthopedics, pain management, rehabilitation, renal, skilled nursing, surgical—adult, surgical—cardiovascular, surgical pediatrics, transplant, trauma, urology, multiple service lines. Other specialty need service lines can include: anesthesia, out patient surgery, telemetry, special procedures, transfusion center, and/or ambulatory. In addition to the above-described drop down selection menus shown in FIG. 12, configuration/activity information application could be configured and the configuration/activity information database in the repository 140 could be configured to provide additional drop down selection menus for additional search criteria. For example, the interface screen display of FIG. 12 could include a drug risk level drop down selection menu (not shown), which could include selections such as high risk, medium risk, low risk, and/or all risk levels. By selecting a risk level other than all risk levels, the user will be further narrowing the results to more specifically target the searching being performed. The interface screen display of FIG. 13 could also be configured to include a risk level option and/or designation within window 1300. Other selections are possible as well.

Figure 14:
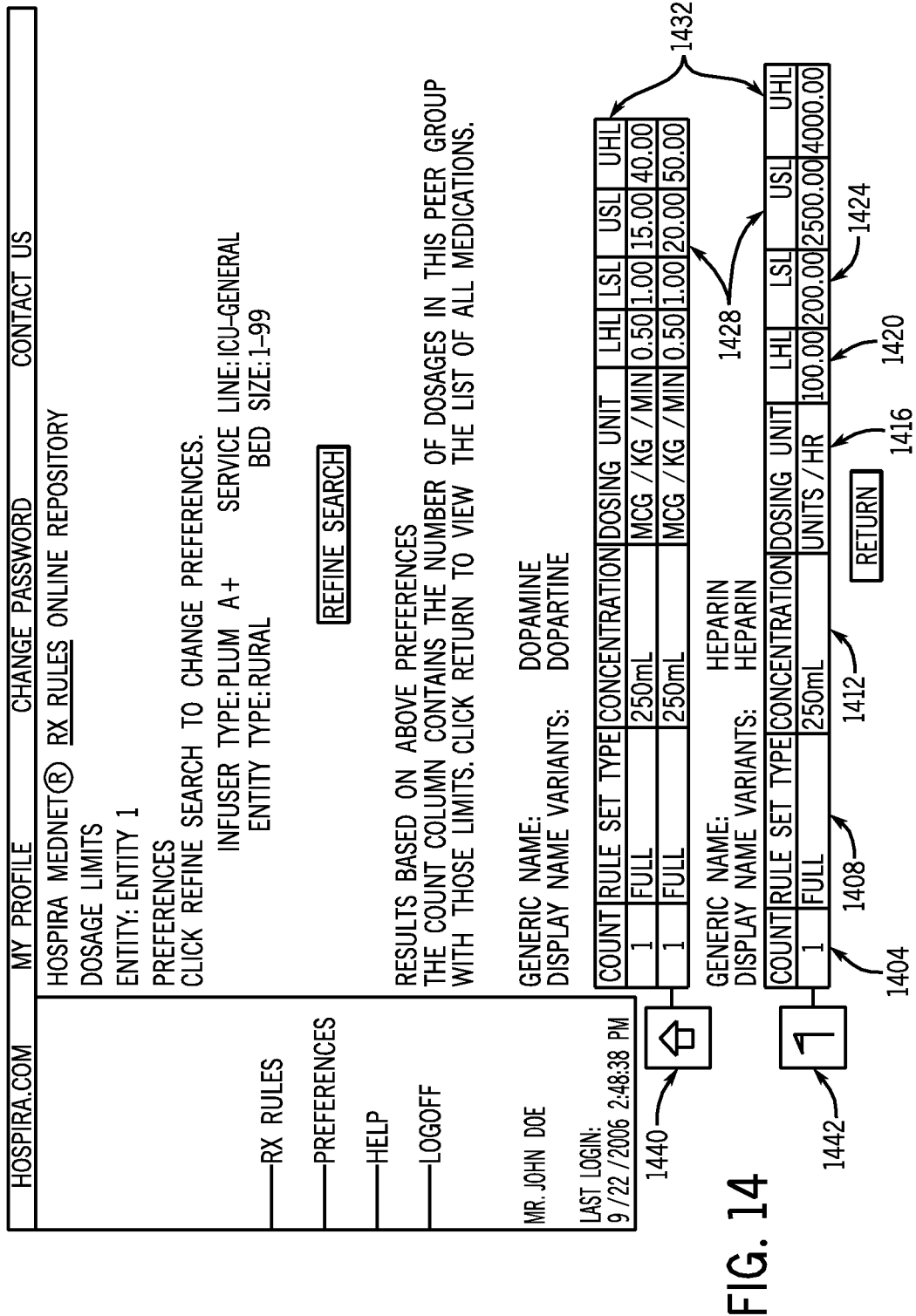
FIG. 14 is an interface screen display of results of particular preferences selected using the selection functions of FIGS. 12 and 13.

Once the above initial search parameters are selected, the user can select a "Search" button 1221 and the user will be provided with preliminary search results table 1300. The interface screen display of FIG. 13 provides the user with one or more generic medication name to select which medications the user would like to view configuration information, such as dosage limits for, which match the search criteria parameters within the database 140. The user can select all or less than all of the medication within the medication selection window 1300. Once the user selects the medication or medications the user would like to view the dosage limits for, the user can select the Show Report button, and the user will be provided with an interface screen display similar to that which is shown in FIG. 14. The interface screen display of FIG. 14 provides the user with a listing of each selected medication from the interface screen display of FIG. 13, with rows of configuration information. Based on the infuser type, each row of configuration information could include a count 1404, a rule set type (full, limited or partial, or label only) 1408, a concentration 1412, a dosing unit 1416, a lower hard limit (LHL) 1420, a lower soft limit (LSL) 1424, an upper soft limit (USL) 1428, and an upper hard limit (UHL) 1432. The count 1404 represents the number of matches based on the previously selected parameters from all configuration information stored in the data repository 140. The rule set type 1408 is specific to the PLUM A+ device and represents different levels of rule set configurations. The concentration 1412 represents the medication concentration contained in at least one drug library which is used to program a pump for that medication. The dosing unit 1416 represents the dosing unit of measure which is contained in at lest one drug library which is used to program a pump for that medication. The respective limits 1420, 1424, 1428, 1432 represent the safety limits that are contained in at least one drug library that is used to program a pump for that medication. If more than one row of configuration information appears for any one medication, this indicates that different drug libraries have different information for that specific medication, for the search parameters utilized. If drug risk levels are tracked in the database, the interface displays of FIG. 13 and/or FIG. 14 could also be configured display a risk level, such as high risk, medium risk, or low risk as a part of each row (not shown), for example if "all risk levels" is chosen for the search/reporting parameters within the interface screen display of FIG. 12 in a drop down menu. If a specific risk level is chosen as a part of the searching/reporting parameters, such as "high risk," the interface screen display could indicate this designation as a heading for the entire results displayed in FIG. 13 and/or FIG. 14. Other methods of configuring the interface screen displays and tracked/uploaded database information come to mind in view of the present description and figures. As shown in FIG. 14, the configuration information/activity information application 136, 136' and interface screen display can be configured to display a "home" icon 1440 adjacent each row of configuration information that includes configuration information from that user's institution or their "home" institution, as a part of the listed results. Also as shown in FIG. 14, the configuration information/activity information application 136, 136' and interface screen display can be configured to display a "flag" icon 1442 adjacent each row of configuration information that has already been displayed by that user in a configuration information report, such as a dosage limits report, during that user login session.

The configuration/activity information application and the interface screen display of FIG. 14 can also be configured to provide a comprehensive institution/facility medical device configuration library, for example a comprehensive drug library and infuser master settings library, selection box, button, or link (not shown) which, once selected, can cause comprehensive/consolidated configuration library for the listed institution/facility to appear on the interface screen display. In the embodiment having medication delivery pumps or infusers, some hospitals maintain a comprehensive configuration infuser library or database that includes most if not all of the possible ways in which infuser configuration libraries, such as drug libraries and master settings, in that institution/facility are configured. The user can be provided with the ability to see all of the ways in which the configuration libraries for the various infusers in the institution/facility are configured for a particular drug from the displayed comprehensive configuration information. The comprehensive configuration information can be sent, uploaded and/or file transferred to the central vendor/provider computer system 120 in a similar manner as the configuration/activity information described herein. In addition, a box, button or link can be configured to display a specific location within the comprehensive configuration library related to the drug or drugs shown within the results of selections performed within the interface screen displays of FIGS. 13 and 14, such as for example the drugs shown on the interface display screen of FIG. 14.

In addition or alternatively, the configuration/activity information application and the interface screen display of FIG. 14 can also be configured to provide a master medical device settings, for example a master infuser settings, selection box, button, or link (not shown). Once selected, additional or all of the configuration library information for the particular infuser in the institution/facility relating to a particular infuser will appear on the interface screen display of FIG. 14 or an additional interface screen display (not shown). For example, the interface screen display of FIG. 14 can provide, through a box, button or link, the user with the ability to request and display master infuser settings for each infuser, such as volumes for alarms, tones for alarms, tones for alerts and other events, etc. The master medical device settings, such as the master infuser settings can be sent, uploaded and/or file transferred to the central vendor/provider computer system 120, 120' in a similar manner as the configuration/activity information described herein, for use in the configuration/activity information application.

Within the central configuration/activity database stored in the central repository 140, 140' several institution maintenance database tables are provided for storing institution configuration information, such as health care system/facility ID, customer ID, AHA (American Hospital Association) number, HIN (Hospital Identification Number), health care system/facility name, health care system/facility address, city, state, zip code, country, phone number, e-mail address, contact name, registration date, FTP (or extraction) sequence number, peer group, number of beds in the health care system/facility, whether the health care system/facility is active, a health care system/facility server list (identification of all servers within the health care system/facility), and, if applicable, a facility list (all facilities which are a part of the health care system). When the institution maintenance interface screens are used to enter and/or modify this information, the institution maintenance database tables are respectively modified according to the administrator's key strokes. After each FTP action or other extraction to upload an institution's configuration/activity information to the central vendor computer system, the FTP or extraction sequence number is incremented to keep track of the uploads that have occurred. The bed size of a health care system is the sum of all of the beds at all of the facilities within a health care system.

In one embodiment, old configuration information and activity information database tables and data therein will not retained for more than a predetermined period of time within the configuration/activity information aggregation server 132. Old records will be archived within the aggregation server 132, 132' and will be copied to offline storage periodically, such as onto tape or other storage media backup. The configuration information, such as the drug libraries will be deleted and reloaded fully every time for each institution and device type. One reason for using this embodiment is that typically only one configuration library is used within one device/pump, and, at most, only one configuration library, per device type, can be created and active within an institution at any time. In one embodiment, raw data within the aggregation server 132, 132' FTP server 124, 124' or other computer, is retained indefinitely. In other embodiments, summarized results, as provided herein, can be retained for eighteen months or indefinitely.

In a further embodiment, when the customer runs a configuration information report, such as a CCA distribution or dosage limits report within the RXRULES application described herein, the configuration information/activity information application 136, 136' can be configured to allow a customer run a comparison, similar to BENCHMARKING comparisons described herein, of one or more of the results of the configuration report vs. configuration information from within other groupings or cumulative groupings of configuration information, and related activity information to such other configuration information. For example, referring to FIG. 12-14 again, a customer or user can run a dosage limits report with preference of one type of infuser, one type of entity, one type of service lone and one size institution. The results provided with such preferences can then be compared to all or other infusers, all or other entities, all or other service line types, all or other size institutions, and/or all or other peer groups. The results can be presented in a manner similar to results and/or charts provided within FIGS. 5A-6E. Continuing with this embodiment, when the customer runs a configuration information report, such as a CCA distribution or dosage limits report within the RXRULES application described herein, the configuration information/activity information application 136, 136' can be further configured to allow a customer to modify one of the individual result items, such as modifying soft limit within a dosage limits report. The configuration information/activity information application 136, 136' can be configured to allow a customer to run a comparison or to rerun a previously run comparison, similar to the BENCHMARKING comparisons described herein, of the modified result(s) of the configuration report vs. configuration information from within other groupings or cumulative groupings of configuration information and/or vs. related activity information to such other configuration information. In this way, the customer will be able to determine the effect of the modification of the parameter, such as a modified soft limit on the amount of alerts which are generated utilizing such modified soft limit.

It should be understood that the present set of configuration information/activity information application 136, 136' functions, such as the BENCHMARKING and/or RXRULES functions described herein, can be utilized for configuration/activity information for other types of infusion devices, as well as for monitoring devices, ventilators, syringe pumps, and other medication delivery and/or monitoring devices.

Referring to FIGS. 16-23, a set of administration screens can be provided to view, configure and/or modify system settings stored within the central configuration/activity data repository 140, 140', for each institution having access to the present invention. An administrator at the vendor/provider can access the administration screens in a similar manner as the other interface screens for users described above, through an administration client computer (not shown) accessing the configuration/activity information application 136, 136' residing on the central provider computer system over the Internet. For example, one or more interface screens from the configuration/activity information application can be provided for system maintenance (FIG. 17), institution/facility maintenance (FIG. 18), manage users (FIGS. 19-20), infuser maintenance (FIG. 21), peer group maintenance (FIG. 22), and general settings (FIG. 23) through the administration client computer. Each of these maintenance interface display screens can be navigated to through an administration options interface screen 1600 shown in FIG. 16, by clicking a system maintenance link 1602, an institution/facility maintenance link 1604, a manage users link 1606, an infuser maintenance link 1608, a peer group maintenance link 1610, and a general settings link 1612, respectively.

Referring to FIG. 17, a health system or institution maintenance interface screen 1700 allows an administrator to view, configure and/or modify system information, such as institution ID 1702, institution name 1704, institution address 1706, institution city 1708, institution state and zip code 1710, institution phone number 1712, institution e-mail address 1714, number of beds in the institution 1716, whether the institution is active 1718, an institution server list 1720, and an institution facility list 1722. A vendor administrator can look up an institution through an institution search screen by institution name, city, state, phone number, or through some other information which can be used to identify an institution. This can be performed by entering this information into input fields 1730 and pressing a search button 1740. A results screen is then displayed on the client computer, which can display a table of the above and other institution information to which the administrator can view and configure. The administrator can be provided with one or more "edit" buttons 1750 to configure at least some of this information, and can be provided with "add" button 1760 to add new institutions. Once the edit button is selected, the administrator will be provided with access to each of the fields in the table for entering and/or modifying information within each field within the table.

If an administrator selects the server list field within the institution maintenance interface screen, an additional server list table (not shown) appears which lists all of the servers for the institution. The administrator can select an "edit" button to modify the listed servers or select an "add" button to enter new servers for the institution. Each server listing provides a server ID number, a configuration information sequence number (the number of uploads which have occurred for configuration information) and an activity information sequence number (the number of uploads which have occurred for activity information). The configuration information sequence number and the activity information sequence number are typically the same, and would be the same if the configuration information and the activity information had been uploaded together each time an FTP/extraction activity had occurred. However, in one embodiment, FTP activity, extraction or upload can occur for each type of information separately, which would likely cause the sequence numbers to be different.

If an administrator selects the facility list field within the institution maintenance interface screen, an additional facility list table (not shown, but is similar to FIG. 18) appears which lists all of the facilities for the institution. Each facility listing provides a facility name, server ID, address, city, state, peer group type, number of beds, and a location description of the facility for the administrator to provide as an easy way to refer to the facility. A separate set of interface screens are provided for adding and/or modifying facilities, as described below.

Figure 18:
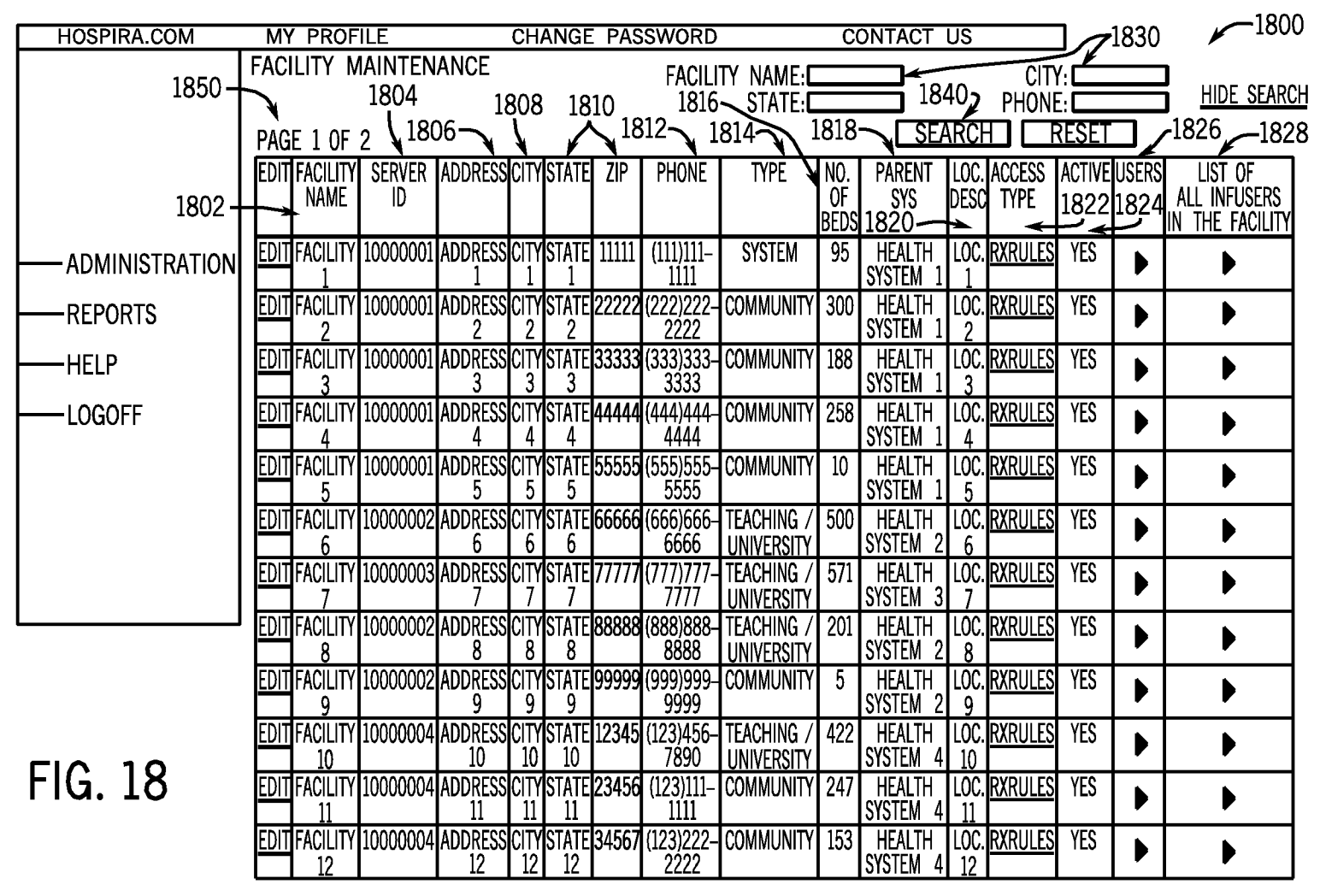

Referring to FIG. 18, a facility maintenance interface screen 1800 allows at least a vendor administrator to view, configure and/or modify facility information, such as facility name 1802, server ID 1804, address 1806, city 1808, state and zip 1810, phone number 1812, facility type 1814, number of beds in facility 1816, parent institution (or facility in one embodiment) 1818, location description 1820, access type 1822, whether the facility is active 1824, a users listing 1826, and an infusers listing 1828. Some of these functions are available to a institution administrator as well. An appropriate administrator can look up a facility through a facility search screen by facility name, city, state, phone number, or through some other information that can be used to identify a facility. This can be performed by entering this information into input fields 1830 and pressing a search button 1840. A results screen is then displayed on the remote client computer, which can display a table of the above and other facility information to which the administrator can view and configure. The administrator can be provided with "edit" buttons 1850 to configure at least some of this information, and can be provided with "add" button to add new facilities. Once the edit button is selected, the administrator will be provided with access to each of the fields in the table for entering and/or modifying information within each field within the table.

If an administrator selects the users list field within the facility maintenance interface screen, an additional users list table (not shown, but is similar to FIG. 19) appears which lists all of the users for the facility. Each user listing provides the name of the user, the user address, city, state, country, work phone, user type (configuration information user and/or activity information user), an expiration date for user to have access to configuration information and an expiration date for the user to have access to activity information. The assignee of the present invention has named the configuration information user an RXRULES user (or HOSPIRA MEDNET-MEDS user) and has named the activity information user a BENCHMARKING user, as may be shown in one or more figures. A separate set of interface screens, or manage users interface screens, are provided for adding and/or modifying users, as described below.

If an administrator selects the infusers list field within the facility maintenance interface screen, an additional infusers list table (not shown, but is similar to FIG. 21) appears which lists all of the infusers for the facility. Each infuser listing provides the infuser ID, the institution or system name, the facility name, a compartment index number, a CCA ID, an infuser type, and a download state number. The compartment index and a download state number represent different infuser pump mechanisms and the current state of a drug library download respectfully. The CCA ID represents a clinical care area identification, such as for example a general intensive care area or a pediatric intensive care area. The infuser type may be dependent on the infuser vendor or other medication delivery device vendor. For example, the assignee of the present invention is also a vendor of medication delivery pumps under at least the names of PLUM A+ and LIFECARE PCA. Thus, in one embodiment, the infuser type can be PLUM A+ and LIFECARE PCA or other infuser or pump type which an institution and/or facility may be using. A separate set of interface screens, or manage infusers interface screens, are provided for adding and/or modifying infusers, as described below.

Referring to FIG. 19, a manage users interface screen 1900 allows an administrator to view, configure and/or modify user information, such as user ID 1902, user name 1904, address 1906, country 1908, work phone number 1910, cell phone number 1912, user type 1914 (configuration information access type and/or activity information access type), access type 1916, and expiration date 1918 for the user having access to the configuration/activity information application for each type of access (BM for BENCHMARK user access, and RxR for RXRULES user access). An administrator can look up or search for a user or group of users through a user search screen by user ID, user name, user address, user country, user work phone number, user cell phone number, user type, and/or expiration date, or through some other information that can be used to identify a user or group of users. This can be performed by entering this information into input fields 1930 and pressing a search button 1940. A results screen is then displayed on the remote client computer, which can display a table of the above and other user information to which the administrator can view and configure. The administrator can be provided with an "edit" button to configure at least some of this information. Another example can include a user ID being highlighted and linked to an edit screen for each user to configure and modify a user table entry, as shown in FIG. 19 with the underline of each user ID 1902. A new user entry link can be provided or a user "add" button to add new users can be provided, which can be linked to a new user entry screen that will appear upon clicking on such link. Once the edit, add or other button or link is selected, the administrator will be provided with access to each of the fields in the table for entering and/or modifying user information within each field within the user table.

Referring to FIG. 20, the user entry or modification screen 2000 has various fields for entering/modifying information about the user. A user ID number is assigned to the user by the configuration/activity information application and is shown, and the fields can include but are not limited to first name 2002, last name 2004, middle name 2006, prefix 2008, suffix 2010, street address 2012, city 2014, state 2016, country 2018, zip code 2020, work phone 2022, cell phone 2024, work fax 2026, work e-mail address 2028, vendor provided customer ID number 2030, one or both user types 2032 (as explained above), additional information provided within a text box 2034, secret password validation question 2036, secret password validation answer 2038, account locked/account active check off box (not shown), expiration date for access for each type of access (not shown), and a table of all facilities (not shown) within the specific institution of the user along with a check off box for each such facility indicating whether the user is assigned to each specific facility listed within the table. A link to add an institution and/or facility can be provided from this screen as well as a reset password button for resetting a user password, and for the user to be automatically e-mailed a new password. "Save", "cancel" and other buttons can be provided for typical data management functions. A dropdown list can be provided for selecting a user type 2030. The selection can include configuration information user (RXRULES), activity information user (BENCHMARKING), both of these types together, institution administrator, vendor administrator, superuser (combination of configuration information user (RXRULES), activity information user (BENCHMARKING) and institution administrator), and helpdesk. A drop down list of secret questions to use can also be provided for providing typical standard questions to ask a user for password validation.

Figure 21:
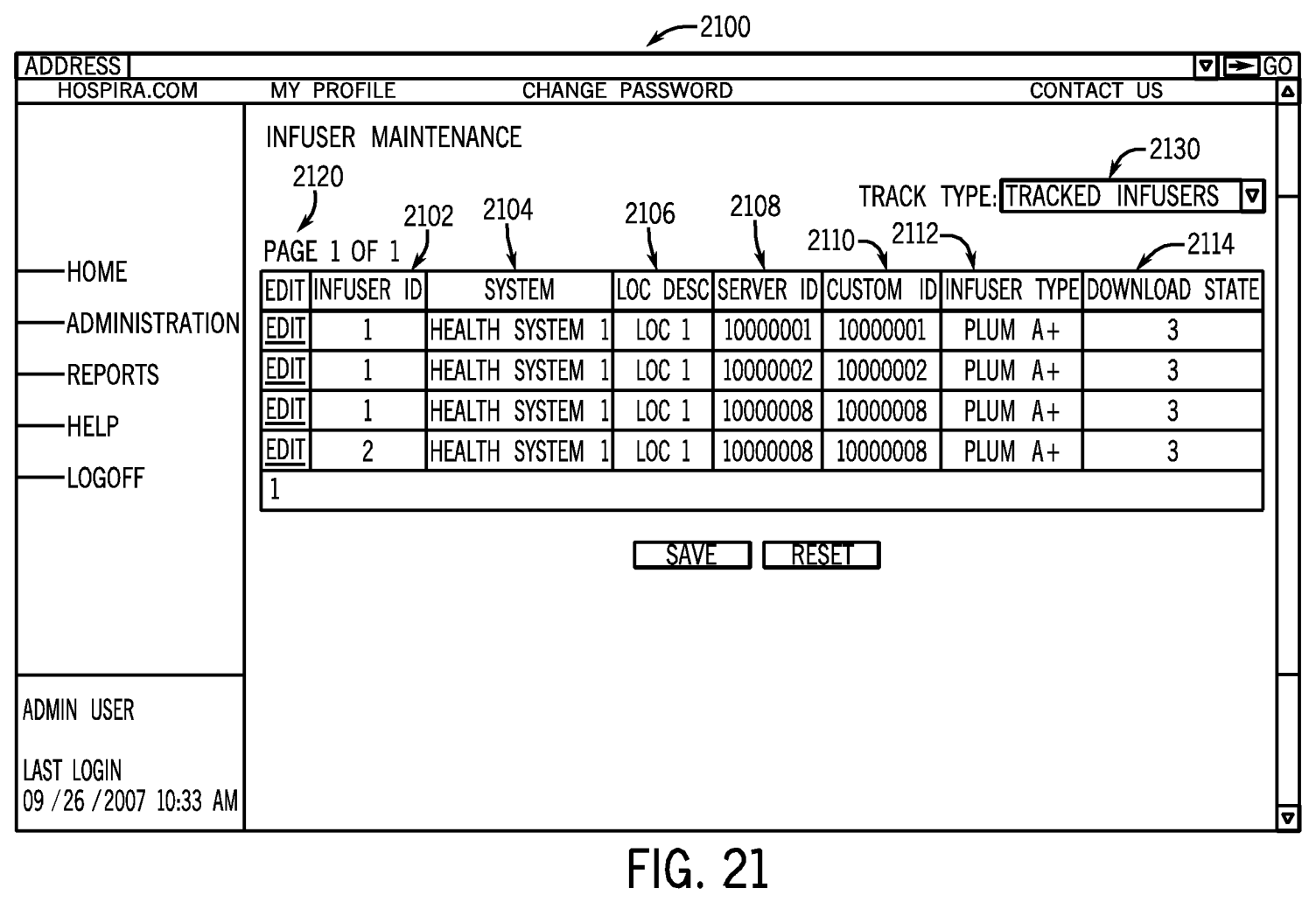

Referring to FIG. 21, a manage infusers interface screen 2100 allows an administrator to view, configure and/or modify infuser information, such as infuser ID 2102, system name 2104 of the medication management and/or delivery system in which the infuser is communicating and resides, location description 2106 providing the location the infuser within a facility such as a clinical care area name, the server ID 2108 of the server to which the infuser is communicating, the customer ID 2110 of the customer institution where the infuser is located and is being used, an infuser type 2112, and a download state 2114. The download state 2114 represents the current state of a drug library download. An administrator can view the infusers by selecting a manage infusers button. The infuser information can be shown in table format and the administrator can be provided with an "edit" button 2120 at the beginning of each table entry to configure at least some of the above information. The manage infusers interface screen can also allow for the administrator to select to view all "orphaned infusers" or all "tracked pumps" through as track type selector 2130. An orphaned infuser represents an infuser that has not been assigned a location or provided with a location description. Tracked pumps represent pumps with location descriptions. After editing of the table entries which the administrator wishes to configure, the administrator can select a save button to save all of the edits to memory. A reset button can be provided to reset all editing back to prior to any edits being performed and not save any edits to the infuser table entries. Once the edit button is selected, the administrator will be provided with access to each of the infuser fields in the table for modifying infuser information within each field within the infuser table.

Figure 22:
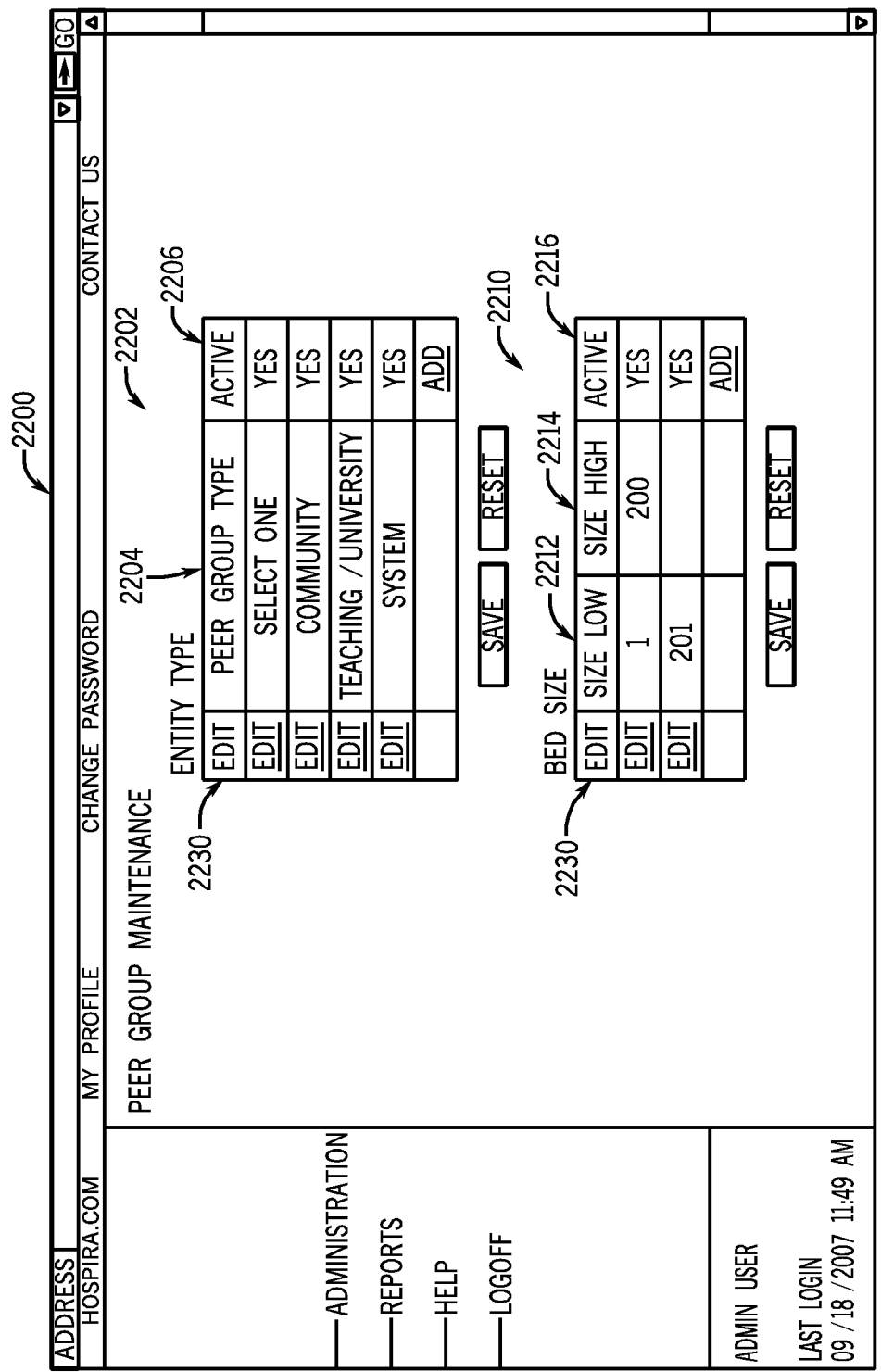
FIG. 22 is a peer group maintenance interface screen for viewing, configuring and/or modifying peer group information.

Referring to FIG. 22, a manage peer groups interface screen 2200 allows an administrator to view, configure and/or modify peer group information, such as entity type 2202 and bed size 2210. Entity type 2202 defines each institution as one of rural, community, teaching/university, multi-hospital health system, or with some other designation that the configuration/activity information application can be programmed with for use by customer institutions. Bed size 2210 defines the number of beds (for patients) within a health care system, including all facilities within a health care system. The manage peer groups interface screen can display entity types 2202 in a table with peer group name 2204 and active/inactive field 2206. The manage peer groups interface screen also can display bed sizes 2210 in a table with size low 2212 (low end of a range), size high 2214 (high end of a range) and active/inactive field 2216. An administrator can view the entity type table and/or bed size table by selecting a manage peer groups button. The peer group information can be shown in table format and the administrator can be provided with an "edit" button 2230 at the beginning of each table entry to configure and/or modify the above information. After editing of the table entries which the administrator wishes to configure, the administrator can select a save button to save all of the edits to memory. A reset button can be provided to reset all editing back to prior to any edits being performed and not save any edits to the peer group table entries. Once the edit button is selected, the administrator will be provided with access to each of the peer group fields in the table for modifying peer group information within each field within the entity type table and/or bed size table.

Referring to FIG. 23, a general settings interface screen 2300 allows an administrator to view, configure and/or modify general settings, which will customize the system in particular ways for the institutional users of the configuration/ activity information application of the present invention. In particular, the general settings interface screen allows the administrator to customize certain parameters, such as the default values for the expiration of a configuration information user's access to the application 2302 and of an activity information user's access to the system 2304, a default value for the how often a user's password must be changed 2306, default questions to use for password security verification 2308, the name of the entity/user to display within certain information interface screens described herein 2310, how long to retain raw configuration/activity information within system memory received from each institution 2312, how long to retain summary configuration/activity information within system memory regarding each institution's raw configuration/activity information within system memory, the minimum number of entities in a peer group that is needed to perform a BENCHMARK comparison report 2314, the maximum number of institutions/facilities that can be selected in an RXRULES CCA distribution report 2316, and/or the maximum number of drug names that can be selected in the RXRULES dosage limits report 2318. The above parameters that an administrator can customize are only examples. Many other examples would be apparent to one of ordinary skill in the art in the context of the present detailed description. Again, general parameters can be shown in table format, with each entry having a parameter name, a parameter type, a parameter description, a parameter value, and an active/inactive designation. The administrator can be provided with an "edit" button 2330 at the beginning of each table entry to configure and/or modify the above information. After editing of the table entries which the administrator wishes to configure, the administrator can select a save button to save all of the edits to memory. A reset button can be provided to reset all editing back to prior to any edits being performed and not save any edits to the general parameter table entries. Once the edit button is selected, the administrator will be provided with access to at least the parameter value and active/inactive designation fields in the table for modifying the general parameter information within each field within the entity type table and/or bed size table. The administrator can be provided with access to configure and/or modify the other fields as well.

The administrator can also be provided with access to a user expiration report (not shown). A link or button can be provided to launch the user expiration report, which can identify the users and the respective user account information, in table format, that are set to expire in the next week or within the next month, or some other user selectable time frame. The results can be provided in a manner that will allow the administrator to select a specific user and call up the user account information for a particular user by selecting a link (on a user ID or some other location). The administrator can then extend the expiration of such user as the administrator sees fit. Of course, the vendor/provider administrator may choose to delegate or allow the institutional user rights to modify or maintain some of their own information, settings, profiles, etc.

In one embodiment of the present invention, a notification, such as by e-mail or other communication, can be provided to customer institutions and/or facilities based on an institution's pre-defined alert limits. For example, the configuration information/activity information application or other application within the central vendor or provider computer system 120, 120' can be adapted to perform regular comparisons of activity information and/or configuration information of devices such as pumps within one institution or facility with activity information and/or configuration information of devices such as pumps within a particular peer group or other group designated by the institution and/or facility. The institution/facility can provide the configuration information/activity information application or other application with alert criteria, such that when the comparison result is out of range in relation to the alert criteria, a communication to the institution or facility can automatically be generated by the configuration information/activity information application or other application and sent to an administrator's or user's e-mail within the database 140 for the institution/facility. Thus, an institution and/or facility user can enter, store and have one or more of the applications described herein execute and/or generate medication practice alert notifications based on an institution's and/or facilities pre-defined alert limits. In one example, an institution could assign a predetermined value, such as 10% to the pre-defined alert of "percentage of edits as a percentage of total programs." For this example, whenever the institution/facility exceeds this predetermined value (set at 10%), a notification is sent, such as by e-mail, text message, pager, etc. to inform a user, such as an administrator or pharmacist that an issue may exist with respect to the rule set(s) for the configuration library. In another example, assume a medication library has an entry for a particular medication, such as Heparin, that has an upper hard limit of a predetermined value, such as 25000 units/hr. If the predetermined value, such as 25000 units/hr. falls outside of the statistical norm or pre-defined threshold, a notification can be sent to appropriate personnel, such as an administrator or pharmacist for resolution.

The performed comparison can also be statistical analysis with peers or with other groupings. In one example, an alert can be generated if the device/pump activity information indicates that the institution/facility has a drug library utilization rate, soft limit override rate, etc. that is more than specified number of standard deviations in separation from their peers. The same principle could be applied to configuration information, such as drug library limits or other infuser configuration settings that may be contained within the configuration library or elsewhere. The administrator and/or user could establish their own specific alert criteria or the system could offer a plurality of selectable criteria in drop down menus, as one of skill in the art would understand from the present description. Alternatively, the system administrator may establish the alert criteria to be applied for all subscribers or the programming code may use predefined criteria.

In a further embodiment, and as introduced previously herein in relation to FIG. 1B, instead of an institution/facility having a configuration library development application hosted within its own medication delivery system or systems, a remotely hosted configuration library development application (RCLDA) can be hosted by a one or more remote computers or RCLDA servers 182, or cluster(s) of servers, including use of an RCLDA database, either in the control of the vendor of all or portions of medication delivery systems or hosted by a third party hosting vendor. Specifically, with reference to FIG. 1B, and now FIG. 15 as well, a plurality of remote computers 1500, 1504, 1508 can be provided for hosting remote configuration library development applications (RCLDAs) therein for creating, editing, developing, and/or maintaining configuration libraries, such as drug libraries for use within medical devices, such as medication delivery pumps. These remote configuration library development applications can be accessed by client computers from each institution/facility, such as through pharmacy client computers 1512, 1516, 1520 over a network such as the Internet 1524. The remote configuration library development application can have similar functionality as existing HOSPIRA MEDNET application functionality, provided by HOS- PIRA, INC., the assignee of the present invention. In one embodiment, each "HOSPIRA MEDNET" server can run SQL SERVER software for database creation, having similar database tables as described herein, from client sites throughout the country or the world, via the Internet 1524. Each physical server can be set up to run multiple virtual servers using VMware's ESX server. This will allow, at the low end, six virtual HOSPIRA MEDNET/SQL servers to run on each physical machine.

It should be appreciated that the RCLDA and the central vendor or provider computer system 120 of FIG. 1A can both be provided with the same system, server or group of servers, or from completely separate servers, as shown in FIG. 1B. Nonetheless, it should be appreciated that the functionality for two or more of the software applications shown in FIG. 1B can be viewed and utilized from the same client computer 150, 150', 1512, 1516, 1520 at the same time. Specifically, a customer can utilize the configuration/activity information application and the RCLDA from the same client computer 150, 150', 1512, 1516, 1520 at the same time. For example, a customer may wish to run the configuration/activity information application on one side of the screen of their client computer 150' and check how its "peers" set up limits for certain drugs for certain CCAs, and at the same time may wish to run the RCLDA on the other side of the computer screen of their client computer 150' and create of edit the same drug for the same or similar CCA within their own drug library for later installation into an MMU and into a medication delivery device, such as an infusion pump.

In addition, functions from each of these applications can be combined in a manner to allow for efficient reporting, benchmarking and development functions to occur on one interface display screen or closely related screens, providing for effective use of the reporting and benchmarking functions described above to be used for creating, editing, developing, and/or maintaining of configuration libraries. Specifically, as shown and described in relation to FIG. 1A and FIG. 1B, client computer 150, 150' can be used to access and use the configuration/activity application 136, 136' and at least the reporting and benchmarking functions therein. A direct link 190 can be provided, and in FIG. 1B, to directly connect the RCLDA 182 with the configuration/activity application 136' to allow for the functions of each of these application to be combined without having to separately run these applications on the same screen of a client computer 150, 150' through a "split screen" or dual window arrangement. Thus, a single application can be provided which integrates one or more of functions of each of the RCLDA 182 and the configuration/activity application 136', through the direct link 190 shown in FIG. 1B. Thus, in one embodiment, functions of the RCLDA 182 can be made available to a user accessing the configuration/activity application 136' through client computer 150', web access application/server 160' and second firewall application/server 170', through the direct link 190 communicatively connecting the RCLDA 182 and associated RCLDA database 184 with the configuration/activity application 136'. Likewise, in the same or other embodiment, functions of the configuration/activity application 136' can be made available to a user accessing the RCLDA 182 through a client computer 150', through customer server 108' or directly through Front End RCLDA server 180, and first firewall application/server 128', through the direct link 190 communicatively connecting the configuration/activity application 136' with the RCLDA 182 and associated RCLDA database 184. As indicated herein, the configuration/activity application 136' and the RCLDA 182 and associated RCLDA database 184 could be combined on a single server and/or the functions of the configuration/activity application 136' and the RCLDA 182 could be combined in a single computer software application. In this later embodiment, various functions can be integrated to allow a customer to achieve improved efficiencies, such as faster development of configuration information, for example drug libraries, and/or the development of more reliable configuration information, for example drug libraries.

Once the pharmacy or other institution/facility user has completed the configuration library development/changes, the library can be downloaded directly to an institution facility's medication delivery system or via an import list. Thus, a pharmacist or user at the institution/facility or elsewhere can use the remote configuration library development application to develop configuration libraries without having a medication delivery system, MMU, medical devices, medication delivery pump or other parts of a medication delivery system installed at their institution/facility. This is particularly useful when an institution/facility has purchased a medication delivery system, but it has not been installed yet or the installation has not yet been completed. While the installation is taking place, the user can begin and complete the development and creation of the configuration libraries using the remote configuration library development application, as well as using the reporting and benchmarking functions of the present invention described herein. As soon as the installation is completed, the configuration libraries, such as drug libraries, which are likely already ready for use in view of ability to use the benchmarking and/or reporting functions described herein as a part of the library development, will be ready for downloading into the medical devices, such as medication delivery pumps, for fast and efficient start-up and use of the medication delivery system, MMUs and medical devices associated therewith. Thus, configuration libraries, such as drug libraries, developed using the RCLDA 182, and residing in the RCLDA database 184 can be downloaded through the first firewall application/server 128' and through the Front End RCLDA server 180 and into a customer server/database 108' for use by the customer in operation of the customer institution's medication delivery system. Likewise, in the context of one embodiment of FIG. 1B herein, developed configuration libraries, such as drug libraries, developed using the RCLDA 182 can be "loaded" into the RHCS 182, and respective RHCS database 184. If the RCLDA 182 and the RHCS 182 reside on the same server and their respective databases reside on the same memory device, then loading may simply entail making the RCLDA database 184 available to the RHCS 182 and respective functions for use by the RHCS 182.

Referring again to FIG. 14, additionally or alternatively, the configuration/activity information application and the interface screen display of FIG. 14 can also be configured to allow a user to select one or more configuration library rule sets (each row shown in FIG. 14 is one set or at least a portion of one rule set), and place a copy of the rule set(s) or some identifier associated with the rule set within an electronic shopping cart for later use. From time to time, or upon exiting of one or more of the screen displays, the user can be prompted and asked if the user would like to send the shopping cart items to a local storage medium, a remote medication delivery system and/or pharmacy therein, to an e-mail address selected or entered by the user, to a local or remote configuration library development application (RCLDA) for use in developing a new medical device configuration library and/or modifying an existing medical device configuration library, using the rule set(s) placed into the shopping cart. These shopping cart rule sets can also be used to create and/or add to master or comprehensive institution/facility configuration libraries, such as master formulary lists or CCA sub population lists. Alternatively, as understood from at least the description relating to FIG. 15 above, a configuration/activity information application can be configured to allow the user to select a copy of one or more rule sets and either "drag and drop," "paste," or perform some other action to directly copy the rule set(s) into the configuration library being created and/or modified.

In one embodiment, the user will have selected a shopping cart medications list name or file name to add items drug entries to, and will have selected one or more medication entries to add to such medications list, within the above or other interface screens, by highlighting one or more drug entries and then clicking on an "add to shopping cart" button. Once all selections have been completed, additional shopping cart functionality can be provided by selecting on a shopping cart icon or link (not shown) in the main RXRULES menu, such menu being shown in the left hand column of FIGS. 7-14. After selecting the shopping cart link, user can be presented with a shopping cart interface screen, and the user can be requested to select or indicate which medication list (file name) to be used when importing the shopping cart selections into the drug or medication library database. A default medications list can be provided (one that is used first or most often, etc.) and/or a drop down list of medication lists can also be provided. The user can also be provided with a "browse file(s)" option to select a medications list file to use when performing the import of the shopping cart into the drug library database. The shopping cart interface screen will also allow the user to select an infuser type from a drop down menu or other selection means. After selection of an infuser type, the user can be presented with a list of shopping cart items for the selected infuser, which will indicate whether each shopping cart selection is from the customer's/user's own institution. This indicates or provides an alert to the user that the user will need to ensure that the CCA exists in their own institution's server and database 108, 108'. The user is also provided with an XML file generation option to generate an XML file to be used to update and transfer the selected drug entries to the institution server and database 108, 108'. The ability to use this XML file generation function and perform drug entry transfers to a customer database 108, 108' can be controlled by only providing such functionality to higher user levels. These file transfers can instead be made to the RCLDA server 182 for remote creation of drug libraries through the communication link 190 or other communications transfer, for example when a medication delivery system has not yet been installed in an institution.

In a further embodiment, as a user is creating one or more rule sets from scratch or by using existing rule sets from existing medical device configuration information in the memory 140, a user may wish to compare a proposed rule set against established rule sets that are in use in another facility or other facilities within a user's own institution or another facility and/or other facilities outside of the user's institution. A proposed rule set interface screen within the configuration/activity information application or RCLDA 182, provided for example by way of the direct link 190 between the RCLDA 182 and the configuration/activity information application 136', can be provided to either allow a user to enter a proposed rule set or copy and paste a rule set from a configuration information library that is in the process of being developed, and use comparison functions, such as the BENCHMARKING functions described herein, to compare a proposed rule set to existing configuration and/or activity information data. For example, a user may wish to know statistically whether the proposed rule set or portion thereof, for the user's entity falls desired ranges within their peer group. In one example, the user can enter a proposed upper limit and request comparison using drop down selection menus described herein, and the system may provide an output as follows: The entered Upper Soft Limit is in the top $50^{th}$ percentile of the Upper Soft Limits currently in use by other institutions and/or facilities (in your peer group/for all peer groups/for a particular CCA/for all CCAs/etc.).

In a further embodiment, the configuration/activity information application, the interface screen display of FIG. 14 or other interface screen display generated therefrom, or other interface screen display in another application, such as the remote configuration library development applications can also be configured to allow a user to select and perform the following. When viewing a rule set, the user can be provided with the ability to view or compare the rule set versus the number of alerts for the rule set, in order to statistically predict an outcome for the rule set from an alert perspective over various timeframes. This comparison can further broken down by time frame, by peer group, by CCA, and/or by some other preference. This information will assist the user in creating rule sets for the medical device configuration libraries. In a further embodiment, these applications and screen displays can be configured to allow the user to select and perform the following. When viewing an institution/facility that has a high number of alerts for a particular medication, the use can be provided the ability to "drill down" to view the specific medication rule set and compare the rule set in question to other rule sets that have a lower percentage of alerts, or just list the rule sets which have a lower percentage of alerts for that medication. The configuration information/activity information application 136, 136' can be further configured to allow a user to then choose, select or copy a rule set with less alerts according to one or more of the above embodiments described herein and use this new rule set within the medical device configuration library for their institution. This functionality would assist in modifying clinical behaviors and/or rule sets at a particular institution.

The configuration information/activity information application 136, 136' as well as the aggregation application 132, 132', and other applications described herein, can be provided for use in English and other languages. In one embodiment, although the "front end" or visual interface screen aspects of the various applications can still be in English, configuration/activity information data from institutions within foreign (non-US) countries can be received and aggregated and included with the configuration/activity information database 140, 140'. Thus, when BENCHMARKING, RXRULES and other functionality described here in provided to a user/customer, such functionality can be provide results which encompass the configuration/activity information data from institutions within the foreign countries. Likewise, a country preference/parameter can be provided to allow a user to select and run reports and receive configuration/activity information from institutions only in such countries.

It should further be noted that while graphical reporting of configuration/activity information has been shown in the figures and described herein, more basic text reporting can be provided in addition to or instead of such graphical reporting.

When a user/customer at an institution is using the interface screens described herein to create and/or edit configuration information for a medication delivery system, such as a drug library for downloading into and use within medical devices, such a user may need help in performing this and other functionality provided through such interface screens. The vendor can provide a vendor telephone "hotline" to customers to talk to a vendor personnel to assist such a user in performing these and other functions. Specifically, the user can call a predetermined number provided within a user manual, through the interface screen(s), and/or through a link to a vendor website through which the user can be provided a telephone number for the "hotline." When the user calls the "hotline" number, the vendor personnel can assist the user by logging into the user's account and viewing exactly what the user is viewing through the interface screen(s). The vendor personnel can also view exactly what actions the user is taking (movements and actions of the cursor/arrow and keystrokes) and can determine if the user is taking any incorrect actions. The vendor personnel can inform the user how to take actions, if the user is making any mistakes or asks the vendor personnel how to perform such actions. Moreover, using existing software provided by companies such as CITRIX, the vendor personnel can take over control of the user's interface screens and perform the user actions for the user, while the user watches the vendor personnel take such actions. In one embodiment, the vendor personnel can be a vendor pharmacist and the user can be a customer trying to obtain summary information, such as BENCHMARKING and/or RXRULES reports, for the configuration/activity information database 140, 140' through the configuration information/activity information application 136, 136'. For example, the user may wish to view how other institutions within their own peer group have set up dosage limits for particular drugs. The vendor pharmacist can help the user obtain this information through the configuration information/activity information application 136, 136', and assist the user in selecting one or more drug entries to create and/or modify the user's institution's own configuration information, such as the institution's drug library. In view of the present description, many other examples come to mind for how the vendor personnel, such as a pharmacist, can assist a user in using the various interface screens, systems, and applications described herein, through the "hotline", with or without the vendor personnel viewing and/or taking over control of the customer's interface screens.

While the above-described embodiments of the invention were applied to medical devises such as infusion pumps, it will be understood by those skilled in the art that are medical devised that are capable of electronically reporting activity information and/or are configurable with configuration information can be sued with the system of the present invention. For example, a medical device for monitoring patient physiological or biochemical conditions, including but not limited to SpO2, capnography, EEG, EKG, blood pressure, and/or heart rate monitors, can be included in the system of the present invention. There are substantial benefits to institutions/facilities in having access to aggregated configuration information and/or activity information of monitoring devices alone or in conjunction with infusion pumps.

It should be emphasized that the above-described embodiments of the present invention are examples of implementations, and are merely set forth for a clear understanding of the principles of the invention. Many variations and modifications may be made to the above-described embodiment(s) of the invention without substantially departing from the principles of the invention. All such modifications are intended to be included herein within the scope of this disclosure and by the following claims.

What is claimed is:

1. A method of tracking and comparing activity or configuration information for a medical device within an institution, comprising the steps of:
    receiving from a plurality of institutions medical device activity or configuration library information and storing the received information to a database on a central computer system;
    creating for the plurality of institutions a peer definition in the database comprising at least one of:
        an institution type comprising one of rural, community, teaching/university, multi hospital health system, and/or
        bed size type comprising number of patient beds in the institution;
    assigning a peer group to each institution by matching institutions with selected peer definitions and storing the peer group assignment in the database;
    receiving an institution selection from a client computer;
    searching, using the central computer system, the database for at least another institution with a matching peer group to the selected institution;
    comparing, using the central computer system, medical device activity or configuration information received for the institution with respective medical device activity or configuration information received for the at least another institution with a matching peer group;
    providing a result for the comparison; and
    displaying the result on the client computer.

2. The method of claim 1 wherein the most recently received activity information for the institution is used within the comparing step.

3. The method of claim 1 further comprising the steps of:
    granting a configuration library developing institution access to view a portion of the medical device system activity information received from a plurality of other institutions within the peer group; and
    providing the developing institution access to programming code that enables the developing institution to copy a part of the viewed portion of the medical device system activity information received from a plurality of other institutions within the peer group into an institution-specific customized configuration library database.

4. The method of claim 1 further comprising the step of determining if the comparison result satisfies a predetermined condition wherein the predetermined condition is based at least in part on the respective system activity information received from the plurality of other institutions.

5. The method of claim 4 wherein the predetermined condition is one of:
    a) a predetermined specific percentage of a number of times a medical device configuration library information is edited during programming in relation to a number of times the medical device is programmed;
    b) predetermined acceptable number of buttons presses for programming in relation to a number of medical device buttons that are pressed during programming;
    c) predetermined amount of data that is considered acceptable to present summary information for the activity information in relation to an amount of data present in a database of activity information;
    d) a predetermined statistical value for the activity information in relation to a statistical calculation for the activity information; and/or,
    e) a predetermined amount of time it takes to program a medical device in relation to an amount of time it takes to program a medical device.

6. The method of claim 5 wherein the activity information used within the comparison is within a predetermined time interval.

7. The method of claim 4 further comprising the step of communicating an alert to the institution if the predetermined condition is satisfied.

8. The method of claim 1 wherein the peer definition can be further comprised of a medical device type comprising a recognized classification of medical devices.

9. The method of claim 1 wherein the peer definition can be further comprised of a service line type comprising a recognized clinical care area.

10. A method of using aggregated medical device data from a plurality of remote institutions/facilities, comprising the steps of:
- accessing an aggregation of a plurality medical device configuration/activity information stored in a memory in a central computer system, each of the plurality of medical device configuration/activity information received from a respective medication delivery system, each of the respective medication delivery systems having a respective plurality of medical devices associated therewith and utilized therein, and each of the respective remote medication delivery systems being associated with and implemented within a respective remote institution/facility of the plurality of remote institutions/facilities,
- creating for the plurality of institutions a peer definition in the memory comprising at least one of:
  - an institution type comprising one of rural, community, teaching/university, multi hospital health system, and/or
  - bed size type comprising number of patient beds in the institution; and
- assigning a peer group to each institution by matching institutions with selected peer definitions and storing the peer group assignment in the database;
- comparing at the central computer system entered or selected medical device configuration/activity information with the aggregated configuration/activity information which is within a peer group corresponding to the entered or selected configuration/activity information.

11. The method of claim 10 wherein the step of comparing comprises comparing at the central computer system entered or selected medical device configuration information with aggregated configuration/activity information for a peer group for an institution, for another peer group other than the peer group of the institution, and/or for all peer groups.

12. A method of using aggregated medical device data from a plurality of remote institutions/facilities, comprising the steps of:
- accessing an aggregation of a plurality of established medical device data stored in a memory in a central computer system, each of the plurality of established medication data received from a respective medication delivery system, each of the respective medication delivery systems having a respective plurality of medical devices associated therewith and utilized therein, and each of the respective remote medication delivery systems being associated with and implemented within a respective remote institution/facility of the plurality of remote institutions/facilities,
- creating for the plurality of institutions a peer definition in the memory comprising at least one of:
  - an institution type comprising one of rural, community, teaching/university, multi hospital health system, and/or
  - bed size type comprising number of patient beds in the institution; and
- assigning a peer group to each institution by matching institutions with selected peer definitions and storing the peer group assignment in the database;
- searching the aggregation of the plurality of established medical device data based on search parameters at the central computer system to obtain a search result; and,
- comparing the search result to a sub-group of the aggregated medical device data at the central computer system corresponding to a peer group.

13. The method of claim 12 wherein the search result is a drug library entry, wherein the sub-group is a peer group, and wherein the drug library entry is compared to activity information for medical devices within the same peer group of institutions/facilities.

14. The method of claim 12 wherein the search result is a drug library entry, wherein the sub-group is a clinical care area (CCA), and wherein the drug library entry is compared to activity information for medical devices within the same CCA within all institutions/facilities.

15. The method of claim 12 further comprising the step of transferring at least a portion of the search result and/or the aggregation of the plurality of established medical device data associated with the search result, to a local storage medium at a remote institution/facility for use within the respective medication delivery system.

* * * * *